US011813324B2

(12) United States Patent
Morrison

(10) Patent No.: US 11,813,324 B2
(45) Date of Patent: *Nov. 14, 2023

(54) METHODS FOR IMMUNIZING PRE-IMMUNE SUBJECTS AGAINST RESPIRATORY SYNCYTIAL VIRUS (RSV)

(71) Applicant: UNIVERSITY OF MASSACHUSETTS, Boston, MA (US)

(72) Inventor: Trudy G Morrison, Northborough, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/677,399

(22) Filed: Feb. 22, 2022

(65) Prior Publication Data

US 2022/0233680 A1     Jul. 28, 2022

Related U.S. Application Data

(63) Continuation of application No. 17/028,288, filed on Sep. 22, 2020, now abandoned, which is a continuation of application No. 16/339,219, filed as application No. PCT/US2017/052247 on Sep. 19, 2017, now Pat. No. 10,842,862.

(60) Provisional application No. 62/403,229, filed on Oct. 3, 2016.

(51) Int. Cl.
*A61K 39/17* (2006.01)
*A61P 31/14* (2006.01)
*A61K 39/12* (2006.01)
*C12N 7/00* (2006.01)
*A61K 39/00* (2006.01)

(52) U.S. Cl.
CPC .............. *A61K 39/17* (2013.01); *A61K 39/12* (2013.01); *A61P 31/14* (2018.01); *C12N 7/00* (2013.01); *A61K 2039/5256* (2013.01); *A61K 2039/5258* (2013.01); *C12N 2760/18122* (2013.01); *C12N 2760/18134* (2013.01); *C12N 2760/18171* (2013.01); *C12N 2760/18522* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| 7,951,384 | B2 | 5/2011 | Morrison et al. | 424/214.1 |
| 8,580,270 | B2 | 11/2013 | Morrison | 424/186.1 |
| 8,974,797 | B2 * | 3/2015 | Morrison | A61P 31/14 435/235.1 |
| 9,168,294 | B2 | 10/2015 | Morrison | 424/186.1 |
| 10,842,862 | B2 * | 11/2020 | Morrison | A61P 31/12 |
| 2013/0122032 | A1 | 5/2013 | Smith et al. | 424/186.1 |
| 2014/0134203 | A1 | 5/2014 | Morrison | 424/186.1 |
| 2016/0046675 | A1 | 2/2016 | Kwong et al. | 424/186.1 |
| 2016/0144021 | A1 | 5/2016 | Lambert et al. | 424/186.1 |

FOREIGN PATENT DOCUMENTS

| WO | WO/2009/105152 | 8/2009 |
| WO | WO/2016/103238 | 6/2016 |

OTHER PUBLICATIONS

U.S. Pat. No. 7,951,384 Morrison, T. and Pantua, H. D., issued May 31, 2011.
U.S. Pat. No. 8,580,270 Morrison, T. G., issued Nov. 12, 2013.
U.S. Pat. No. 8,974,797 Morrison, T., issued Mar. 10, 2015.
U.S. Pat. No. 9,168,294 Morrison, T. G., issued Oct. 27, 2015.
Arav-Boger, R. et al., (2002) "Polymorphisms of the Cytomegalovirus (CMV)-Encoded. Tumor Necrosis Factor-α and β-Chemokine Receptors in Congenital CMV Disease," *J. Infect. Dis.* 186(8), 1057-1064.
Bachmann, M. F. and Jennings, G. T., (2010) "Vaccine delivery: a matter of size, geometry, kinetics and molecular patterns," *Nat. Rev. Immunol.* 10(11), 787-796.
Beeler, J. A. and van Wyke Coelingh, K., (1989) "Neutralization epitopes of the F glycoprotein of respiratory syncytial virus: effect of mutation upon fusion function," *J. Virol.* 63(7), 2941.
Blair, K. S. et al., (2007) "Modulation of emotion by cognition and cognition by emotion," *Neuroimage* 35(1), 430-440.
Boyoglu-Barnum, S. et al., (2015) "An anti-G protein monoclonal antibody treats RSV disease more effectively than an anti-F monoclonal antibody in BALB/c mice," *Virology* 483, 117-125.
Chirkova, T. et al., (2013) "Respiratory syncytial virus G protein CX3C motif impairs human airway epithelial and immune cell responses," *J. Virol.* 87(24), 13466-13479.

(Continued)

*Primary Examiner* — Shanon A. Foley
*Assistant Examiner* — Myron G Hill
(74) *Attorney, Agent, or Firm* — Medlen & Carroll, LLP

(57) ABSTRACT

The invention provides methods for using virus-like particle (VLP) vaccines containing a stabilized pre-fusion respiratory syncytial virus (RSV) F protein to stimulate RSV neutralizing antibodies in pre-immune subjects. In one embodiment, the invention provides a method for immunizing a mammalian subject in need of immunizing against Respiratory Syncytial virus (RSV) infection, comprising, a) providing i) a pre-immune mammalian subject containing RSV neutralizing antibodies, ii) a first composition comprising recombinant chimeric Newcastle disease virus-like particles (ND VLPs), that contain a chimeric protein comprising, in N operable combination, 1) stabilized pre-fusion RSV F protein ectodomain, 2) transmembrane (TM) domain of NDV F protein, and 3) cytoplasmic (CT) domain of NDV F protein, and b) administering an immunologically effective amount of the first composition to the pre-immune subject to produce an immunized subject that comprises an increase in the level of the RSV neutralizing antibodies compared to the level of RSV neutralizing antibodies in the pre-immune subject. In one embodiment, the level of the RSV neutralizing antibodies in the pre-immune subject does not prevent RSV infection of the pre-immune subject.

28 Claims, 25 Drawing Sheets

Specification includes a Sequence Listing.

(56) References Cited

OTHER PUBLICATIONS

Collins, P. L. and Crowe, J. E., (2007) *Respiratory syncytial virus and metapneumovirus, 5th Ed.*, Lippincott Williams and Wilkins, Philadelphia.
Collins, P. L. and Graham, B. S., (2008) "Viral and Host Factors in Human Respiratory Syncytial Virus Pathogenesis," *J. Virol.* 82(5), 2040.
Cullen, L. M. et al., (2015) "Cotton rat immune responses to virus-like particles containing the pre-fusion form of respiratory syncytial virus fusion protein," *J. Transl. Med.* 13, 350-350.
Delgado, M. F. et al., (2009) "Lack of antibody affinity maturation due to poor Toll-like receptor stimulation leads to enhanced respiratory syncytial virus disease," *Nat. Med.* 15(1), 34-41.
Falsey, A. R. et al., (2005) "Respiratory Syncytial Virus Infection in Elderly and High-Risk Adults," *N. Engl. J. Med.* 352(17), 1749-1759.
Falsey, A. R. and Walsh, E. E., (2000) "Respiratory Syncytial Virus Infection in Adults," *Clin. Microbiol. Rev.* 13(3), 371.
Gilman, M. S. A. et al., (2016) "Rapid profiling of RSV antibody repertoires from the memory B cells of naturally infected adult donors," *Science Immunology* 1(6), eaaj1879.
Glezen, W. P. et al., (1986) "Risk of Primary Infection and Reinfection With Respiratory Syncytial Virus," *Am. J. Dis. Child.* 140(6), 543-546.
Graham, B. S., (2011) "Biological challenges and technological opportunities for respiratory syncytial virus vaccine development," *Immunol. Rev* 239(1), 149-166.
Gravel, K. A. et al., (2011) "The transmembrane domain sequence affects the structure and function of the Newcastle disease virus fusion protein," *J Virol.* 85(7), 3486-3497.
Hall, C. B., (2001) "Respiratory Syncytial Virus and Parainfluenza Virus," *N. Engl. J. Med.* 344(25), 1917-1928.
Hall, C. B. et al., (2001) "Respiratory Syncytial Virus Infections in Previously Healthy Working Adults," *Clin. Infect. Dis.* 33(6), 792-796.
Hall, C. B. et al., (2013) "Clinical and epidemiologic features of respiratory syncytial virus," *Curr. Top. Microbiol. Immunol.* 372, 39-57.
Han, L. L. et al., (1999) "Respiratory Syncytial Virus Pneumonia among the Elderly: An Assessment of Disease Burden," *J. Infect. Dis.* 179(1), 25-30.
Jardetzky, T. S. and Lamb, R. A., (2004) "A class act," *Nature* 427(6972), 307-308.
Karron, R. A., (2008) "Respiratory syncytial virus and parainfluenza virus vaccines," in *Vaccines, 5th ed.*, pp. 1146-1153, Saunders-Elsevier.
Lamb, R. A. and Parks, G. O., (2007) "Paramyxoviridae: the Viruses and Their Replication," 5th ed., pp. 1449-1496, Lippincott, Williams and Wilkins, Philadelphia.
Littel-van den Hurk, S. v. D. et al., (2007) "Immunopathology of RSV infection: prospects for developing vaccines without this complication," *Rev. Med. Virol.* 17(1), 5-34.
Magro, M. et al., (2012) "Neutralizing antibodies against the preactive form of respiratory syncytial virus fusion protein offer unique possibilities for clinical intervention," *P.N.A.S.* 109(8), 3089.
McGinnes Cullen, L. et al., (2015) "Murine Immune Responses to Virus-Like Particle- Associated Pre- and Postfusion Forms of the Respiratory Syncytial Virus F Protein," *J. Virol.* 89(13), 6835.
McGinnes, L. W. et al., (2011) "Assembly and Immunological Properties of Newcastle Disease Virus-Like Particles Containing the Respiratory Syncytial Virus F and G Proteins," *J. Virol.* 85(1), 366.
McGinnes, L. W. and Morrison, T. G., (2013) "Newcastle Disease Virus-Like Particles: Preparation, Purification, Quantification, and Incorporation of Foreign Glycoproteins," *Current Protocols in Microbiology* 30, Unit-18.12.
McGinnes, L. W. et al., (2010) "Assembly and Biological and Immunological Properties of Newcastle Disease Virus-Like Particles," *J. Virol.* 84(9), 4513.
McGinnes, L. W. et al., (2006) "Newcastle Disease Virus: Propagation, Quantification, and Storage," *Current Protocols in Microbiology* 1(1), 15F.12.11-15F.12.18.
McLellan, J. S. et al., (2013) "Structure-Based Design of a Fusion Glycoprotein Vaccine for Respiratory Syncytial Virus," *Science* 342(6158), 592.
McLellan, J. S. et al., (2010) "Structural basis of respiratory syncytial virus neutralization by motavizumab," *Nat. Struct. Mol. Biol.* 17(2), 248-250.
McLellan, J. S. et al., (2013) "Structure of RSV Fusion Glycoprotein Trimer Bound to a Prefusion-Specific Neutralizing Antibody," *Science* 340(6136), 1113.
McLellan, J. S. et al., (2011) "Structure of Respiratory Syncytial Virus Fusion Glycoprotein in the Postfusion Conformation Reveals Preservation of Neutralizing Epitopes," *J. Virol.* 85(15), 7788.
Morrison, T. G., (2010) "Newcastle disease virus-like particles as a platform for the development of vaccines for human and agricultural pathogens," *Future virology* 5(5), 545-554.
Morrison, T. G. and Walsh, E. E., (2013) "Subunit and virus-like particle vaccine approaches for respiratory syncytial virus," *Curr. Top. Microbiol. Immunol.* 372, 285-306.
Murawski, M. R. et al., (2010) "Newcastle Disease Virus-Like Particles Containing Respiratory Syncytial Virus G Protein Induced Protection in BALB/c Mice, with No Evidence of Immunopathology," *J. Virol.* 84(2), 1110-1123.
Ngwuta, J. O. et al., (2015) "Prefusion F-specific antibodies determine the magnitude of RSV neutralizing activity in human sera," *Sci. Transl. Med.* 7(309), 309ra162.
Openshaw, P. J. M. et al., (2001) "Immunopathogenesis of vaccine-enhanced RSV disease," *Vaccine* 20, S27-S31.
Openshaw, P. J. M. and Tregoning, J. S., (2005) "Immune Responses and Disease Enhancement during Respiratory Syncytial Virus Infection," *Clin. Microbiol. Rev.* 18(3), 541.
Pantua, H. D. et al., (2006) "Requirements for the Assembly and Release of Newcastle Disease Virus-Like Particles," *J. Virol.* 80(22), 11062-11073.
Perrone, L. A. et al., (2009) "Intranasal Vaccination with 1918 Influenza Virus-Like Particles Protects Mice and Ferrets from Lethal 1918 and H5N1 Influenza Virus Challenge," *J. Virol.* 83(11), 5726.
Polack, F. P. et al., (2003) "A role for nonprotective complement-fixing antibodies with low avidity for measles virus in atypical measles," *Nat. Med.* 9(9), 1209-1213.
Power, U. F., (2008) "Respiratory syncytial virus (RSV) vaccines—two steps back for one leap forward," *J. Clin. Virol.* 41(1), 38-44.
Pulendran, B. and Ahmed, R., (2011) "Immunological mechanisms of vaccination," *Nat. Immunol.* 12(6), 509-517.
Raboni, S. M. et al., (2003) "Respiratory tract viral infections in bone marrow transplant patients," *Transplantation* 76(1), 142-146.
Rey, G. U. et al., (2013) "Decrease in Formalin-Inactivated Respiratory Syncytial Virus (FI-RSV) Enhanced Disease with RSV G Glycoprotein Peptide Immunization in BALB/c Mice," *PLoS. One* 8(12), e83075.
Schmidt, M. R. et al., (2014) "Modification of the respiratory syncytial virus f protein in virus-like particles impacts generation of B cell memory," *J. Virol.* 88(17), 10165-10176.
Schmidt, M. R. et al., (2012) "Long-Term and Memory Immune Responses in Mice against Newcastle Disease Virus-Like Particles Containing Respiratory Syncytial Virus Glycoprotein Ectodomains," *J. Virol.* 86(21), 11654.
Smith, G. et al., (2012) "Respiratory Syncytial Virus Fusion Glycoprotein Expressed in Insect Cells Form Protein Nanoparticles That Induce Protective Immunity in Cotton Rats," *PLoS. One* 7(11), e50852.
Swanson, K. A. et al., (2011) "Structural basis for immunization with postfusion respiratory syncytial virus fusion F glycoprotein (RSV F) to elicit high neutralizing antibody titers," *P.N.A.S.* 108(23), 9619.
Tripp, R. A., (2004) "Pathogenesis of Respiratory Syncytial Virus Infection," *Viral Immunol.* 17(2), 165-181.
Tripp, R. A. et al., (2001) "CX3C chemokine mimicry by respiratory syncytial virus G glycoprotein," *Nat. Immunol.* 2(8), 732-738.

(56) References Cited

OTHER PUBLICATIONS

Weisel, F. J. et al., (2016) "A Temporal Switch in the Germinal Center Determines Differential Output of Memory B and Plasma Cells," *Immunity* 44(1), 116-130.
United States Patent Application Publication No. US 2013-0122032 A1 Smith, G. et al., published May 16, 2013.
United States Patent Application Publication No. US 2014-0134203 A1 Morrison, T., published May 15, 2014.
United States Patent Application Publication No. US 2016-0046675 A1 Kwong, P. D. et al., published Feb. 18, 2016.
United States Patent Application Publication No. US 2016-0144021 A1 Lambert, S. L. et al., published May 26, 2016.
WIPO PCT Patent Publication No. WO/2016/103238 Kwong, P. et al., published Jun. 30, 2016.
PCT International Search Report of International Application No. PCT/US2017/052247 dated Jan. 18, 2018.
WIPO PCT Patent Publication No. WO/2009/105152 Morrison, T., published Aug. 27, 2009.
McLellan, J. S. et al., (2013) "Structure-Based Design of a Fusion Glycoprotein Vaccine for Respiratory Syncytial Virus," *Science* 342(6158), 592-598.
Shinoff, J. J. et al., (2008) "Young Infants Can Develop Protective Levels of Neutralizing Antibody after Infection with Respiratory Syncytial Virus," *J. Infect. Dis.* 198(7), 1007-1015.
Arav-Boger, R. et al. (2002) "Polymorphisms of the Cytomegalovims (CMV)-Encoded Tumor Necrosis Factor-α and β-Chemokine Receptors in Congenital CMV Disease," *Journal of Infectious Diseases* 186(8), 1057-1064.
Bachmann, M. F. et al. (2010) "Vaccine delivery: a matter of size, geometry, kinetics and molecular patterns," *Nature Reviews Immunology* 10(11), 787-796.
Beeler, J. A. et al. (1989) "Neutralization epitopes of the F glycoprotein of respiratory syncytial virus: effect of mutation upon fusion function," *Journal of Virology* 63(7), 2941.
Chirkova, T. et al. (2013) "Respiratory syncytial Virus G protein CX3C motif impairs human airway epithelial and immune cell responses," *Journal of Virology* 87(24), 13466-13479.
Collins, P. L. et al. (2007) *Respiratory syncytial virus and metapneumovirus, 5th Ed.*, Lippincott Williams and Wilkins, Philadelphia.
Collins, P. L. et al. (2008) "Viral and Host Factors in Human Respiratory Syncytial Virus Pathogenesis," *Journal of Virology* 82(5), 2040.
Cullen, L. M. et al. (2015) "Cotton rat immune responses to Virus-like particles containing the pre-fusion form of respiratory syncytial virus fusion protein," *Journal of Translational Medicine* 13, 350-350.
Delgado, M. F. et al. (2009) "Lack of antibody affinity maturation due to poor Toll-like receptor stimulation leads to enhanced respiratory syncytial virus disease," *Nature Medicine* 15(1), 34-41.
Falsey, A. R. et al. (2005) "Respiratory Syncytial Virus Infection in Elderly and High-Risk Adults," *New England Journal of Medicine* 352(17), 1749-1759.
Falsey, A. R. et al. (2000) "Respiratory Syncytial Virus Infection in Adults," *Clinical Microbiology Reviews* 13(3), 371.
Gilman, M. S. A. et al. (2016) "Rapid profiling of RSV antibody repertoires from the memory B cells of naturally infected adult donors," *Science Immunology* 1(6), Article number: eaaj1879.
Glezen, W. P. et al. (1986) "Risk of Primary Infection and Reinfection With Respiratory Syncytial Virus," *American Journal of Diseases of Children* 140(6), 543-546.
Graham, B. S. (2011) "Biological challenges and technological opportunities for respiratory syncytial virus vaccine development," *Immunological Reviews* 239(1), 149-166.
Gravel, K. A. et al. (2011) "The transmembrane domain sequence affects the structure and function of the Newcastle disease virus fusion protein," *Journal of Virology* 85(7), 3486-3497.
Hall, C. B. (2001) "Respiratory Syncytial Virus and Parainfluenza Virus," *New England Journal of Medicine* 344(25), 1917-1928.

Hall, C. B. et al. (2001) "Respiratory Syncytial Virus Infections in Previously Healthy Working Adults," *Clinical Infectious Diseases* 33(6), 792-796.
Hall, C. B. et al. (2013) "Clinical and epidemiologic features of respiratory syncytial virus," *Current Topics in Microbiology and Immunology* 372, 39-57.
Han, L. L. et al. (1999) "Respiratory Syncytial Virus Pneumonia among the Elderly: An Assessment of Disease Burden," *Journal of Infectious Diseases* 179(1), 25-30.
Jardetzky, T. S. et al. (2004) "A class act," *Nature* 427(6972), 307-308.
Lamb, R. A. et al. (2007) "Paramyxoviridae: The Viruses and Their Replication," 5th ed., pp. 1449-1496, Lippincott, Williams and Wilkins, Philadelphia.
Littel Van Den Hurk, S. v. D. et al. (2007) "Immunopathology of RSV infection: prospects for developing vaccines without this complication," *Reviews in Medical Virology* 17(1), 5-34.
Magro, M. et al. (2012) "Neutralizing antibodies against the preactive form of respiratory syncytial virus fusion protein offer unique possibilities for clinical intervention," *Proceedings of the National Academy of Sciences* 109(8), 3089-3094.
McGinnes Cullen, L. et al. (2015) "Murine Immune Responses to Virus-Like Particle-Associated Pre- and Postfusion Forms of the Respiratory Syncytial Virus F Protein," *Journal of Virology* 89(13), 6835.
McGinnes, L. W. et al. (2011) "Assembly and Immunological Properties of Newcastle Disease Virus-Like Particles Containing the Respiratory Syncytial Virus F and G Proteins," *Journal of Virology* 85(1), 366.
McGinnes, L. W. et al. (2013) "Newcastle Disease Virus-Like Particles: Preparation, Purification, Quantification, and Incorporation of Foreign Glycoproteins," *Current Protocols in Microbiology* 30, Unit-18.12.
McGinnes, L. W. et al. (2010) "Assembly and Biological and Immunological Properties of Newcastle Disease Virus-Like Particles," *Journal of Virology* 84(9), 4513.
McLellan, J. S. et al. (2010) "Structural basis of respiratory syncytial virus neutralization by motavizumab," *Nature Structural & Molecular Biology* 17(2), 248-250.
McLellan, J. S. et al. (2013) "Structure of RSV Fusion Glycoprotein Trimer Bound to a Prefusion-Specific Neutralizing Antibody," *Science* 340(6136), 1113-1117.
McLellan, J. S. et al. (2011) "Structure of Respiratory Syncytial Virus Fusion Glycoprotein in the Postfusion Conformation Reveals Preservation of Neutralizing Epitopes," *Journal of Virology* 85(15), 7788.
Morrison, T. G. et al. (2013) "Subunit and virus-like particle vaccine approaches for respiratory syncytial virus," *Current Topics in Microbiology and Immunology* 372, 285-306.
Murawski, M. R. et al. (2010) "Newcastle Disease Virus-Like Particles Containing Respiratory Syncytial Virus G Protein Induced Protection in BALB/c Mice, with No Evidence of Immunopathology," *Journal of Virology* 84(2), 1110-1123.
Ngwuta, J. O. et al. (2015) "Prefusion F-specific antibodies determine the magnitude of RSV neutralizing activity in human sera," *Science Translational Medicine* 7(309), Article No. 309ra162.
Openshaw, P. J. M. et al. (2005) "Immune Responses and Disease Enhancement during Respiratory Syncytial Virus Infection," *Clinical Microbiology Reviews* 18(3), 541.
Pantua, H. D. et al. (2006) "Requirements for the Assembly and Release of Newcastle Disease Virus-Like Particles," *Journal of Virology* 80(22), 11062-11073.
Perrone, L. A. et al. (2009) "Intranasal Vaccination with 1918 Influenza Virus-Like Particles Protects Mice and Ferrets from Lethal 1918 and H5N1 Influenza Virus Challenge," *Journal of Virology* 83(11), 5726.
Polack, F. P. et al. (2003) "A role for nonprotective complement-fixing antibodies with low avidity for measles virus in atypical measles," *Nature Medicine* 9(9), 1209-1213.
Power, U. F. (2008) "Respiratory syncytial virus (RSV) vaccines—two steps back for one leap forward," *Journal of Clinical Virology* 41(1), 38-44.

(56) References Cited

OTHER PUBLICATIONS

Pulendran, B. et al. (2011) "Immunological mechanisms of vaccination," *Nature Immunology* 12(6), 509-517.
Rey, G. U. et al. (2013) "Decrease in Formalin-Inactivated Respiratory Syncytial Virus (FI-RSV) Enhanced Disease with RSV G Glycoprotein Peptide Immunization in BALB/c Mice," *PLoS One* 8(12), Article No. e83075.
Schmidt, M. R. et al. (2014) "Modification of the respiratory syncytial virus f protein in virus-like particles impacts generation of B cell memory," *Journal of Virology* 88(17), 10165-10176.
Schmidt, M. R. et al. (2012) "Long-Term and Memory Immune Responses in Mice against Newcastle Disease Virus-Like Particles Containing Respiratory Syncytial Virus Glycoprotein Ectodomains," *Journal of Virology* 86(21), 11654.
Shinoff, J. J. et al. (2008) "Young Infants Can Develop Protective Levels of Neutralizing Antibody after Infection with Respiratory Syncytial Virus," *Journal of Infectious Diseases* 198(7), 1007-1015.
Smith, G. et al. (2012) "Respiratory Syncytial Virus Fusion Glycoprotein Expressed in Insect Cells Form Protein Nanoparticles That Induce Protective Immunity in Cotton Rats," *PLoS One* 7(11), Article No. e50852.
Swanson, K. A. et al. (2011) "Structural basis for immunization with postfusion respiratory syncytial virus fusion F glycoprotein (RSV F) to elicit high neutralizing antibody titers," *Proceedings of the National Academy of Sciences* 108(23), 9619-9624.
Tripp, R. A. (2004) "Pathogenesis of Respiratory Syncytial Virus Infection," *Viral Immunology* 17(2), 165-181.
Tripp, R. A. et al. (2001) "CX3C chemokine mimicry by respiratory syncytial virus G glycoprotein," *Nature Immunology* 2(8), 732-738.
European Search Report for Application No. 17858887.7 dated Apr. 1, 2020.

\* cited by examiner

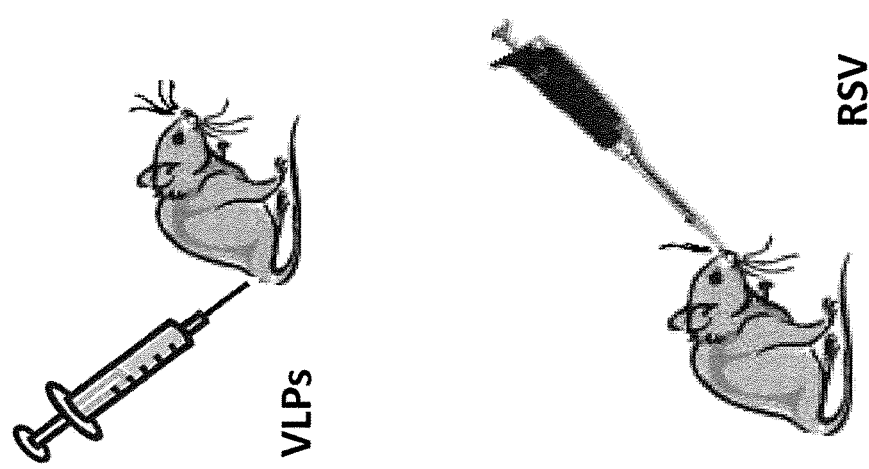
Approach
IM immunization with VLPs to mimic vaccination (NO ADJUVANT)
IN infection with RSV to mimic natural infection
Assessment of Efficacy
** Virus neutralization titers
Anti-F and anti-G serum antibody titers
Protection from virus challenge
Figure 4

FIGURE 5 (A) DNA sequence of the chimeric "RSV pre-F/F protein" (SEQ ID NO: 01) (also referred to as DS,CAV F/F)

*ATGGAGCTGCTGATCCTGAAGGCCAACGCCATTACCACCATTCTGACAGCCGTGACATTCTGC*
*TTCGCCTCCGGACAGAACATCACAGAGGAGTTCTATCAGAGCACCTGTTCCGCCGTCTCCAAA*
*GGATATCTGAGCGCCCTGAGGACCGGCTGGTATACCTCCGTGATCACCATCGAGCTTAGCAAC*
*ATCAAGGAGAACAAGTGCAATGGCACCGACGCCAAGGTCAAGCTCATCAAGCAAGAGCTTGA*
*CAAGTACAAAAACGCCGTCACCGAGCTTCAGCTGCTGATGCAGTCCACACCAGCTACCAACAA*
*CAGAGCCAGGAGAGAGCTTCCAGATTCATGAACTACACCCTGAACAACGCCAAGAAGACCAA*
*CGTGACCCTGTCCAAGAAAAGGAAAAGGAGGTTCCTGGGCTTCCTCCTGGGAGTGGGATCCG*
*CCATCGCTAGCGGCGTGGCCGTCTGTAAAGTCCTCCATCTGGAAGGCGAGGTCAACAAGATCA*
*AAAGCGCCCTGCTGTCCACAAACAAAGCTGTGGTCTCCCTGAGCAACGGCGTCAGCGTCCTGA*
*CCTTCAAGGTGCTCGACCTCAAGAACTACATCGACAAGCAACTGCTCCCCATCCTCAACAAGC*
*AGAGCTGCAGGATCAGCAACATTGAAACCGTGATCGAGTTCCAGCAGAAGAATAACAGGCTC*
*CTGGAGATCACCAGGGAGTTCAGCGTGAATGCTGGCGTGACAACCCCCGTCTCCACCTACATG*
*CTGACCAACAGCGAACTCCTGAGCCTGATCAACGATATGCCCATCACCAACGACCAGAAGAAG*
*CTCATGAGCAACAACGTCCAGATCGTGAGGCAGCAGAGCTACAGCATCATGTGCATTATCAA*
*AGAGGAGGTCCTGGCTTACGTGGTCCAGCTGCCCCTGTATGGAGTCATTGACACCCCTGCTG*
*GAAACTCCATACCAGCCCACTGTGTACAACCAACACCAAGGAGGGCAGCAACATCTGCCTCAC*
*CAGAACCGATAGGGGCTGGTACTGCGACAACGCCGGATCCGTGAGCTTCTTCCCCCAGGCCGA*
*GACCTGCAAGGTCCAGAGCAACAGGGTCTTCTGCGATACCATGAACAGCCTCACCCTGCCCTC*
*CGAGGTGAATCTCTGTAATGTCGACATCTTCAATCCAAAGTACGACTGTAAGATCATGACCA*
*GCAAGACCGACGTCAGCAGCAGCGTGATTACCAGCCTCGGAGCCATCGTGAGCTGTTACGGCA*
*AGACCAAGTGCACCGCCAGCAACAAGAACAGAGGAATTATCAAGACCTTCAGCAACGGATGC*
*GACTACGTCTCCAACAAGGCGTGGATACCGTCTCCGTGGGCAACACCCTGTACTACGTCAAC*
*AAGCAGGAAGGCAAAAGCCTGTACGTCAAGGGCGAGCCAATCATCAACTTTTACGATCCCCTC*
*GTCTTCCCATCCGATGAGTTCGACGCCAGCATCTCCCAAGTCAACGAGAAGATCAACCAGTCC*
*CTGGCCTTCATCAGAAAGTCCGACGAGCTCCTCCATAACGTCAACGCCGGGAAA*GGATATAT
CCCCGAAGCTCCTCGGGATGGTCAGGCCTACGTTCGCAAGGATGGAGAGTGGGTACT
GCTGTCTACTTTCCTGAGTACTACTAAT<u>CTCATTACCTATATCGCTTTAACTGCCATAT</u>
<u>CTCTTGTTGCGGTATACTTAGTCTGGTTCTAGCATGCTACCTAATGTACAAGCAAAAGG</u>
<u>CGCA</u>caaaagccttgtatgctgggataatacctggtcagatgagagccatacaaatgtga FIGURE 5 (B) Encoded protein sequence of the chimeric "RSV pre-F/F protein" (SEQ ID NO:02)

*MELLILKANAITTILTAVTFCFASGQNITEEFYQSTCSAVSKGYLSALRTGWYTSVITIELSNIKE*
*NKCNGTDAKVKLIKQELDKYKNAVTELQLLMQSTPATNNRARRELPRFMNYTLNNAKKTN*
*VTLSKKRKRRFLGFLLGVGSAIASGVAVCKVLHLEGEVNKIKSALLSTNKAVVSLSNGVSVLTF*
*KVLDLKNYIDKQLLPILNKQSCRISNIETVIEFQQKNNRLLEITREFSVNAGVTTPVSTYMLTN*
*SELLSLINDMPITNDQKKLMSNNVQIVRQQSYSIMCIIKEEVLAYVVQLPLYGVIDTPCWKLHT*
*SPLCTTNTKEGSNICLTRTDRGWYCDNAGSVSFFPQAETCKVQSNRVFCDTMNSLTLPSEVN*
*LCNVDIFNPKYDCKIMTSKTDVSSSVITSLGAIVSCYGKTKCTASNKNRGIIKTFSNGCDYVSNK*
*GVDTVSVGNTLYYVNKQEGKSLYVKGEPIINFYDPLVFPSDEFDASISQVNEKINQSLAFIRKS*
*DELLHNVNAGK*GYIPEAPRDGQAYVRKDGEWVLLSTFL*STTNL<u>ITYIALTAISLVCGILSL</u>*
<u>VLACYLMY</u>kqkqqklllwlgnnllggmratkm*

Figure 5 A - B

FIGURE 6 (A) DNA sequence of the chimeric "RSV post-F/F protein" (SEQ ID NO:03)

*ATGGAGCTTCTTATTCTCAAAGCCAATGCTATTACTACCATCCTGACAGCCGTGACATTTTGC
TTCGCCAGTGGACAGAATATCACTGAGGAATTCTATCAGAGCACCTGTTCCGCTGTATCAAA
AGGGTATCTCTCCGCATTACGAACCGGATGGTACACTTCAGTCATCACAATTGAACTTTCTAA
CATTAAAGAGAATAAGTGTAACGGGACTGACGCTAAAGTGAAGTTGATAAAGCAGGAGCTAG
ACAAATATAAGAATGCAGTAACTGAACTTCAGTTGCTTATGCAGTCCACACCTGCTACTAAC
AATAGAGCACGCCGTGAACTGCCTAGATTCATGAACTATACTCTTAATAACGCAAAAAAGAC
TAATGTTACCCTTTCCAAGAAACAGAAACAGCAAGCTATTGCTTCAGGAGTAGCAGTAAGTA
AGGTATTACATTTGGAAGGCGAAGTGAACAAAATTAAATCAGCACTGCTTTCCACTAACAAG
GCAGTAGTGAGTCTGTCTAATGGTGTTAGCGTTTTAACTTCTAAAGTGCTGGATTTAAAGAA
CTACATCGATAAACAGCTGCTCCCCATCGTAAACAAGCAGAGTTGCCGTATCAGCAACATAG
AGACAGTGATAGAGTTTCAGCAGAAGAACAATAGGCTGCTTGAAATAACTCGCGAATTTAGCG
TTAACGCAGGCGTGACTACCCCAGTGTCCACTTATATGCTGACAAACTCAGAGTTACTTTCTC
TGATCAACGACATGCCAATAACTAATGATCAGAAGAAATTAATGTCTAATAACGTGCAGATA
GTTCGGCAGCAGTCCTACAGTATCATGAGCATTATCAAGGAAGAGGTATTGGCCTATGTCGT
TCAGTTACCTTTATACGGTGTTATCGATACCCCATGTTGGAAGCTCCATACCAGCCCCTTGTG
TACTACCAATACTAAAGAGGGGAGCAATATTTGTCTAACTAGGACCGATAGGGGCTGGTACT
GCGACAACGCAGGGAGTGTTTCTTTCTTTCCTCAGGCAGAAACATGCAAGGTGCAGAGCAAC
AGAGTGTTTTGCGATACTATGAATAGCCTGACTCTGCCATCCGAAGTTAATCTGTGTAACGT
CGATATATTTAATCCAAAATACGATTGCAAAATCATGACTTCAAAAACAGACGTGAGCAGTT
CAGTCATAACTTCTCTAGGTGCCATTGTTTCATGCTACGGAAAAACTAAGTGTACCGCTAGC
AACAAAAACAGAGGTATTATCAAGACTTTCTCCAATGGCTGCGATTACGTTTCCAACAAGGG
TGTCGATACAGTCTCAGTCGGAATACCTTATATTACGTTAATAAACAGGAGGGGAAGTCTC
TGTATGTGAAAGGTGAGCCAATAATTAATTTTATGATCCTTTAGTATTTCCATCTGACGAG
TTTGACGCATCCATTTCTCAGGTTAACGAAAAGATCAACCAGAGCTTGGCTTTTATAAGGAA
GAGTGACGAGCTCCTCCATAACGTCAACGCCGGAAAAGTACTACTAAT*<u>CTCATTACCTATA
TGGCTTTAACTGCCATATCTCTTGTTTGCGGTATACTTAGTCTGGTTCTAGCATGCTACC
TAATGTACAAGCAAAAGGCGCA</u>acaaagaccttgttatggcttgggaataatacccttgggtcagatgagag
ctactacaaaatgtga FIGURE 6 (B) Encoded protein sequence of the chimeric "RSV post-F/F protein" (SEQ ID NO:04)

*MELLILKANAITTILTAVTFCFASGQNITEEFYQSTCSAVSKGYLSALRTGWYTSVITIELSNIKE
NKCNGTDAKVKLIKQELDKYKNAVTELQLLMQSTPATNNRARRELPRFMNYTLNNAKKTN
VTLSKKQKQQAIASGVAVSKVLHLEGEVNKIKSALLSTNKAVVSLSNGVSVLTSKVLDLKNYID
KQLLPIVNKQSCRISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTTNTK
EGSNICLTRTDRGWYCDNAGSVSFFPQAETCKVQSNRVFCDTMNSLTLPSEVNLCNVDIFNP
KYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRKSDELLHNVN
AGKSTTN*<u>LITYIALTAISLVCGILSLVLACYLM</u>Ykqkqqktlwlgnnlgnnraulkn FIGURE 7 (A) DNA sequence of the stabilized pre-fusion RSV F protein ectodomain (SEQ ID NO:05)

*ATGGAGCTGCTGATCCTGAAGGCCAACGCCATTACCACCATTCTGACAGCCGTGACATTCTGCTT
CGCCTCCGGACAGAACATCACAGAGGAGTTCTATCAGAGCACCTGTTCCGCCGTCTCCAAAGGA
TATCTGAGCGCCCTGAGGACCGGCTGGTATACCTCCGTGATCACCATCGAGCTTAGCAACATCAA
GGAGAACAAGTGCAATGGCACCGACGCCAAGGTCAAGCTCATCAAGCAAGAGCTTGACAAGTA
CAAAAACGCCGTCACCGAGCTTCAGCTGCTGATGCAGTCCACACCAGCTACCAACAACAGAGCC
AGGAGAGAGCTTCCCAGATTCATGAACTACACCCTGAACAACGCCAAGAAGACCAACGTGACCC
TGTCCAAGAAAAGGAAAAGGAGGTTCCTGGGCTTCCTCCTGGGAGTGGGATCCGCCATCGCTA
GCGGCGTGGCCGTCTGTAAAGTCCTCCATCTGGAAGGCGAGGTCAACAAGATCAAAAGCGCCC
TGCTGTCCACAAACAAAGCTGTGGTCTCCCTGAGCAACGGCGTCAGCGTCCTGACCTTCAAGGT
GCTCGACCTCAAGAACTACATCGACAAGCAACTGCTCCCCATCCTCAACAAGCAGAGCTGCAGG
ATCAGCAACATTGAAACCGTGATCGAGTTCCAGCAGAAGAATAACAGGCTCCTGGAGATCACCA
GGGAGTTCAGCGTGAATGCTGGCGTGACAACCCCCGTCTCCACCTACATGCTGACCAACAGCGA
ACTCCTGAGCCTGATCAACGATATGCCCATCACCAACGACCAGAAGAAGCTCATGAGCAACAAC
GTCCAGATCGTGAGGCAGCAGAGCTACAGCATCATGTGCATTATCAAAGAGGAGGTCCTGGCTT
ACGTGGTCCAGCTGCCCCTGTATGGAGTCATTGACACCCCCTGCTGGAAACTCCATACCAGCCCA
CTGTGTACAACCAACACCAAGGAGGGCAGCAACATCTGCCTCACCAGAACCGATAGGGGCTGG
TACTGCGACAACGCCGGATCCGTGAGCTTCTTCCCCCAGGCCGAGACCTGCAAGGTCCAGAGCA
ACAGGGTCTTCTGCGATACCATGAACAGCCTCACCCTGCCCTCCGAGGTGAATCTCTGTAATGTC
GACATCTTCAATCCAAAGTACGACTGTAAGATCATGACCAGCAAGACCGACGTCAGCAGCAGCG
TGATTACCAGCCTCGGAGCCATCGTGAGCTGTTACGGCAAGACCAAGTGCACCGCCAGCAACAA
GAACAGAGGAATTATCAAGACCTTCAGCAACGGATGCGACTACGTCTCCAACAAAGGCGTGGA
TACCGTCTCCGTGGGCAACACCCTGTACTACGTCAACAAGCAGGAAGGCAAAAGCCTGTACGTC
AAGGGCGAGCCAATCATCAACTTTTACGATCCCCTCGTCTTCCCATCCGATGAGTTCGACGCCAG
CATCTCCCAAGTCAACGAGAAGATCAACCAGTCCCTGGCCTTCATCAGAAAGTCCGACGAGCTCC
TCCATAACGTCAACGCCGGGAAA*

FIGURE 7 (B) Encoded protein sequence of the chimeric "RSV pre-F/F protein" the stabilized pre-fusion RSV F protein ectodomain (SEQ ID NO:06)

*MELLILKANAITTILTAVTFCFASGQNITEEFYQSTCSAVSKGYLSALRTGWYTSVITIELSNIKENKCNG
TDAKVKLIKQELDKYKNAVTELQLLMQSTPATNNRARRELPRFMNYTLNNAKKTNVTLSKKRKRRFL
GFLLGVGSAIASGVAVCKVLHLEGEVNKIKSALLSTNKAVVSLSNGVSVLTFKVLDLKNYIDKQLLPILN
KQSCRISNIETVIEFQQKNNRLLEITREFSVNAGVTPVSTYMLTNSELLSLINDMPITNDQKKLMSNN
VQIVRQQSYSIMCIIKEEVLAYVVQLPLYGVIDTPCWKLHTSPLCTTNTKEGSNICLTRTDRGWYCDN
AGSVSFFPQAETCKVQSNRVFCDTMNSLTLPSEVNLCNVDIFNPKYDCKIMTSKTDVSSSVITSLGAIV
SCYGKTKCTASNKNRGIIKTFSNGCDYVSNKGVDTVSVGNTLYYVNKQEGKSLYVKGEPIINFYDPLVF
PSDEFDASISQVNEKINQSLAFIRKSDELLHNVNAGKSTTN*

FIGURE 8 (A) DNA sequence of the stabilized post-fusion RSV F protein ectodomain (SEQ ID NO:07)

*ATGGAGCTTCTTATTCTCAAAGCCAATGCTATTACTACCATCCTGACAGCCGTGACATTTTGCTTC
GCCAGTGGACAGAATATCACTGAGGAATTCTATCAGAGCACCTGTTCCGCTGTATCAAAAGGGT
ATCTCTCCGCATTACGAACCGGATGGTACACTTCAGTCATCACAATTGAACTTTCTAACATTAAAG
AGAATAAGTGTAACGGGACTGACGCTAAAGTGAAGTTGATAAAGCAGGAGCTAGACAAATATA
AGAATGCAGTAACTGAACTTCAGTTGCTTATGCAGTCCACACCTGCTACTAACAATAGAGCACGC
CGTGAACTGCCTAGATTCATGAACTATACTCTTAATAACGCAAAAAAGACTAATGTTACCCTTTCC
AAGAAACAGAAACAGCAAGCTATTGCTTCAGGAGTAGCAGTAAGTAAGGTATTACATTTGGAA
GGCGAAGTGAACAAAATTAAATCAGCACTGCTTTCCACTAACAAGGCAGTAGTGAGTCTGTCTA
ATGGTGTTAGCGTTTTAACTTCTAAAGTGCTGGATTTAAAGAACTACATCGATAAACAGCTGCTC
CCCATCGTAAACAAGCAGAGTTGCCGTATCAGCAACATAGAGACAGTGATAGAGTTTCAGCAGA
AGAACAATAGGCTGCTTGAAATAACTCGCGAATTTAGCGTTAACGCAGGCGTGACTACCCCAGT
GTCCACTTATATGCTGACAAACTCAGAGTTACTTTCTCTGATCAACGACATGCCAATAACTAATG
ATCAGAAGAAATTAATGTCTAATAACGTGCAGATAGTTCGGCAGCAGTCCTACAGTATCATGAG
CATTATCAAGGAAGAGGTATTGGCCTATGTCGTTCAGTTACCTTTATACGGTGTTATCGATACCC
CATGTTGGAAGCTCCATACCAGCCCCTTGTGTACTACCAATACTAAAGAGGGGAGCAATATTTGT
CTAACTAGGACCGATAGGGGCTGGTACTGCGACAACGCAGGGAGTGTTTCTTTCTTTCCTCAGG
CAGAAACATGCAAGGTGCAGAGCAACAGAGTGTTTTGCGATACTATGAATAGCCTGACTCTGCC
ATCCGAAGTTAATCTGTGTAACGTCGATATATTTAATCCAAAATACGATTGCAAAATCATGACTT
CAAAAACAGACGTGAGCAGTTCAGTCATAACTTCTCTAGGTGCCATTGTTTCATGCTACGGAAAA
ACTAAGTGTACCGCTAGCAACAAAAACAGAGGTATTATCAAGACTTTCTCCAATGGCTGCGATTA
CGTTTCCAACAAGGGTGTCGATACAGTCTCAGTCGGGAATACCTTATATTACGTTAATAAACAGG
AGGGGAAGTCTCTGTATGTGAAAGGTGAGCCAATAATTAATTTTTATGATCCTTTAGTATTTCCA
TCTGACGAGTTTGACGCATCCATTTCTCAGGTTAACGAAAAGATCAACCAGAGCTTGGCTTTTAT
AAGGAAGAGTGACGAGCTCCTCCATAACGTCAACGCCGGGAAAAGTACTACTAAT*

FIGURE 8 (B) Encoded protein sequence of the stabilized post-fusion RSV F protein ectodomain (SEQ ID NO:08)

*MELLILKANAITTILTAVTFCFASGQNITEEFYQSTCSAVSKGYLSALRTGWYTSVITIELSNIKENKCNG
TDAKVKLIKQELDKYKNAVTELQLLMQSTPATNNRARRELPRFMNYTLNNAKKTNVTLSKKQKQQA
IASGVAVSKVLHLEGEVNKIKSALLSTNKAVVSLSNGVSVLTSKVLDLKNYIDKQLLPIVNKQSCRISNIE
TVIEFQQKNNRLLEITREFSVNAGVTTPVSTYMLTNSELLSLINDMPITNDQKKLMSNNVQIVRQQSY
SIMSIIKEEVLAYVVQLPLYGVIDTPCWKLHTSPLCTTNTKEGSNICLTRTDRGWYCDNAGSVSFFPQ
AETCKVQSNRVFCDTMNSLTLPSEVNLCNVDIFNPKYDCKIMTSKTDVSSSVITSLGAIVSCYGKTKCT
ASNKNRGIIKTFSNGCDYVSNKGVDTVSVGNTLYYVNKQEGKSLYVKGEPIINFYDPLVFPSDEFDASI
SQVNEKINQSLAFIRKSDELLHNVNAGKSTTN*

Figure 8 A - B

FIGURE 9 (A) Transmembrane (TM) domain of NDV F protein:
      1) DNA sequence (SEQ ID NO:09):
CTCATTACCTATATCGCTTTAACTGCCATATCTCTTGTTTGCGGTATACTTAGTCTGGTTCTAGCA
TGCTACCTAATGTACAAGCAAAAGGCGCA

2) Encoded protein sequence (SEQ ID NO:10)
LITYIALTAISLVCGILSLVLACYLMY

FIGURE 9(B) Cytoplasmic (CT) domain of NDV F protein:
      1) DNA sequence (SEQ ID NO:11)
Acaaaagaccttgttatggcttgggaataataccctgggtcagatgagagccactacaaaaatgtga

2) Encoded protein sequence (SEQ ID NO:12)
kqkaqqktllwlgnntlgqmrattkm

FIGURE 9(C) Foldon sequence
      1) DNA sequence (SEQ ID NO:13)
GGATATATCCCCGAAGCTCCTCGGGATGGTCAGGCCTACGTTCGCAAGGATGGAGAGTGGGTA
CTGCTGTCTACTTTCCTGAGTACTACTAAT

2) Encoded protein sequence (SEQ ID NO:14)
GYIPEAPRDGQAYVRKDGEWVLLSTFL

Figure 9 A - C

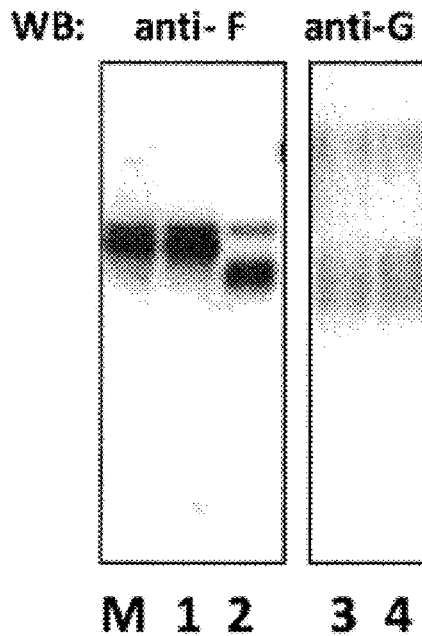
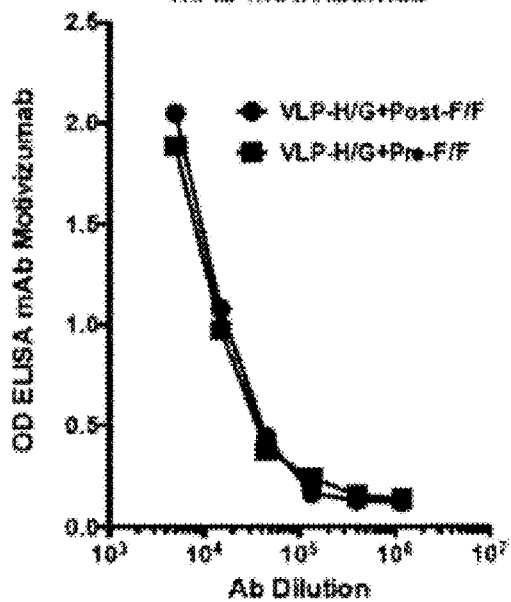
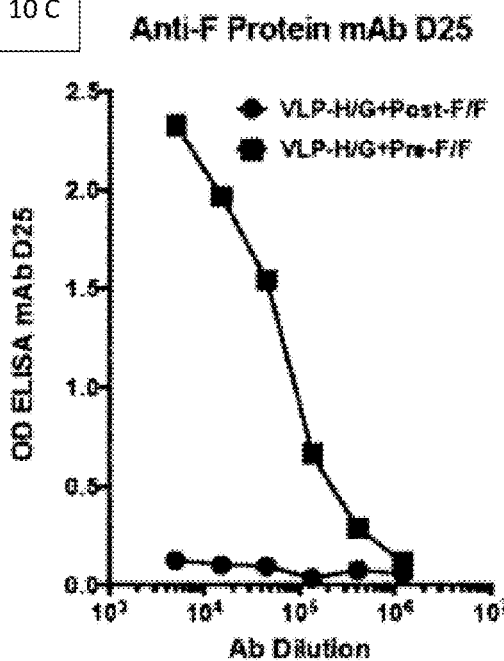
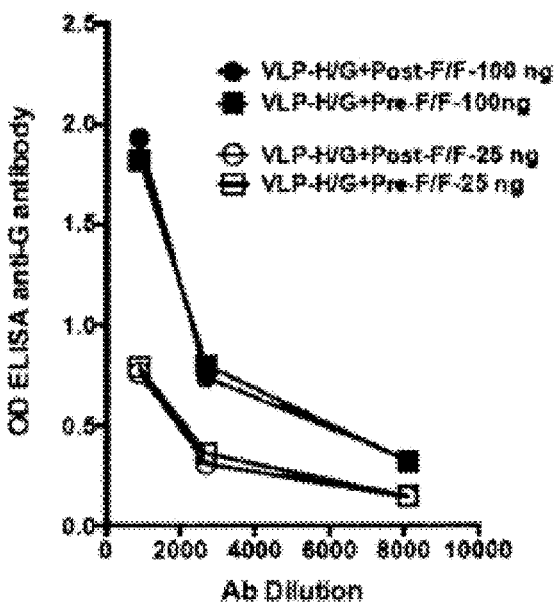

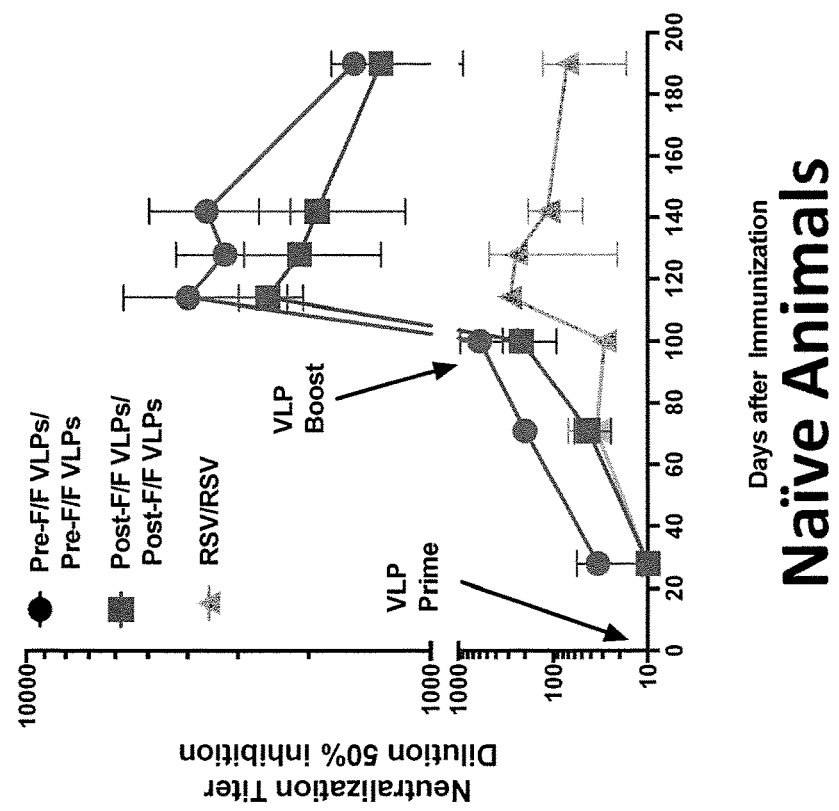
Fig. 16B
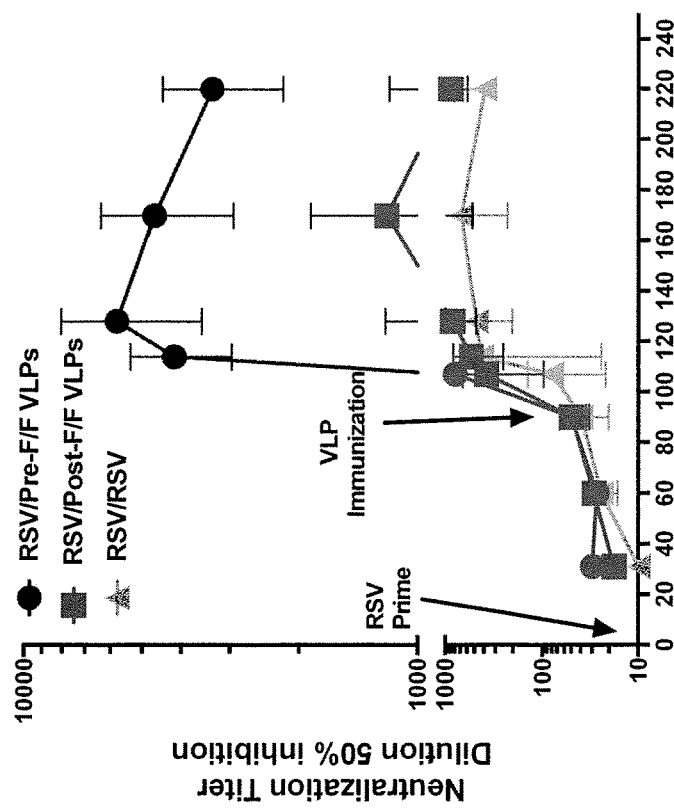
Fig. 16A
Fig. 16A – 16B

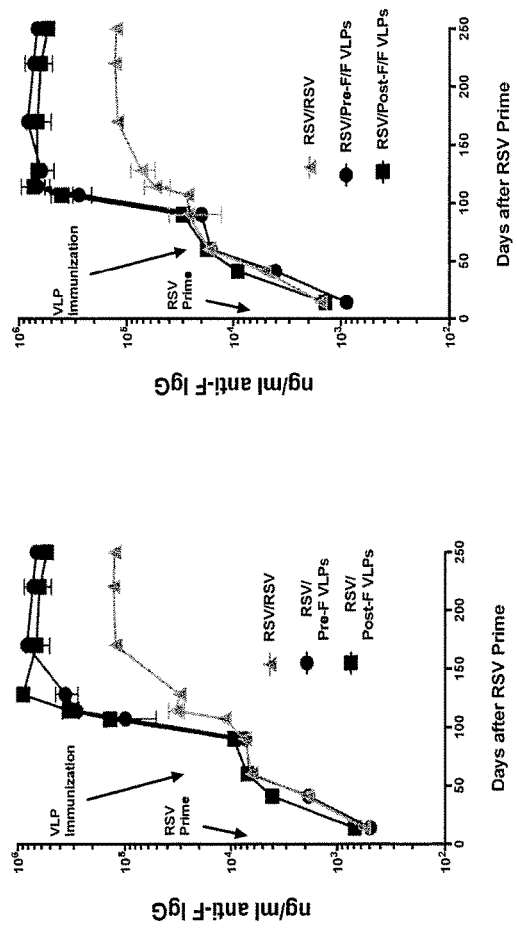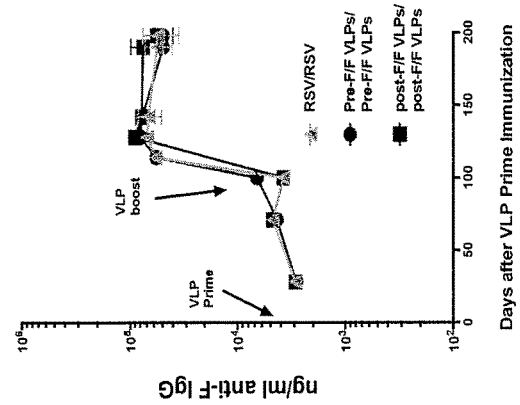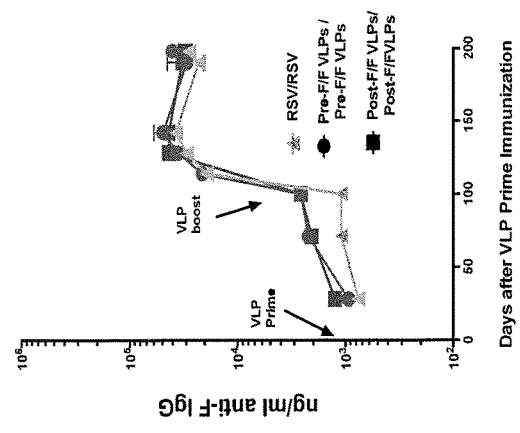
Fig. 17A – 17D

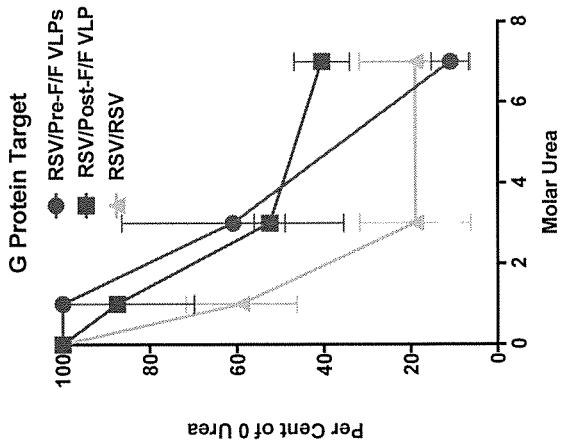
Fig. 21A
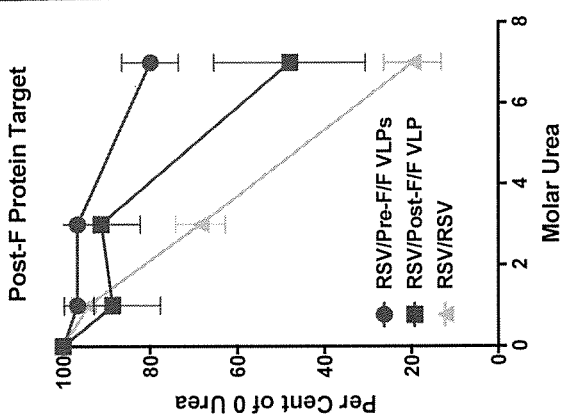
Fig. 21B
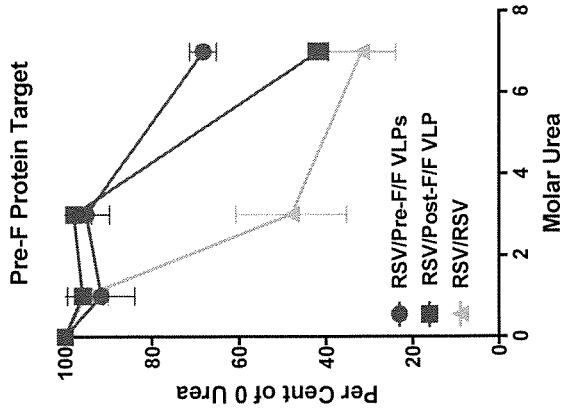
Fig. 21C
Fig. 21A – 21C

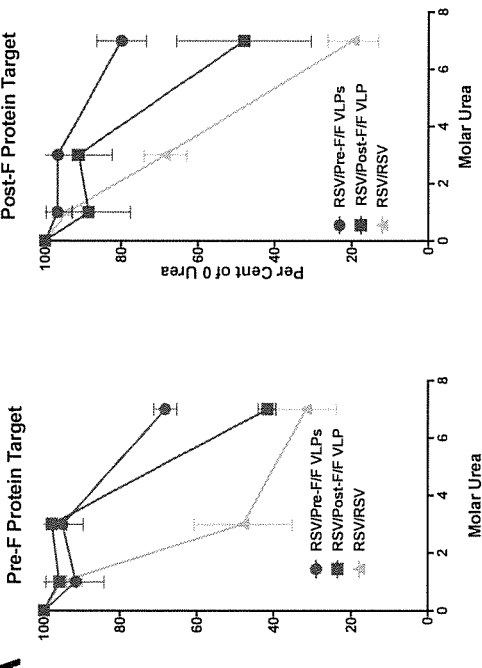
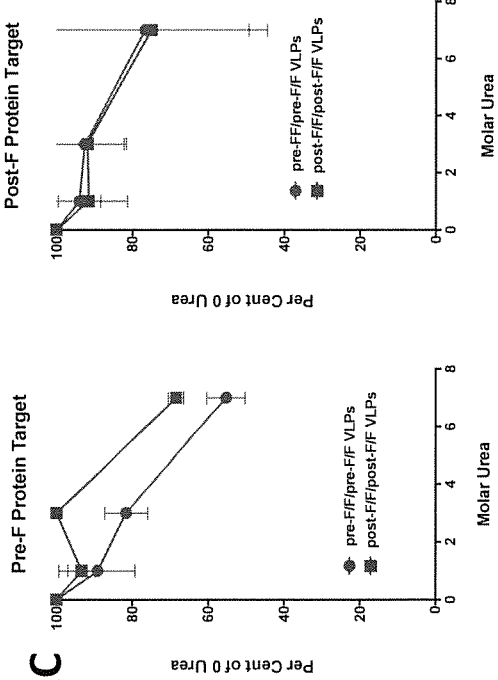
Fig. 22A – 22D

(A) NDV HN/RSV G (H/G) DNA Sequence (SEQ ID NO:15)

ATGAACCGCGCAGTTTGCCAAGTTGCGCTAGAGAATGATGAAAGGGAAGCGAAGAA
TACATGGCGCTTGGTATTCCGGATCGCAATCTTACTTTTAACAGTAATGACCTTAGC
CATCTCTGCGGCCGCCCTGGCATATAGTGCGAATCATAAGGTCACACCCACGACCGCAAT
CATTCAGGACGCTACTAGCCAAATCAAAAACACAACCCCTACGTATTTGACTCAGAACCCACA
ACTGGGTATTTCACCGTCGAATCCCAGTGAAATCACCTCCCAGATCACAACTATTCTTGCCTC
TACCACGCCTGGCGTTAAGAGCACACTCCAATCAACTACCGTAAAGACGAAAAACACAACTAC
CACCCAGACGCAGCCATCCAAGCCGACAACTAAACAAAGGCAGAACAAGCCCCCTTCGAAGCC
AAATAACGATTTCCACTTCGAGGTGTTTAACTTCGTCCCGTGTAGTATCTGCTCTAATAACCC
CACCTGTTGGGCTATTTGCAAAAGAATCCCTAACAAGAAGCCAGGAAAAAAGACGACAACTA
AACCCACCAAGAAGCCTACGTTGAAAACAACTAAGAAGGACCCGAAACCACAAACCACGAAG
AGCAAAGAAGTTCCCACAACTAAGCCTACCGAGGAACCGACGATCAATACAACTAAGACCAA
CATTATCACGACACTGCTCACTTCAAATACCACTGGTAACCCAGAGCTGACCTCCCAGATGGA
AACCTTCCATTCGACGAGTTCTGAGGGCAACCCCAGCCCTTCCCAAGTATCAACAACTTCGGA
ATACCCATCTCAGCCCAGTAGCCCTCCGAATACCCCACGACAA

(B) NDV HN/RSV G (H/G) Amino Acid Sequence (SEQ ID NO:16)

MNRAVCQVALENDEREAKNTWRLVFRIAILLLTVMTLAISAAALAYSANHKVTPTTAII
QDATSQIKNTTPTYLTQNPQLGISPSNPSEITSQITTILASTTPGVKSTLQSTTVKTKNTTTTQT
QPSKPTTKQRQNKPPSKPNNDFHFEVFNFVPCSICSNNPTCWAICKRIPNKKPGKKTTTKPT
KKPTLKTTKKDPKPQTTKSKEVPTTKPTEEPTINTTKTNIITTLLTSNTTGNPELTSQMETFH
STSSEGNPSPSQVSTTSEYPSQPSSPPNTPRQ

(C) RSV G DNA Sequence (SEQ ID NO:17) (GenBank No. X73355 for RSV A Strain)

ATGTCCAAGAACAAAGACCAGCGTACCGCTAAGACTCTGGAGCGCACATGGGATACGCTCAA
TCACTTGCTTTTCATCTCTAGCTGCCTGTACAAACTCAACTTGAAGTCAGTGGCCCAAATTAC
CCTTTCGATCCTGGCGATGATTATCAGTACTTCCCTCATCATTGCAGCTATCATTTTTAT
CGCCTCTGCGAATCATAAGGTCACACCCACGACCGCAATCATTCAGGACGCTACTAGCCAAAT
CAAAAACACAACCCCTACGTATTTGACTCAGAACCCACAACTGGGTATTTCACCGTCGAATCC
CAGTGAAATCACCTCCCAGATCACAACTATTCTTGCCTCTACCACGCCTGGCGTTAAGAGCAC
ACTCCAATCAACTACCGTAAAGACGAAAAACACAACTACCACCCAGACGCAGCCATCCAAGCC
GACAACTAAACAAAGGCAGAACAAGCCCCCTTCGAAGCCAAATAACGATTTCCACTTCGAGG
TGTTTAACTTCGTCCCGTGTAGTATCTGCTCTAATAACCCCACCTGTTGGGCTATTTGCAAAA
GAATCCCTAACAAGAAGCCAGGAAAAAAGACGACAACTAAACCCACCAAGAAGCCTACGTTG
AAAACAACTAAGAAGGACCCGAAACCACAAACCACGAAGAGCAAAGAAGTTCCCACAACTAA
GCCTACCGAGGAACCGACGATCAATACAACTAAGACCAACATTATCACGACACTGCTCACTTC
AAATACCACTGGTAACCCAGAGCTGACCTCCCAGATGGAAACCTTCCATTCGACGAGTTCTGA
GGGCAACCCCAGCCCTTCCCAAGTATCAACAACTTCGGAATACCCATCTCAGCCCAGTAGCCC
TCCGAATACCCCACGACAATAA

Figure 24A – 24C (D) RSV G Amino Acid Sequence (SEQ ID NO:18) (GenBank No. X73355 for RSV A Strain)

*MSKNKDQRTAKTLERTWDTLNHLLFISSCLYKLNLKSVAQ*ITLSILAMIISTSLIIAAIIFIASA
NHKVTPTTAIIQDATSQIKNTTPTYLTQNPQLGISPSNPSEITSQITTILASTTPGVKSTLQSTT
VKTKNTTTTQTQPSKPTTKQRQNKPPSKPNNDFHFEVFNFVPCSICSNNPTCWAICKRIPNK
KPGKKTTTKPTKKPTLKTTKKDPKPQTTKSKEVPTTKPTEEPTINTTKTNIITTLLTSNTTGN
PELTSQMETFHSTSSEGNPSPSQVSTTSEYPSQPSSPPNTPRQ

Figure 24D

METHODS FOR IMMUNIZING PRE-IMMUNE SUBJECTS AGAINST RESPIRATORY SYNCYTIAL VIRUS (RSV)

This application is a continuation application of, and claims priority to, copending U.S. application Ser. No. 17/028,288, filed Sep. 22, 2020, which is a continuation application of, and claims priority to, U.S. application Ser. No. 16/339,219 filed Apr. 3, 2019, which issued as U.S. Pat. No. 10,842,862 on Nov. 24, 2020, and which is the U.S. National stage filing under 35 U.S.C § 371 of, and which claims priority to, PCT Application No. PCT/US17/52247, filed Sep. 19, 2017, now abandoned, which claims priority under 35 U.S.C. § 119(e) to U.S. provisional Application Ser. No. 62/403,229, filed Oct. 3, 2016, now abandoned, the entire contents of each of which is herein incorporated by reference.

GOVERNMENT SUPPORT

This invention was made with government support under grant number AI114809 awarded by the National Institutes of Health (NIH). The government has certain rights in the invention.

A Sequence Listing has been submitted in an ASCII text file named "18737" created on Dec. 9, 2020, consisting of 38,132 bytes, the entire content of which is herein incorporated by reference.

FIELD OF THE INVENTION

The invention provides methods for using virus-like particle (VLP) vaccines containing a stabilized pre-fusion respiratory syncytial virus (RSV) F protein to stimulate RSV neutralizing antibodies in pre-immune subjects. In one embodiment, the invention provides a method for immunizing a mammalian subject in need of immunizing against Respiratory Syncytial virus (RSV) infection, comprising, a) providing i) a pre-immune mammalian subject containing RSV neutralizing antibodies, ii) a first composition comprising recombinant chimeric Newcastle disease virus-like particles (ND VLPs), that contain a chimeric protein comprising, in operable combination, 1) stabilized pre-fusion RSV F protein ectodomain, 2) transmembrane (TM) domain of NDV F protein, and 3) cytoplasmic (CT) domain of NDV F protein, and b) administering an immunologically effective amount of the first composition to the pre-immune subject to produce an immunized subject that comprises an increase in the level of the RSV neutralizing antibodies compared to the level of RSV neutralizing antibodies in the pre-immune subject. In one embodiment, the level of the RSV neutralizing antibodies in the pre-immune subject does not prevent RSV infection of the pre-immune subject.

BACKGROUND OF THE INVENTION

Respiratory syncytial virus (RSV) is the single most important cause of acute viral respiratory disease in infants and young children (1) frequently resulting in hospitalization and in significant mortality rates particularly in developing countries. RSV infection also substantially impacts elderly and immunocompromised populations (2-5). In addition, RSV infections result in considerable morbidity in normal adult populations (6). Despite the significance of RSV disease in many different populations, there are no vaccines available.

Numerous vaccine candidates have been characterized in preclinical and clinical studies spanning five decades but none have been licensed. Four interrelated problems have uniquely hindered RSV vaccine development. First is safety. Using classical methods for inactivated vaccine preparation, a formalin-inactivated preparation of purified virus (FI-RSV) not only failed to protect infants from infection, but also unexpectedly resulted in enhanced respiratory disease (ERD) upon subsequent infection with RSV (reviewed in (7-10)). The mechanisms responsible for this unusual response to a classically prepared vaccine are not completely understood even after decades of research using animal models.

A second major problem has been a lack of understanding of requirements for generation of high titers of neutralizing antibodies. A likely reason for the failure of most vaccine candidates is that they did not contain the appropriate form of the F protein. Like other paramyxovirus F proteins, the RSV F protein is folded into a metastable pre-fusion conformation and upon fusion activation refolds into the post-fusion conformation, which is structurally very different from the pre-fusion form (11-18). The pre-fusion form of F protein may be the most effective in stimulating optimally neutralizing antibodies. Indeed, the pre-fusion form contains unique epitopes, such as site 4, missing from the post fusion form. Antibodies to site ϕ neutralize virus at far lower concentrations than antibodies specific to sites common to both the pre- and post-F forms, sites I, II, and IV (18, 19). What was not recognized until recently is that the pre-fusion form of the RSV F protein is unusually unstable and that most vaccine candidates contained primarily the post fusion form. In spite of this, it has been argued, by some, that a post-fusion F protein will stimulate protection (20) and this form of F protein is now in clinical trials. In contrast, Magro, et al reported results, confirmed by Ngwuta, et al (21), that most neutralizing antibodies in human or rabbit anti-RSV immune sera do not bind to the post-fusion F protein but do bind to the pre-fusion F protein (22) suggesting that the majority of effective neutralizing antibody binding sites reside on the pre-fusion F protein. Furthermore, McLellan, et al (19) have shown that a soluble form of pre-fusion of F protein, stabilized by mutation (DS-Cav mutant F protein), stimulated significantly higher neutralizing antibody titers, in both mice and non-human primates, than those stimulated by post fusion forms.

A third problem is that the vast majority of the population has experienced RSV infection by 2 years of age (23). While RSV infection does not stimulate effective long-term protective immunity, any preexisting immunity could potentially impact the effectiveness of a vaccine. Thus any vaccine candidate must stimulate high titers of neutralizing antibody in the face of this preexisting immunity, a topic that has not been widely addressed A fourth related problem is a lack of understanding of requirements for the induction of effective long-lived and memory responses to RSV. One of the hallmarks of RSV infection is the observation that humans experience repeated infection caused by the same virus sero-group multiple times over several years or even within the same season (24, 25). Indeed, Pulendran and Ahmed (26) have noted that a successful RSV vaccine, in contrast to most vaccines, must stimulate better immune responses than natural infection. To date, the analysis of induction of long-term protective responses to vaccine candidates has not been the primary focus of RSV vaccine development.

Despite the significance of RSV disease in many different populations, the above problems have resulted in the lack of availability of RSV vaccine. What are needed are compositions methods for generating RSV neutralizing antibodies to vaccinate subjects with preexisting immunity.

SUMMARY OF THE INVENTION

In one embodiment, the invention provides a method for vaccinating and/or immunizing a mammalian subject in need thereof, comprising, a) providing i) a first pre-immune mammalian subject containing Respiratory Syncytial Virus (RSV) neutralizing antibodies, ii) a first composition comprising a recombinant chimeric Newcastle Disease virus-like particle (ND VLP) that contains a chimeric protein comprising, in operable combination, 1) stabilized prefusion RSV F protein ectodomain, 2) transmembrane (TM) domain of NDV F protein, and 3) cytoplasmic (CT) domain of NDV F protein, and b) administering an immunologically effective amount of the first composition to the first pre-immune subject under conditions for producing an immunized subject comprising an increase in the level of the RSV neutralizing antibodies compared to the level of RSV neutralizing antibodies in the first pre-immune subject.

In a further embodiment, the invention provides a method for immunizing a mammalian subject, comprising, a) providing i) a first pre-immune mammalian subject containing RSV neutralizing antibodies, ii) a first composition comprising recombinant chimeric Newcastle Disease virus-like particles (ND VLPs) that contain a chimeric protein comprising, in operable combination, 1) stabilized pre-fusion RSV F protein ectodomain, 2) transmembrane (TM) domain of NDV F protein, and 3) cytoplasmic (CT) domain of NDV F protein, and b) administering an immunologically effective amount of the first composition to the first pre-immune mammalian subject thereby immunizing said subject under conditions where the level of the RSV neutralizing antibodies in said immunized mammalian subject is increased. In one preferred embodiment, the level of the RSV neutralizing antibodies in the first pre-immune subject does not prevent RSV infection of the first pre-immune subject.

In another embodiment, the invention provides a method for immunizing a mammalian subject, comprising, a) providing i) a first pre-immune mammalian subject containing RSV neutralizing antibodies, ii) a first composition comprising recombinant chimeric Newcastle Disease virus-like particles (ND VLPs) that contain a chimeric protein comprising, in operable combination, 1) stabilized pre-fusion RSV F protein ectodomain, 2) transmembrane (TM) domain of NDV F protein, and 3) cytoplasmic (CT) domain of NDV F protein, and b) administering an immunologically effective amount of the first composition to the first pre-immune mammalian subject (e.g., to produce a first immunized mammalian subject), wherein said administering is under conditions that increase the level of the RSV neutralizing antibodies in said first immunized mammalian subject. In one preferred embodiment, the level of the RSV neutralizing antibodies in the first pre-immune subject does not prevent RSV infection of the first pre-immune subject. Thus, in some embodiments, the method comprises determining the presence of RSV infection in one or both of the first pre-immune subject and the first immunized subject.

In a particular embodiment, the level of the RSV neutralizing antibodies in the first immunized subject reduces RSV infection of the first immunized subject compared to the first pre-immune subject. Thus, in some embodiments, the method comprises detecting the level of RSV infection. In a further embodiment, the level of the RSV neutralizing antibodies in the first immunized subject reduces one or more symptoms of RSV infection. Thus, in some embodiments, the method comprises determining the level of RSV neutralizing antibodies in one or both of the first immunized subject and second immunized subject, and/or determining the presence and/or absence of one or more symptoms of RSV infection in one or both of the first immunized subject and the second immunized subject. In yet another embodiment, the level of the RSV neutralizing antibodies in the first immunized subject reduces susceptibility of the first immunized subject to RSV infection compared to the first pre-immune subject. Thus, in some embodiments, the method comprises determining susceptibility of the first immunized subject to RSV infection. In a further embodiment, the level of the RSV neutralizing antibodies in the first immunized subject reduces transmission of RSV infection from the first immunized subject. Thus, in some embodiments, the method comprises determining transmission of RSV infection from the first immunized subject. In one embodiment, the increase in the level of the RSV neutralizing antibodies in the first immunized subject is at least 100% compared to the level of RSV neutralizing antibodies in the first pre-immune subject. In a particular embodiment, the first immunized subject comprises an increase in the level of the RSV neutralizing antibodies compared to the level of RSV neutralizing antibodies in second immunized subject, wherein said second immunized subject is a second pre-immune subject that is infected with RSV. In one embodiment, the increase in the level of the RSV neutralizing antibodies in the first immunized subject is at least 100% compared to the level of RSV neutralizing antibodies in the second pre-immune subject that is infected with RSV. In another embodiment, the first immunized subject comprises an increase in the level of the RSV neutralizing antibodies compared to the level of RSV neutralizing antibodies in a second pre-immune subject that is immunized with a second composition comprising chimeric ND VLPs that contain, in operable combination 1) stabilized post-fusion RSV F protein ectodomain, 2) transmembrane domain of NDV F protein, and 3) cytoplasmic domain of NDV F protein. In a particular embodiment, the increase in the level of the RSV neutralizing antibodies in the first immunized subject is at least 100% compared to the second pre-immune subject that is treated with the second composition. In a further embodiment, the chimeric ND VLPs further comprise, in operable combination, foldon sequence listed as SEQ ID NO:14. In another embodiment, the level of the RSV neutralizing antibodies after a single administration of a dose of the first composition to the first pre-immune subject is substantially the same as the level of RSV neutralizing antibodies after twice administering the dose of the first composition to a control naïve subject. In another embodiment, the administering step is carried out at least once. In yet a further embodiment, the method further comprises comparing the level of the RSV neutralizing antibodies in the first immunized subject to the level of the RSV neutralizing antibodies in one or more test subjects selected from the group consisting of a) the first pre-immune subject, b) a second pre-immune subject that is infected with RSV, c) a second pre-immune subject that is treated with a second composition comprising chimeric ND VLPs that contain, in operable combination 1) stabilized post-fusion RSV F protein ectodomain, 2) transmembrane domain of NDV F protein, and 3) cytoplasmic domain of NDV F protein, wherein detecting an increase in the level of the RSV neutralizing antibodies in the first immunized subject compared to the level of the RSV neutralizing antibodies in the one or more test subjects indicates that the first immunized subject is immunized against the RSV infection. In a particular embodiment, the method further comprises detecting in the first immunized subject a reduction in one or more of (a) level of RSV infection, (b) one or more symptoms of RSV infection, (c) susceptibility to RSV infection, and (d) transmission of RSV infection, compared to the first pre-immune subject.

In one embodiment, the level, in the first immunized subject, of immunoglobulin G (IgG) that is specific for the stabilized pre-fusion RSV F protein ectodomain F is lower than the level, in one or both of the first immunized subject and the second immunized subject, of immunoglobulin G (IgG) that is specific for the stabilized post-fusion RSV F protein ectodomain F. In a particular embodiment, the ND VLP further comprises, in operable combination, CT domain of NDV HN protein, TM domain of NDV HN protein, and RSV G ectodomain protein. In another embodiment, the level of antibody that is specific for the RSV G ectodomain protein in the first immunized subject after a single administration of the first composition is higher than the level of antibody that is specific for the RSV G ectodomain protein in the pre-immune subject prior to the administration step. In a further embodiment, the single administration of the ND VLP that comprises the RSV G ectodomain protein to the first pre-immune mammalian subject increases the level of antibody that is specific for the RSV G ectodomain protein compared to the level of the antibody in a second immunized subject, wherein the second immunized subject is a second pre-immune subject that is immunized with a second composition comprising chimeric ND VLPs that contain, in operable combination 1) stabilized post-fusion RSV F protein ectodomain or stabilized pre-fusion RSV F protein ectodomain, 2) TM domain of NDV F protein, 3) CT domain of NDV F protein, 4) CT domain of NDV HN protein, 5) TM domain of NDV HN protein, and 6) RSV G ectodomain protein. In a particular embodiment, lung tissue of the first immunized subject contains a lower RSV titer than lung tissue of a naïve subject to which the first composition has not been administered. In yet another embodiment, the level of the RSV neutralizing antibodies after a single administration of the first composition to the first pre-immune subject is higher than the level of RSV neutralizing antibodies after a single administration of the first composition to a naïve subject. In an additional embodiment, the level of the RSV neutralizing antibodies after a single administration of the first composition to the first pre-immune subject is higher for at least a period from about 30 to about 220 days after the single administration than the level of RSV neutralizing antibodies after a single administration of the second composition to the second pre-immune subject. In a further embodiment, the level of splenic memory B cells in the first immunized mammalian subject is higher than the level of splenic memory B cells in the second immunized subject. In another embodiment, the level of splenic memory B cells in the first immunized mammalian subject is higher than the level of splenic memory B cells after RSV infection of the first pre-immune subject. In a further embodiment, the level of splenic memory B cells in the first immunized mammalian subject is higher than the level of splenic memory B cells after RSV infection of a naïve subject. In another embodiment, avidity of the RSV antibodies in the first immunized mammalian subject is higher than avidity of RSV antibodies in a pre-immune mammalian subject infected with RSV. In a further embodiment, the avidity of the antibody that is specific for the RSV G ectodomain protein in the first immunized mammalian subject is higher than avidity of antibody that is specific for the RSV G ectodomain protein in a pre-immune mammalian subject infected with RSV.

The invention also provides a vaccine comprising recombinant chimeric Newcastle Disease virus-like particles (ND VLPs) that contain a chimeric protein comprising, in operable combination, 1) stabilized pre-fusion RSV F protein ectodomain, 2) transmembrane (TM) domain of NDV F protein, and 3) cytoplasmic (CT) domain of NDV F protein. In a particular embodiment, the vaccine further comprises, in operable combination, foldon sequence listed as SEQ ID NO:14 and/or RSV G ectodomain protein sequence. In a particular embodiment, the RSV G ectodomain protein sequence is operably linked to NDV HN TM domain and to NDV HN CT domain.

The invention contemplates combining and/or removing and/or substituting features from different embodiments.

BRIEF DESCRIPTION OF THE DRAWINGS

FIG. 1A: neutralization titers (NA) in mice previously infected (primed) with RSV and then immunized with RSV, Pre-F VLPs, or Post-F VLPs (boost). NA titers in pooled sera at each time point were determined by plaque reduction assays in Hep-2 cells. Right panel FIG. 1B: NA titers from naïve mice primed and then boosted (day 90) with Pre-F or Post-F VLPs or RSV infected. Mock: infected/immunized with buffer. Titers on a log scale.

Figure 2:
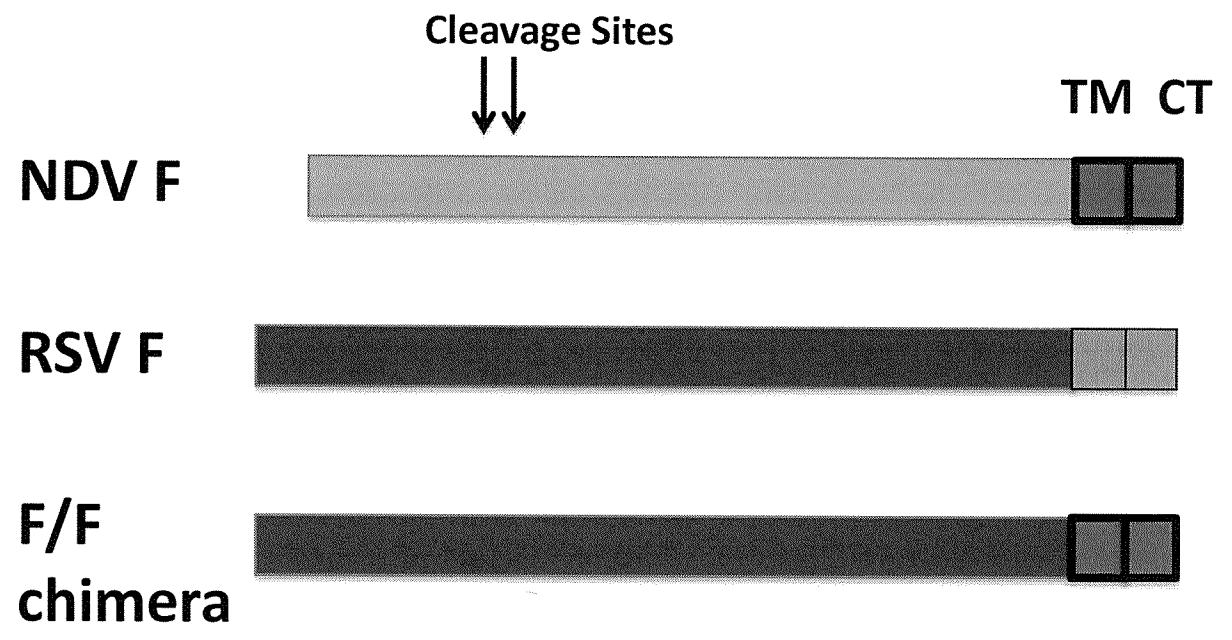

FIG. 2: Incorporation of RSV F Ectodomain into ND VLPs by to construct an "F/F chimera protein" exemplified by fusing RSV F ectodomain to the TM and CT domains of NDV F protein.

FIG. 4: Test of immunogenicity of VLPs as a vaccine in an animal (exemplified by mouse).

FIG. 5A-B: DNA sequence (SEQ ID NO:01) (FIG. 5A) and encoded protein sequence (FIG. 5B) (SEQ ID NO:02) of the chimeric "RSV pre-F/F protein," containing stabilized pre-fusion RSV F protein ectodomain (19) (SEQ ID NOs:05-06) (italics), transmembrane (TM) domain of NDV F protein (SEQ ID NOs:09-10) (underlined), cytoplasmic (CT) domain of NDV F protein (SEQ ID NOs:11-12) (lower case), and foldon sequence (SEQ ID NOs:13-14) (bold).

FIG. 6A-B: DNA sequence (FIG. 6A) (SEQ ID NO:03) and encoded protein sequence (FIG. 6B) (SEQ ID NO:04) of the chimeric "RSV post-F/F protein" containing stabilized post-fusion RSV F protein ectodomain (19) (SEQ ID NOs:07-08) (italics), transmembrane (TM) domain of NDV F protein (SEQ ID NOs:09-10) (underlined), and cytoplasmic (CT) domain of NDV F protein (SEQ ID NOs:11-12) (lower case).

FIG. 7A-B: Stabilized pre-fusion RSV F protein ectodomain (19): (FIG. 7A) DNA sequence (SEQ ID NO:05), and (FIG. 7B) encoded protein sequence (SEQ ID NO:06).

FIG. 8A-B: Stabilized post-fusion RSV F protein ectodomain (19): (FIG. 8A) DNA sequence (SEQ ID NO:07), and (FIG. 8B) encoded protein sequence (SEQ ID NO:08).

FIG. 9A-C: DNA sequences and encoded protein sequences of (FIG. 9A) transmembrane (TM) domain of NDV F protein (SEQ ID NOs:09-10), (FIG. 9B) cytoplasmic (CT) domain of NDV F protein (SEQ ID NOs:11-12), and foldon sequence (SEQ ID NOs:13-14).

FIG. 10A-D: Protein Content of VLPs. Panel FIG. 10A shows a Western blot of proteins present in stocks of VLP-H/G+Pre-F/F and VLP-H/G+Post-F/F. Proteins (electrophesed in the presence of reducing agent) in a polyacrylamide gel containing duplicate lanes of the proteins in the two VLPs were transferred to a membrane. One half was incubated with anti-F antibody (lanes M, 1, 2). The other half was incubated with anti-G protein antibody (lanes 3, 4). M: marker Pre-F/F protein. Lanes 1, 3: VLP-H/G+Pre-F/F; Lanes 2, 4: VLP-H/G+Post-F/F. The panel shows results of one of 3 separate blots with identical results. Panels B and C show binding of different concentrations of mAb motivizumab (panel FIG. 10B) or mAb D25 (Panel FIG. 10C) to each VLP in an ELISA as previously described[21]. Panel FIG. 10D shows binding of an anti-G protein antibody to two different concentrations of VLPs (concentrations in ng of F protein). Results were identical in three or four separate determinations.

FIG. 11B shows timing of prime immunization with VLPs or RSV infection of naïve animals (day 0) and the subsequent boost with VLPs or a second RSV infection (day 100). Sera were harvested at times indicated by arrows pointing upward. In one embodiment, blood collection was extended from 128 to 250 days (RSV primed) or 200 days (naïve) in order to determine durability of serum antibodies and monitor memory at later times after immunization.

FIG. 12A shows neutralization titers in pooled sera after a single immunization with VLPs of RSV previously infected animals. At day 128, the difference between results of VLP-H/G+Pre-F/F immunization and VLP-H/G+Post-F/F immunization was significant with a p value of 0.0009. The difference between VLP-H/G+Pre-F/F and RSV immunization was significant with a p value of 0.0005. Difference between VLP-H/G+Post-F/F and RSV immunization was not significant. All results are the average of four separate determinations with mean and standard deviation shown. Panel FIG. 12B shows neutralization titers in pooled sera after a prime and after a boost of naïve animals with VLPs or RSV. At day 71, p values for the difference between results of immunization with VLP-H/G+Pre-F/F and VLP-H/G+Post-F/F was 0.0005 and for the difference between VLP-H/G+Pre-F/F and RSV was 0.0030. The difference between VLP-H/G+Post-F/F and RSV was not significant. At day 128, the difference between results of VLP-H/G+Pre-F/F immunization and VLP-H/G+Post-F/F immunization was not significant. The p values for difference between VLP-H/G+Pre-F/F and RSV immunization was 0.035 and for the difference between VLP-H/G+Post-F/F and RSV immunization was 0.0012. Results are the average of three separate determinations with mean and standard deviation shown.

FIG. 14A shows ng/ml of anti-G protein IgG at different times in RSV-experienced animals. The results are the average of four separate determinations with average and standard deviations shown. At day 128, p value for the difference between RSV/VLP-H/G+Pre-F/F and RSV/VLP-H/G+Post-F/F immunization was 0.0057, the p value for the difference between RSV/VLP-H/G+Post-F/F and RSV/RSV was 0.002. The p value for the difference between RSV/VLP-H/G+Pre-F/F and RSV/RSV was 0.0002. Panel FIG. 14B shows ng/ml of anti-G protein IgG in immunized naïve animals. Results are the average of two separate determinations with standard deviations shown. At day 128, p values for differences between VLP-H/G+Pre-F/F and VLP-H/G+Post-F/F immunization, for RSV and VLP-H/G+Pre-F/F-VLP immunization, and for RSV and VLP-H/G+Post-F/F immunization were 0.042, 0.019, and 0.055 respectively.

FIG. 16A-B: Levels and Durability of Neutralizing Antibody Titers. Panel FIG. 16A shows neutralization titers in RSV primed animals. Panel FIG. 16B shows neutralization titers in Naïve animals.

FIG. 17A-D: Total anti-F IgG titers in (FIG. 17A) pre-F protein target RSV primed mice, (FIG. 17B) post-F protein target RSV primed mice, (FIG. 17C) pre-F protein target naïve mice, and (FIG. 17D) post-F protein target naïve mice. Circles denote RSV/Pre-F/F VLPs (panels FIGS. 17A and B), squares denote RSV/Post-F/F VLPs (Panels FIGS. 17A and B), and triangles denote RSV/RSV (Panels FIG. 17A, B, C, D); circles denote Pre-F/F VLPs/Pre-F/F VLPs, squares denote Post-F/F VLPs/Post F/F VLPs (Panels FIGS. 17 C and D).

FIG. 18C is the same as panel B for naïve mice, except with the Y axis scale is changed.

FIG. 21A-C: Measure of Avidity/Stability of Antigen-antibody Complexes in Increasing Urea for (FIG. 21A) pre-F protein target, (FIG. 21B) post-F protein target, and (FIG. 21C) G protein target.

FIG. 22A-D shows avidity of F protein antibodies stimulated in (FIG. 22A) RSV primed animals with pre-F protein target, (FIG. 22B) RSV primed animals with post-F protein target, (FIG. 22C) Naïve animals with pre-F protein target, and (FIG. 22D) Naïve animals with post-F protein target.

FIG. 24A-D shows (FIG. 24A) NDV HN/RSV G (H/G) DNA Sequence (SEQ ID NO:15), (FIG. 24B) NDV HN/RSV G (H/G)Amino Acid Sequence (SEQ ID NO:16), (FIG. 24C) RSV G DNA Sequence (SEQ ID NO:17) (GenBank No. X73355), and (FIG. 24D) RSV G Amino Acid Sequence (SEQ ID NO:18) (GenBank No. X73355). NDV HN Cytoplasmic Tail is in bold text; NDV HN Transmembrane Region is in underlined bold text; RSV G Ectodomain is in italics text; RSV G Cytoplasmic Tail is in underlined italics text; and RSV G Transmembrane Region is in bold italics text.

DEFINITIONS

Figure 1:
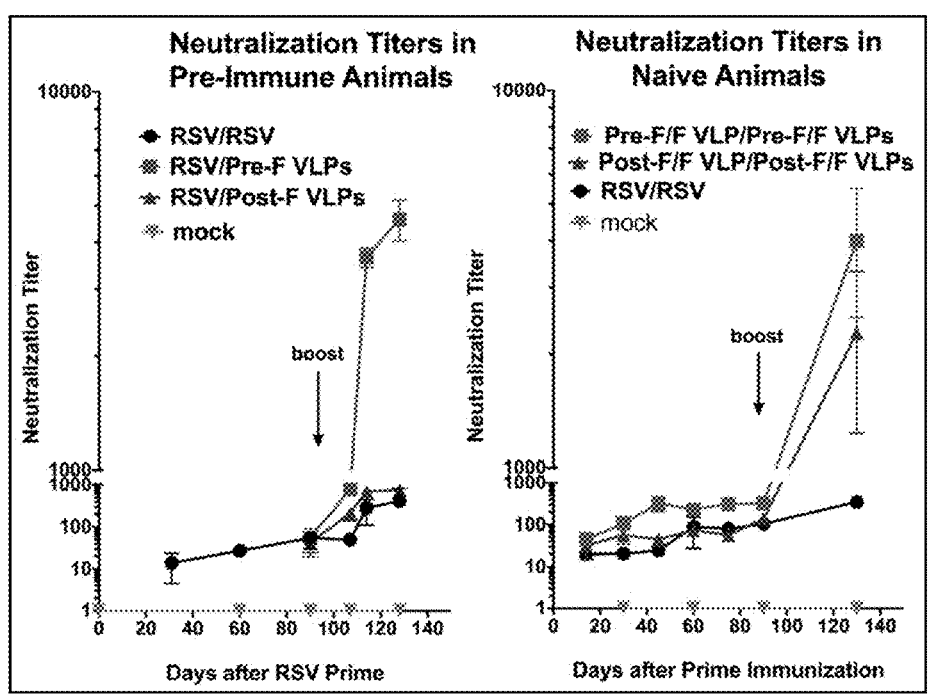
FIG. 1A-B: Immunization of pre-immune mice vs naïve mice. Left panel

To facilitate understanding of the invention, a number of terms are defined below.

The term "recombinant" molecule refers to a molecule that is produced using molecular biological techniques. Thus, "recombinant DNA molecule" refers to a DNA molecule that is comprised of segments of DNA joined together by means of molecular biological techniques. A "recombinant protein" or "recombinant polypeptide" as used herein refers to a protein molecule that is expressed using a recombinant DNA molecule. A "recombinant" virus-like particle (VLP) refers to a VLP that is expressed using a recombinant DNA molecule.

"Operable combination" and "operably linked" when in reference to the relationship between nucleic acid sequences and/or amino acid sequences refers to linking (i.e., fusing) the sequences in frame such that they perform their intended function. For example, when linking RSV F protein ectodomain to the TM domain of NDV F protein and to the CT domain of NDV F protein for the purpose of producing a VLP that elicits RSV neutralizing antibodies, then the arrangement and orientation of the linked sequences is such that a VLP is formed, and the RSV F protein is expressed as part chimeric "RSV F/F protein" (U.S. Pat. No. 8,580,270, issued to Morrison Nov. 12, 2013; U.S. Pat. No. 9,168,294, issued to Morrison Oct. 27, 2015). Alternatively, the linked F protein ectodomain may be the stabilized pre-fusion RSV F protein ectodomain (described in 19) (exemplified by SEQ ID NO:05, FIG. 7A) to generate a chimeric "RSV pre-F/F protein," exemplified by SEQ ID NO:02 (FIG. 5B), which contains the optional foldon sequence SEQ ID NO:14 (FIG. 9C). In yet another alternative, the linked F protein ectodomain may be the stabilized post-fusion RSV F protein ectodomain (described in 19) (exemplified by SEQ ID NO:08, FIG. 8B) to generate a chimeric "RSV post-F/F protein" exemplified by SEQ ID NO:04, FIG. 6B.

"Newcastle Disease Virus" and "NDV" refer to a negative-sense single-stranded RNA virus of the family Paramyxoviridae that causes a highly contagious zoonotic bird disease affecting many domestic and wild avian species.

"Respiratory Syncytial Virus" and "RSV" refer to a negative-sense, single-stranded RNA virus of the family Paramyxoviridae that causes a respiratory disease, especially in children. RSV is a member of the paramyxovirus subfamily Pneumovirinae. Its name comes from the fact that F proteins on the surface of the virus cause the cell membranes on nearby cells to merge, forming syncytia.

The terms "virus-like particle" and "VLP" as used herein, refer to a non-infective viral subunit that contains viral proteins that form a virus's outer shell and the surface proteins, resembles the external conformation of the virus from which the VLP was derived, and lacks viral DNA or RNA genome. A VLP comprising viral capsid proteins may undergo spontaneous self-assembly. In some embodiments, these viral proteins are embedded within a lipid bilayer. In some embodiments a "VLP"" interchangeably refer to a non-replicating, non-infectious particle shell that contains one or more virus proteins, lacks the viral RNA and/or DNA genome, and that approximately resembles live virus in external conformation. Methods for producing and characterizing recombinant VLPs containing Newcastle Disease Virus (NDV) proteins have been described (Pantua et al. (2006) J. Virol. 80:11062-11073; U.S. Pat. No. 7,951,384 issued to Morrison et al. on May 1, 2011; U.S. Pat. No. 8,974,797, issued to Morrison on Mar. 10, 2015, each of which is incorporated by reference). Further methods for producing NDV VLPs are disclosed herein.

"ND VLP" and "Newcastle Disease virus like particle" interchangeably refer to a VLP containing at least one Newcastle Disease Virus protein, preferably, at least NDV "matrix protein" (also referred to as "membrane protein" and "M protein"), which is a NDV protein localized between the envelope and the nucleocapsid core and facilitates the organization and maintenance of the virion structure and budding processes (U.S. Pat. No. 8,974,797, issued to Morrison on Mar. 10, 2015). Methods for producing, characterizing, and purifying recombinantly produced ND VLPs are known in the art (Pantua et al. (2006) J. Virol. 80:11062-11073; U.S. Pat. No. 8,974,797, issued to Morrison on Mar. 10, 2015; U.S. Pat. No. 9,168,294 issued to Morrison on Oct. 27, 2015).

"Pre-F/F VLPs" refer to ND VLPs that contain a stabilized pre-fusion RSV F protein ectodomain.

"Post-F/F VLPs" refer to ND VLPs that contain a stabilized post-fusion RSV F protein ectodomain.

"Symptoms of RSV infection" include ninny nose, decrease in appetite, coughing, sneezing, fever, wheezing, irritability, decreased activity, breathing difficulties, pneumonia, bronchiolitis, morbidity, and mortality.

The term "ectodomain" when in reference to a membrane protein refers to the portion of the protein that is exposed on the extracellular side of a lipid bilayer of a cell, virus and the like.

"Wild type RSV F protein ectodomain" is exemplified by the sequence described in Tale 7 and FIGS. 219-220 of U.S. Pat. No. 8,974,797, issued to Morrison on Mar. 10, 2015.

"Stabilized pre-fusion RSV F protein ectodomain is described in McLellan et al. (19) and exemplified by SEQ ID NO:06; FIG. 7B.

"Stabilized post-fusion RSV F protein ectodomain (described in McLellan et al. (38) and exemplified by SEQ ID NO:08; FIG. 8B.

"Transmembrane domain of NDV F protein" and "TM domain of NDV F protein" interchangeably refer to a protein sequence, and portions thereof, that spans the lipid bilayer of NDV. The TM domain of NDV F protein is exemplified by SEQ ID NO:10; FIG. 9A, and by Table 4 of U.S. Pat. No. 8,974,797, issued to Morrison on Mar. 10, 2015.

"Cytoplasmic domain of NDV F protein" and "CT domain of NDV F protein" interchangeably refer to refer to a protein sequence, and portions thereof, that is on the cytoplasmic side or virion interior or VLP interior of the lipid bilayer of NDV. The CT domain of NDV F protein is exemplified by SEQ ID NO:12; FIG. 9B, and by Table 4 of U.S. Pat. No. 8,974,797, issued to Morrison on Mar. 10, 2015.

The term "Pre-F/F VLP" herein refers to VLP-H/G+Pre-F/F; "Post-F/F VLPs" refers to VLP-H/G+Post-F/F VLPs.

The term "H/G" herein refers to the RSV G ectodomain, operably linked to CT of NDV HN and to TM of NDV HN.

The term "RSV G ectodomain" protein is exemplified by the sequence shown in italics text of the RSV G Amino Acid Sequence (SEQ ID NO:18) (GenBank No. X73355 for RSV A Strain) of FIG. 24D, which is encoded by the DNA sequence shown in italics text of RSV G DNA Sequence (SEQ ID NO:17) (GenBank No. X73355 for RSV A Strain) of FIG. 24C.

The term "expression vector" refers to a nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof.

Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

"Mammalian subject" includes human, non-human primate, murine (e.g., mouse, rat, cotton rat), ovine, bovine, ruminant, lagomorph, porcine, caprine, equine, canine, felines, ave, etc.

A subject "in need" of reducing one or more symptoms of a disease, and/or "in need" for a particular treatment (such as immunization) against a disease includes a subject that exhibits and/or is at risk of exhibiting one or more symptoms of the disease. For example, a subject may be in need of a reduction in one or more of (a) level of RSV infection, (b) one or more symptoms of RSV infection, (c) susceptibility to RSV infection, and (d) transmission of RSV infection, compared to a first pre-immune subject. In another example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The terms "Pre-immune," "RSV primed," and "RSV experienced" subject are used interchangeably to refer to a subject that has previously been in contact with, and/or previously infected by, RSV and/or an antigenic portion of RSV. This is exemplified by a subject that has been vaccinated against RSV through active human intervention, and/or a subject that has been exposed to RSV in the environment (e.g., by contact with another subject that is infected with RSV and/or contact with body fluid or sample from another subject that is infected with RSV). In one embodiment, a pre-immune subject contains detectable levels of RSV neutralizing antibodies (FIG. 1 A, and FIG. 12A), albeit these levels are not sufficient to (a) reduce (including prevent) subsequent RSV infection, (b) reduce symptoms of RSV infection, (c) reduce susceptibility to RSV infection, and/or (d) reduce transmission of RSV infection from the pre-immune subject.

Figure 12:
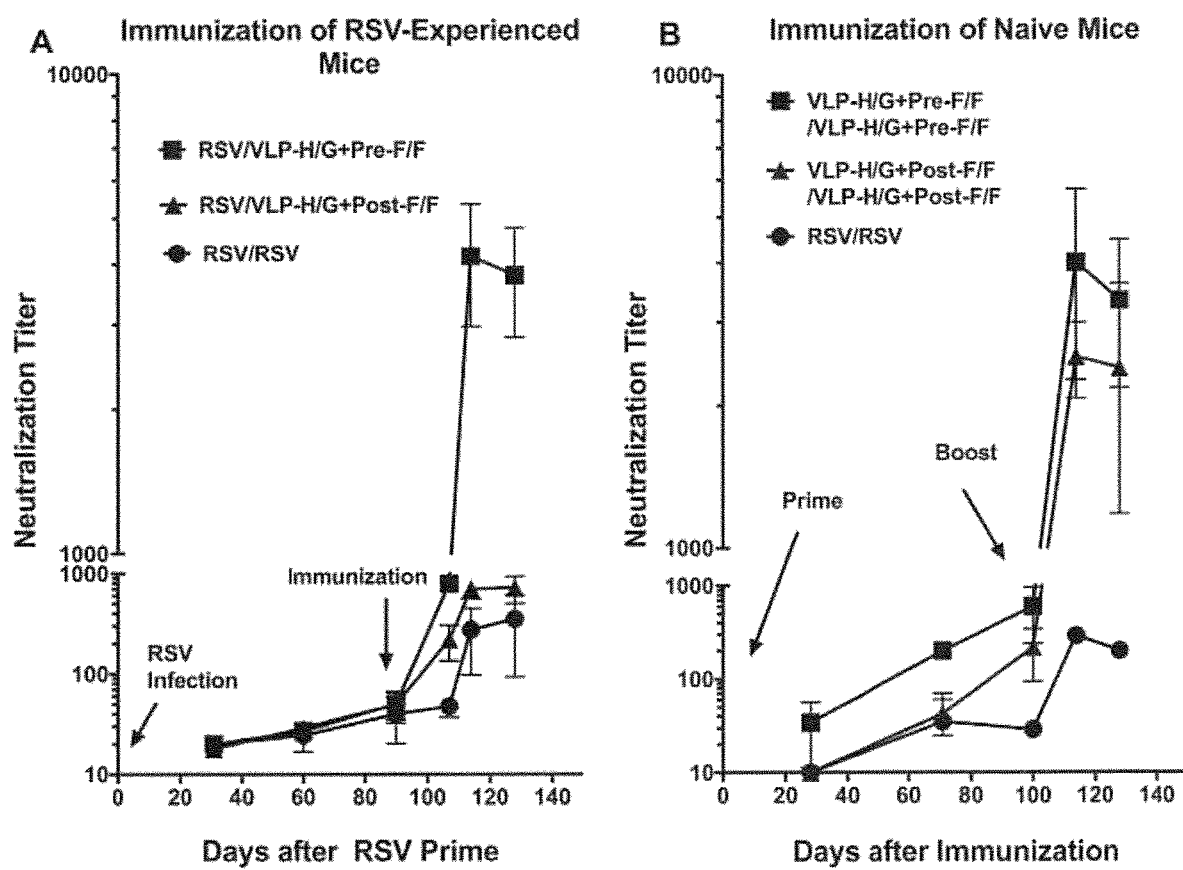
FIG. 12A-B: Neutralization Titers in Sera from RSV-experienced or Naïve Animals. Panel

"Naïve subject" refers to a subject that has not been previously in contact with, and/or previously infected by, RSV and/or an antigenic portion of RSV. In one embodiment, a naïve subject does not contain detectable levels of RSV neutralizing antibodies (FIG. 1B, and FIG. 12B).

"Immunogenically effective amount" refers to that amount of a molecule that elicits and/or increases production of neutralizing antibody in a host upon vaccination with the molecule.

The term "vaccine" refers to a pharmaceutically acceptable preparation that may be administered to a host to induce a humoral immune response (including eliciting a soluble antibody response), and/or cell-mediated immune response (including eliciting a cytotoxic T lymphocyte (CTL) response). The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. Vaccines may contain pharmaceutically acceptable carriers, adjuvants, and/or excipients. "Carriers" and "diluents" include water, saline solution, human serum albumin, oils, polyethylene glycols, aqueous dextrose, glycerin, propylene glycol or other synthetic solvents. "Adjuvant" refers to any compound which, when injected together with an antigen, non-specifically enhances the immune response to that antigen. "Excipient" is an inactive substance used as a carrier for the invention's compositions that may be useful for delivery, absorption, bulking up to allow for convenient and accurate dosage of the invention's compositions.

The term "administering" to a subject means delivering a molecule to a subject. "Administering" a composition to a subject in need of immunization against virus infection and/or in need of reducing one or more disease symptoms, includes prophylactic administration of the composition (i.e., before virus infection and/or before one or more symptoms of the disease are detectable) and/or therapeutic administration of the composition (i.e., after virus infection and/or after one or more symptoms of the disease are detectable). Administration also may be concomitant with (i.e., at the same time as, or during) virus infection and/or detection of one or more disease symptoms. Methods of administering the invention's compositions include, without limitation, administration in intranasal, parenteral, intraperitoneal, sublingual forms. In one preferred embodiment, administration is intranasal.

"Neutralizing antibody" ("NA") refers to an antibody that specifically binds to a target antigen, and neutralizes (i.e., reduces) one or more of the biological effects and/or functions of the antigen. This gives neutralizing antibodies the ability to fight viruses which attack the immune system, since they can neutralize (i.e., reduce) virus function (e.g., by reducing virion binding to receptors, reducing virus uptake into cells, reducing uncoating of the viral genomes in endosomes, and/or causing aggregation of virus particles. This is in contrast to non-neutralizing antibodies that are also produced after viral infection, and that bind specifically to virus particles, but do not neutralize (i.e., reduce) one or more of the biological effects and/or functions of the antigen to which they bind. Thus, neutralizing antibodies can produce reduced infectivity by the virus, reduced virus pathology (VEP), reduced susceptibility to infection (VES) by the virus, and/or reduced transmission of the virus. Methods for determining the presence and level of RSV neutralizing antibodies and nonneutralizing antibodies are known in the art (19, 30, 36), including a classical in vitro plaque reduction assay (36). Briefly, in this assay, pooled sera are used as are sera from individual subjects. For kinetics of induction of neutralizing antibodies, equal aliquots of sera from animals in each group obtained at multiple (e.g., four) times after immunization are pooled and used to determine titers. Virus titers of a stock of virus obtained after mixing virus with an equivalent volume of sera from buffer immunized subjects (TNE) are taken as 100% to account for any nonspecific neutralization by sera (control). The dilution of sera resulting in reduction in titer by 50% of the control is used to determine neutralization titers. Thus, a "detectable" level of RSV neutralizing antibody titer is a dilution of sera greater than 2, as exemplified by naïve subjects primed and then boosted (day 90) with Pre-F or Post-F VLPs or RSV infected (FIG. 1A, and FIG. 12A). Conversely, an "undetectable" level of RSV neutralizing antibody titer is a dilution of sera of less than 2, as exemplified by the naïve mock subjects that are infected/immunized with buffer (FIG. 1A).

"Nonneutralizing antibody" refers to an antibody that specifically binds to a target antigen, and does not neutralize (i.e., does not reduce) one or more of the biological effects and/or functions of the antigen. Most of the antibody made after RSV infection is nonneutralizing. This nonneutralizing antibody binds to virus but does not reduce RSV infection. This nonneutralizing antibody could inhibit induction of neutralizing antibody after RSV vaccination.

The terms "anti-G protein antibody" and "antibody that is specific for the RSV G protein" are interchangeably used to refer to an antibody (such as immunoglobulin G (IgG)) that specifically binds to RSV G protein and/or to antigenic portions thereof.

The terms "anti-F protein antibody" and "antibody that is specific for the RSV F protein" are interchangeably used to refer to an antibody (such as immunoglobulin G (IgG)) that specifically binds to RSV F protein and/or to antigenic portions thereof.

The terms "specific," "specifically binds," and grammatical equivalents, when made in reference to the binding of antibody to a molecule (e.g., binding of IgG to stabilized pre-fusion RSV F protein ectodomain F) refers to an interaction of the antibody with one or more epitopes on the molecule where the interaction is dependent upon the presence of a particular structure on the molecule.

The term "durable" and grammatical equivalents, when referring to antibody (such as neutralizing antibody) means that the detectable levels of antibody continue to be present in serum over a period of time. Durability also refers to the persistence of serum antibodies after immunization. Levels of serum antibodies (e.g., at 50-100 days after immunization) may be determined by measuring the levels of long lived, bone marrow associated plasma cells (LLPCs). That is, antibody durability is a measure of the levels of LLPCs.

The terms "avidity" and "affinity" when in reference to the interaction between an antibody and an antigen interchangeably refer to the strength of binding of the antibody to the antigen. Affinity is determined by on rates and off rates of antibody binding to antigen. B cells undergo affinity maturation in germinal centers. With increasing time, B cells secreting higher affinity antibodies are selected and persist while B cells secreting lower affinity antibodies are eliminated. Because polyclonal antibodies are a mixture of antibodies with different binding sites on an antigen and different affinities for that antigen, on and off rates cannot be precisely determined. Thus the strength of binding of polyclonal antibodies to an antigen is measured by the avidity of the antibodies. Avidity is classically defined and measured by the stability of the binding of polyclonal antibodies to an antigen in the presence of increasing concentrations of urea, ranging from 1-7 M. The results are plotted as the percent of binding at different urea concentrations with 100% representing the binding in no urea. The results are the average of all the antibodies in the population of antibodies in the serum. Lower percentages indicate weaker binding or weaker avidity. Methods for measuring avidity are known in the art (Delgado et al. 2009. Nature Med. 15:34-41, and Polack et al. 2003. Nat Med 9:1209-1213).

The term "splenic memory B cells" refer to long-lived B lymphocytes that are generated in the spleen. When an animal is immunized (or infected with a pathogen), the adaptive, T cell dependent immune response results in plasmablasts followed by the formation of germinal centers (3-4 days after antigen exposure) in the spleen. Germinal centers are the site in the spleen where memory B cells and LLPC (long lived plasma cells) are generated. Memory B cells form first followed by LLPC. Weise et al. 2016 Immunity 44: 116-130 estimates that memory B cells form beginning at 6-8 days after immunization with the formation rate peaking at day 11-26. Numbers continue to accumulate at least 40 days. In contrast, the rate of formation of LLPCs peaks at 30-32 days. LLPCs migrate to the bone marrow and generally persistently secrete antibody. They are largely responsible for the levels of serum antibody detected in unstimulated animals for prolonged periods of time (months, years, life of animal) with the duration likely depending upon the antigen. Memory B cells, after antibody class switching and affinity maturation, remain quiescent in the spleen until a second exposure to the antigen (infection or vaccine), at which time they are activated and begin secreting antibody. Memory B cells are a primary defense against infections that animals have previously experienced.

The terms "increase," "elevate," "raise," and grammatical equivalents (including "higher," "greater," etc.) when in reference to the level of any molecule (e.g., amino acid sequence, and nucleic acid sequence, antibody (such as IgG, anti-F protein antibody, and anti-G protein antibody), etc.), cells (such as memory B cells), and/or phenomenon (e.g., the level of RSV neutralizing antibodies, the titer RSV neutralizing antibodies, avidity, disease symptom, virus function, virion binding to receptors, virus uptake into cells, uncoating of the viral genomes in endosomes, infectivity by the virus, virus pathology (VEP), susceptibility to infection (VES) by the virus, transmission of the virus, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody (such as IgG anti-F protein antibody, and anti-G protein antibody), etc.), cell (such as memory B cells), and/or phenomenon (e.g., the level of RSV neutralizing antibodies, the titer RSV neutralizing antibodies, avidity, disease symptom, virus function, virion binding to receptors, virus uptake into cells, uncoating of the viral genomes in endosomes, infectivity by the virus, virus pathology (VEP), susceptibility to infection (VES) by the virus, transmission of the virus, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

"Substantially the same," "without substantially altering," "substantially unaltered," and grammatical equivalents, when in reference to the level of any molecule (e.g., amino acid sequence, and nucleic acid sequence, antibody (such as IgG, anti-F protein antibody, and anti-G protein antibody), etc.), cell (such as memory B cells), and/or phenomenon (e.g., the level of RSV neutralizing antibodies, the titer RSV neutralizing antibodies, avidity, disease symptom, virus function, virion binding to receptors, virus uptake into cells, uncoating of the viral genomes in endosomes, infectivity by the virus, virus pathology (VEP), susceptibility to infection (VES) by the virus, transmission of the virus, etc.) means that the quantity of molecule, cell, and/or phenomenon in the first sample (or in the first subject) is neither increased nor decreased by a statistically significant amount relative to the second sample (or in a second subject). Thus in one embodiment, the quantity of molecule, cell, and/or phenomenon in the first sample (or in the first subject) is from 90% to 100% (including, for example, from 91% to 100%, from 92% to 100%, from 93% to 100%, from 94% to 100%, from 95% to 100%, from 96% to 100%, from 97% to 100%, from 98% to 100%, and/or from 99% to 100%) of the quantity in the second sample (or in the second subject).

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc. In another example, the term "at least 95%" includes each numerical value (including fractional numbers and whole numbers) from 95% to 100%, including, for example, 95%, 96%, 97%, 98%, 99% and 100%.

DESCRIPTION OF THE INVENTION

A major issue for development of RSV vaccines is that the vast majority of the human population has experienced an RSV infection by 2 years of age (37). In addition, most people experience RSV infections repeatedly during their lifetimes indicating that RSV infection does not stimulate effective memory responses for neutralizing antibodies (37). However, any preexisting immunity could impact the effectiveness of a vaccine. Thus a successful vaccine candidate must stimulate high titers of neutralizing antibody in the face of this preexisting immunity.

The invention solves this problem by providing methods for using VLP vaccines containing a stabilized pre-fusion respiratory syncytial virus (RSV) F protein to stimulate RSV neutralizing antibodies in pre-immune subjects.

Data herein demonstrates that RSV primed animals respond differently to RSV vaccines than naïve mice. This suggests that vaccine candidates tested in naïve animals may yield results not applicable to the vast majority of the human population. This further suggests that vaccine candidates need to be tested in previously infected animals or humans (which comprise the majority of the human population).

Data herein further demonstrates that RSV vaccine candidates containing the pre-fusion F protein are far superior to vaccines containing the post-fusion F protein, particularly in RSV primed animals suggesting that successful vaccine candidates should contain a stabilized pre-fusion F protein, as described herein.

The exemplary experiments described herein (Examples 1-12) assessed the generation of protective immune responses in mice previously infected with RSV by the invention's virus-like particle (VLP) vaccines that contain a stabilized pre-fusion form of the RSV F protein, in comparison with control stabilized post-fusion F protein. Data herein demonstrate that a single immunization of RSV-experienced animals with the invention's stabilized pre-fusion F protein VLP stimulated high titers of neutralizing antibody while a single injection of a post-fusion F protein VLP or a second RSV infection only weakly stimulated neutralizing antibody titers. These results show that prior RSV infection induces neutralizing antibody memory responses, which can be activated by pre-F protein VLPs but not by post-F protein VLPs or a subsequent infection. Thus the F protein conformation has a major impact on enhancing production of neutralizing antibodies in RSV-experienced animals. Furthermore, although both VLPs contained the same RSV G protein, the invention's pre-F VLP stimulated significantly higher titers of total anti-G protein IgG than the post-F VLP in both naïve and RSV-experienced animals. Thus the F protein conformation also influences anti-G protein responses.

The invention is further described as follows under (A) Vaccines, (B) RSV Neutralizing Antibody Titers and Durability, (C) Anti-F Protein Antibody And Anti-G Protein Antibody, (D) Spleen Memory B cells, and (E) Avidity.

(A) Vaccines

The invention provides a vaccine comprising recombinant chimeric Newcastle Disease virus-like particles (ND VLPs) that contain a chimeric protein comprising, in operable combination, (I) stabilized pre-fusion RSV F protein ectodomain, (2) transmembrane (TM) domain of NDV F protein, and (3) cytoplasmic (CT) domain of NDV F protein (Example 1). In some embodiments, the vaccine further comprises, in operable combination, one or more foldon sequence listed as SEQ ID NO:14. In an alternate embodiment, the vaccine further comprises RSV G ectodomain sequence operably linked to the TM and CT domains of the NDV HN protein (Example 1).

(B) RSV Neutralizing Antibody Titers and Durability

In one embodiment, the invention provides a method for immunizing a mammalian subject in need thereof (such as in need for immunizing against Respiratory Syncytial virus (RSV) infection), comprising, a) providing i) a first pre-immune mammalian subject containing RSV neutralizing antibodies, ii) a first composition comprising a recombinant chimeric ND VLP, exemplified by SEQ ID NO:02; FIG. 5B, (McGinnes Cullen et al. (2015) J Transl. Med 13:350) that contains a chimeric protein comprising, in operable combination, 1) stabilized pre-fusion RSV F protein ectodomain of McLellan et al. (19) (exemplified by SEQ ID NO:06; FIG. 7B), 2) transmembrane (TM) domain of NDV F protein (exemplified by SEQ ID NO:10; FIG. 9A), and 3) cytoplasmic (CT) domain of NDV F protein (exemplified by SEQ ID NO:12; FIG. 9B), and b) administering an immunologically effective amount of the first composition to the first pre-immune subject to produce an immunized subject that comprises an increase in the level of the RSV neutralizing antibodies compared to the level of RSV neutralizing antibodies in the first pre-immune subject, thereby immunizing the first pre-immune subject against the RSV infection (FIG. 1 A, FIG. 12A, and FIG. 16A).

In one embodiment, the chimeric ND VLP further comprises, in operable combination, a foldon sequence, exemplified by SEQ ID NO:14; FIG. 9C.

In one embodiment, the level of the RSV neutralizing antibodies in the first pre-immune subject does not prevent RSV infection of the first pre-immune subject.

In a further embodiment, the level of the RSV neutralizing antibodies in the immunized subject reduces (including 100% prevention) one or more of RSV infection of the immunized subject compared to the first pre-immune subject, and/or reduces (including 100% prevention) one or more symptoms of RSV infection, and/or reduces (including 100% prevention) susceptibility of the of the immunized subject to RSV infection compared to the first pre-immune subject, and/or reduces (including 100% prevention) transmission of RSV infection from the immunized subject to a second subject, such as to a pre-immune subject or to another immunized subject.

One surprising aspect of the invention's methods, is the increase in the level of the RSV neutralizing antibodies compared to the level of RSV neutralizing antibodies in the first pre-immune subject (FIG. 1A, and FIG. 12A).

In one particular embodiment, the increase in the level of the RSV neutralizing antibodies in the immunized subject is at least 100%, including at least from 100% to 10,000%, from 100% to 9,000%, from 100% to 8,000%, from 100% to 7,000%, from 100% to 6,000%, from 100% to 5,000%, from 100% to 4,000%, from 100% to 3,000%, from 100% to 2,000%, and/or at least from 100% to 1,000% compared to the level of RSV neutralizing antibodies in the first pre-immune subject. An increase of "at least 100%" means at least a doubling. For example, at least a 100% increase in a level of 10 means at least a doubling to a level of at least 20. Data herein in FIG. 1A show about 650% increase to a titer of about 4,500.

Another surprising aspect of the invention's methods, is that the immunized subject comprises an increase in the level of the RSV neutralizing antibodies compared to the level of RSV neutralizing antibodies in a second (e.g., control) pre-immune subject that is infected with RSV. In a particular embodiment, the increase in the level of the RSV neutralizing antibodies in the immunized subject is at least 100%, including at least from 100% to 10,000%, from 100% to 9,000%, from 100% to 8,000%, from 100% to 7,000%, from 100% to 6,000%, from 100% to 5,000%, from 100% to 4,000%, from 100% to 3,000%, from 100% to 2,000%, and/or at least from 100% to 1,000% compared to the level of RSV neutralizing antibodies in the second (e.g., control) pre-immune subject that is infected with RSV. An increase of "at least 100%" means at least a doubling. For example, at least a 100% increase in a level of 10 means at least a doubling to a level of at least 20. Data herein in FIG. 1A show about 650% increase to a titer of about 4,500.

In yet another surprising aspect of the invention's methods, the immunized subject comprises an increase in the level of the RSV neutralizing antibodies compared to the level of RSV neutralizing antibodies in a second (e.g., control) pre-immune subject that is treated with a second composition comprising a control chimeric ND VLP (McGinnes Cullen et al. (2015) J Transl. Med 13:350) (SEQ ID NO:04, FIG. 6B) that contains, in operable combination 1) stabilized post-fusion RSV F protein ectodomain of McLellan et al. (19) (exemplified by SEQ ID NO:08; FIG. 8B), 2) transmembrane domain of NDV F protein (exemplified by SEQ ID NO:10; FIG. 9A), and 3) cytoplasmic domain of NDV F protein (exemplified by SEQ ID NO:12; FIG. 9B), wherein the increase in the level of the RSV neutralizing antibodies in the immunized subject is at least 100%, including at least from 100% to 10,000%, from 100% to 9,000%, from 100% to 8,000%, from 100% to 7,000%, from 100% to 6,000%, from 100% to 5,000%, from 100% to 4,000%, from 100% to 3,000%, from 100% to 2,000%, and/or at least from 100% to 1,000% compared to the second (e.g., control) pre-immune subject that is treated with the second composition. An increase of "at least 100%" means at least a doubling. For example, at least a 100% increase in a level of 10 means at least a doubling to a level of at least 20.

While not intending to limit the level of the neutralizing antibody titer to a particular value, in one embodiment, the immunized subject comprises a titer of at least 700, including at least from 700 to 10,000, from 800 to 10,000, from 900 to 10,000, from 1,000 to 10,000, from 2,000 to 10,000, from 3,000 to 10,000, from 4,000 to 10,000, from 5,000 to 10,000, from 6,000 to 10,000, from 7,000 to 10,000, and/or at least from 9,000 to 10,000. In one particular embodiment, the titer of RSV neutralizing antibodies is about 4,500. FIG. 1 A shows about 650% increase to a titer of about 4,500.

A further surprising aspect of the invention's methods is that the level of the RSV neutralizing antibodies after a single administration of a dose of the first composition to the first pre-immune subject is substantially the same as the level of RSV neutralizing antibodies after twice administering the dose of the first composition to a control naïve subject that has undetectable levels of RSV neutralizing antibodies (FIG. 1A, and FIG. 12A).

While not intending to limit the dosage of the compositions used in the invention's methods, in one embodiment, the immunologically effective amount of the first composition comprises from 1 microgram to 50 micrograms of the chimeric ND VLP (exemplified by SEQ ID NO:02; FIG. 5B), including from 1 to 49, from 1 to 48, from 1 to 47, from 1 to 46, from 1 to 45, from 1 to 44, from 1 to 43, from 1 to 42, from 1 to 41, from 1 to 40, from 1 to 39, from 1 to 38, from 1 to 37, from 1 to 36, from 1 to 35, from 1 to 34, from 1 to 33, from 1 to 32, from 1 to 31, from 1 to 20, from 1 to 19, from 1 to 18, from 1 to 17, from 1 to 16, from 1 to 15, from 1 to 14, from 1 to 13, from 1 to 12, from 1 to 11, from 1 to 10, from 1 to 9, from 1 to 8, from 1 to 7, from 1 to 6, and from 1 to 5 micrograms of the chimeric ND VLP. In a particular embodiment, the immunologically effective amount of the first composition comprises from 4 micrograms to 45 micrograms of the chimeric ND VLP. In a particular embodiment, the immunologically effective amount of the first composition comprises 30 micrograms of the chimeric ND VLP. Data herein show administration of 30 micrograms ND VLP containing approximately 7 micrograms of pre-fusion RSV F protein ectodomain (Example 2, FIG. 1A).

In a further embodiment, the immunologically effective amount of the first composition comprises from 0.1 microgram to 20 micrograms of the chimeric protein (exemplified by SEQ ID NO:06; FIG. 7 B), including from 0.5 to 20, from 1 to 20, from 1 to 19, from 1 to 18, from 1 to 17, from 1 to 16, from 1 to 15, from 1 to 14, from 1 to 13, from 1 to 12, from 1 to 11, and from 1 to 10 of the chimeric protein. In a particular embodiment, the immunologically effective amount of the first composition comprises seven (7) micrograms of the chimeric protein. Data herein show administration of 30 micrograms ND VLP containing approximately 7 micrograms of pre-fusion RSV F protein ectodomain (Example 2, FIG. 1A).

In some embodiments, the immunologically effective composition may be administered more than once to further boost immunity against RSV.

In one embodiment, the invention's methods comprise determining the level of the RSV neutralizing antibodies in any one or more of the subjects described herein (e.g., naïve subject, and/or pre-immune subject, and/or subject treated with one or more of the invention's Pre-F/F VLPs and/or subject treated with Post-F/F VLPs, and/or subject infected with RSV). In particular embodiments, the inventions' methods comprise comparing the levels of the RSV neutralizing antibodies in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

In some embodiments, the method further comprises comparing the level of the RSV neutralizing antibodies in the immunized subject to the level of the RSV neutralizing antibodies in one or more test subjects selected from a) the first pre-immune subject, b) a second (e.g., control) pre-immune subject that is infected with RSV, c) a second (e.g., control) pre-immune subject that is treated with a control second composition comprising a chimeric ND VLP (exemplified by SEQ ID NO:04; FIG. 6B; McGinnes Cullen et al. (2015) J Transl. Med 13:350] that contains, in operable combination 1) stabilized post-fusion RSV F protein ectodomain (19) (exemplified by SEQ ID NO:08; FIG. 8B), 2) transmembrane domain of NDV F protein (exemplified by SEQ ID NO:10; FIG. 9A), and 3) cytoplasmic domain of NDV F protein (exemplified by SEQ ID NO:12; FIG. 9B), wherein detecting an increase in the level of the RSV neutralizing antibodies in the immunized subject compared to the level of the RSV neutralizing antibodies in the one or more test subjects indicates that the immunized subject is immunized against the RSV infection.

In a particular embodiment, the method further comprises detecting in the immunized subject a reduction in one or more of (a) level of RSV infection, (b) one or more symptoms of RSV infection, (c) susceptibility to RSV infection, and (d) transmission of RSV infection, compared to the first pre-immune subject.

In a further embodiment, the invention's methods are carried out under conditions wherein the level of the RSV neutralizing antibodies after a single administration of the invention's Pre-F/F VLPs to the first pre-immune subject is higher than the level of RSV neutralizing antibodies after a single administration of the invention's ND VLPs to a naïve subject, and/or to a pre-immune subject infected with RSV, and/or to a pre-immune subject treated with Post-F/F VLPs. Data herein in Example 10, FIG. 16A-B, demonstrates that a single injection of VLPs into RSV primed mice stimulated much higher NA titers than in naïve mice. Additionally, data herein in Example 10, FIG. 16A-B, demonstrates that in RSV primed animals, (1) A single injection of the invention's Pre-F/F VLPs resulted in 7 and 3.7 fold higher neutralizing antibody titers than post-F/F VLPs (days 128 vs 220, respectively), (2) the invention's Pre-F/F VLPs immunization resulted in 12 and 8 fold higher titers (day 128 vs 220 respectively) than a second RSV Infection and (3) Post-F/F VLPs resulted in 1.8 fold to 2.3 fold higher titers (day 128 vs Day 220) than a second RSV infection. In naïve mice, two injections of the invention's Pre-F/F VLPs resulted in titers approximately 50% that of a single immunization in RSV primed animals.

Data herein in Example 10, FIG. 16A-B also shows that immunization of animals previously infected with RSV (to mimic the vast majority of the human population) with the invention's Pre-F/F VLPs is far superior to immunization with post-F/F VLPs. The absolute levels of neutralizing antibodies stimulated by the invention's Pre-F/F VLPs at day 128 were 7 fold higher than levels stimulated by Post-F/F VLPs.

With respect to antibody durability, immunization of animals previously infected with RSV with the invention's Pre-F/F VLPs is far superior to immunization with post-F/F VLPs in terms of absolute levels of neutralizing antibodies at later times. Thus, in one embodiment, the invention's methods are carried out under conditions wherein the level of the RSV neutralizing antibodies after a single administration of the invention's Pre-F/F VLPs to the first pre-immune subject is higher for at least a period of from about 30 to about 220 days after the single administration than the level of RSV neutralizing antibodies after a single administration of a second Post-F/F VLPs to a second pre-immune subject. Data herein in Example 10, FIGS. 16A-B-18A-B, demonstrates that RSV NA titers are quite stable with time after a single injection of the invention's pre-F/F VLPs. Data herein in Example 10 also shows that because titers after Pre-F/F VLP immunization were 7 fold and 12 fold higher than the titers after Post-F/F VLP or RSV immunization at day 128, the titers after the pre-F/F VLP immunization at day 220 were still much higher than titers after Post-F/F VLP or RSV immunization (3.7 fold and 8 fold).

(C) Anti-F Protein Antibody and Anti-G Protein Antibody

In one embodiment, the invention's methods comprise determining the level of anti-F protein antibody (such as anti-F protein IgG) and/or of anti-G protein antibody (such as anti-G protein IgG) in any one or more of the subjects described herein (e.g., naïve subject, and/or pre-immune subject, and/or subject treated with one or more of the invention's Pre-F/F VLPs and/or subject treated with Post-F/F VLPs, and/or subject infected with RSV). In particular embodiments, the inventions' methods comprise comparing the levels of anti-F protein antibody (such as anti-F protein IgG) and/or of anti-G protein antibody (such as anti-G protein IgG) in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

Figure 13:
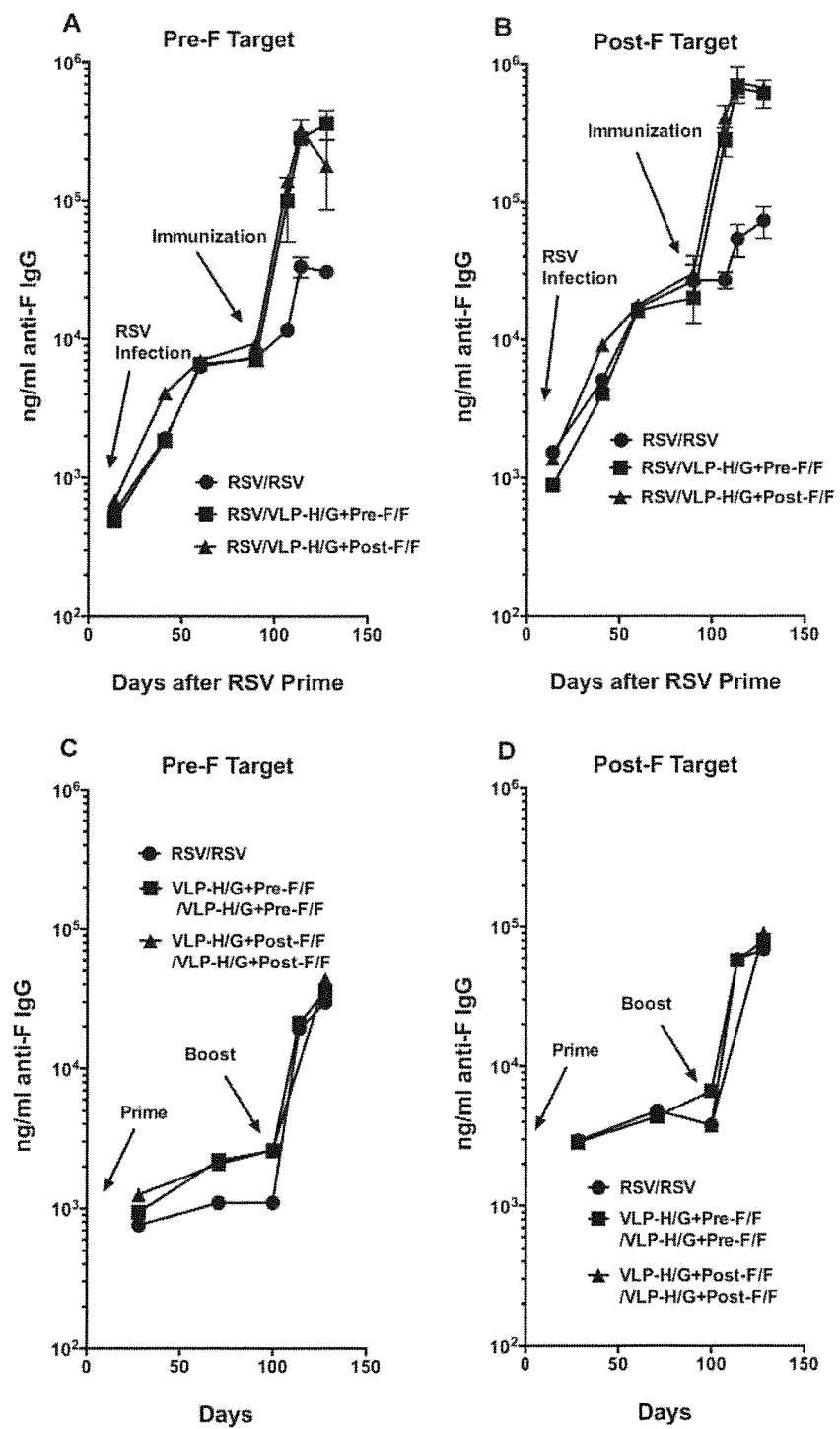
FIG. 13A-D: Total Anti-F Protein Antibody in Animal Sera. Total anti-F protein antibody was measured in ELISA using as target purified soluble pre-fusion F (panels FIGS. 13A and C) or purified soluble post-fusion F protein (panels FIGS. 13B and D). Panels FIGS. 13A and B show ng/ml of anti-F protein IgG at different time points in RSV-experienced animals. Results are the average of two separate determinations. For the pre-F target as well as post-F target the difference at day 128 between RSV/VLP-H/G+Pre-F/F and RSV/VLP-H/G+Post-F/F groups was not significant. For the pre-F target, p value for difference between RSV/VLP-H/G+Pre-F/F and RSV/RSV was 0.030 while the difference between RSV/RSV and RSV/VLP-H/G+Post-F/F immunization was not significant. For the post F target, the p values for differences between RSV/VLP-H/G+Pre-F/F or RSV/VLP-H/G+Post-F/F VLP immunization and RSV/RSV immunization were 0.034 and 0.0011, respectively. Panels FIGS. 13C and D show ng/ml of anti-F protein IgG at different time-points in immunized naïve animals. Figure shows results of one of two determinations with identical results and replicates results previously reported[21]. For the pre-F target or the post-F target the differences in values at day 128 between all groups were not significant.

In a further embodiment, the invention's methods are carried out under conditions wherein the levels of pre-F specific IgG in a pre-immune subject treated with the invention's Pre-F/F VLPs or Post-F/F VLPs is the same but the levels are lower than the levels of post-F specific IgG in a pre-immunized subject treated with Pre-F/F VLPs or Post-F/F VLPs (FIGS. 13A and 13B).

Importantly, FIG. 13A-B shows that even though the IgG titers (specific for pre-F or post-F) are the same after Pre-F/F VLP or Post-F/F VLP immunization of pre-immune animals, nonetheless, the neutralizing antibody titers are quite different (FIGS. 1A-B, 12A-B, 16A-B). This means that the specificities of the antibodies stimulated by the two VLP immunizations are quite different. That is, the Pre-F/F VLPs robustly stimulate neutralizing antibodies, whereas the Post-F/F VLPs do not. This key observation probably explains why all previous vaccine candidates have failed since, until recently, all candidates contained primarily post F protein which stimulated IgG titers but these IgGs were poorly neutralizing.

Data herein in Example 10, FIG. 17A-D shows that a single immunization of RSV primed animals with VLPs resulted in 10 fold higher IgG titers compared to two immunizations with VLPs in naïve animals. Example 10, FIG. 17A-D also shows that a single immunization of RSV primed animals with VLPs resulted in 10 fold higher IgG titers than RSV infections. This shows that total anti-F IgG levels also remained stable with time, and that VLPs stimulated very durable total anti-F IgG antibodies in both RSV primed and naïve animals.

In particular embodiments, the invention's methods comprise using ND VLPs that include, in operable combination, RSV G protein (e.g., RSV G ectodomain). This is exemplified by VLP-H/G+Pre-F/F.

In some embodiments, the invention's methods include measuring the level of antibody that is specific for the RSV G protein (e.g., RSV G ectodomain) in any one or more of the subjects described herein (e.g., naïve subject pre-immune subject, and/or subject treated with one or more of the invention's Pre-F/F VLPs and/or subject treated with Post-F/F VLPs, and/or subject infected with RSV). In particular embodiments, the inventions' methods comprise comparing the levels of antibody that is specific for the RSV G protein (e.g., RSV G ectodomain) in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

Figure 14:
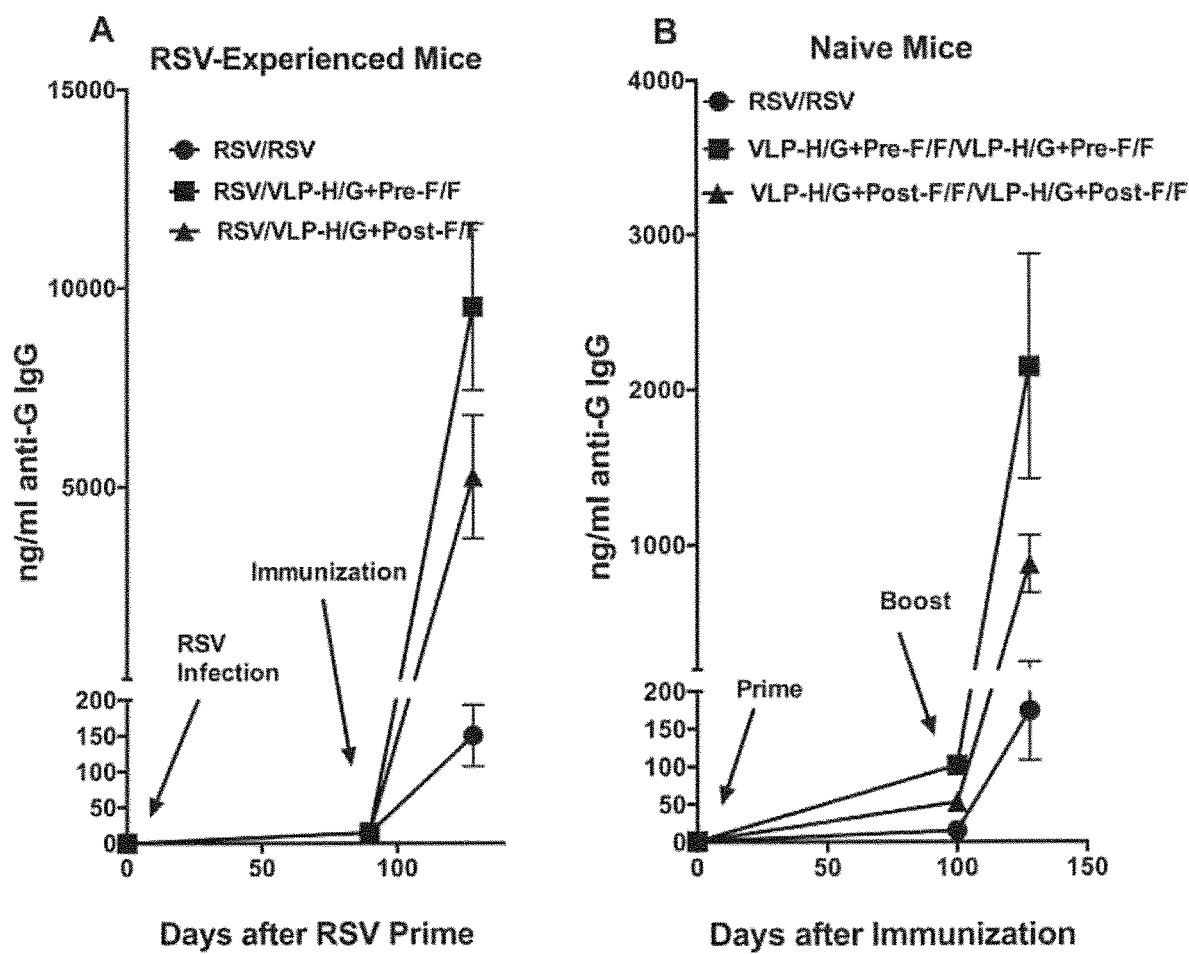
FIG. 14A-B: Total Anti-G Protein Antibody in Animal Sera. Total anti-G protein IgG was measured in ELISA using as target soluble G protein. Panel
Figure 18A:
FIG. 18A-C: Total anti-G protein IgG Titers in (FIG. 18A) RSV primed mice, and (FIG. 18B) naïve mice. Panel
Figure 18B:
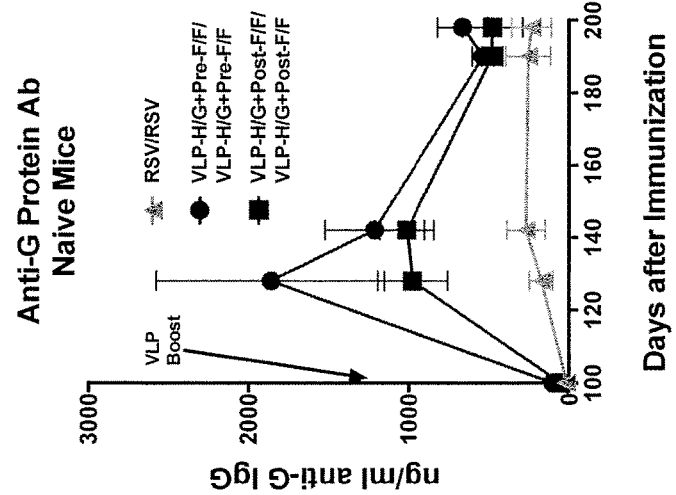
Figure 18C:
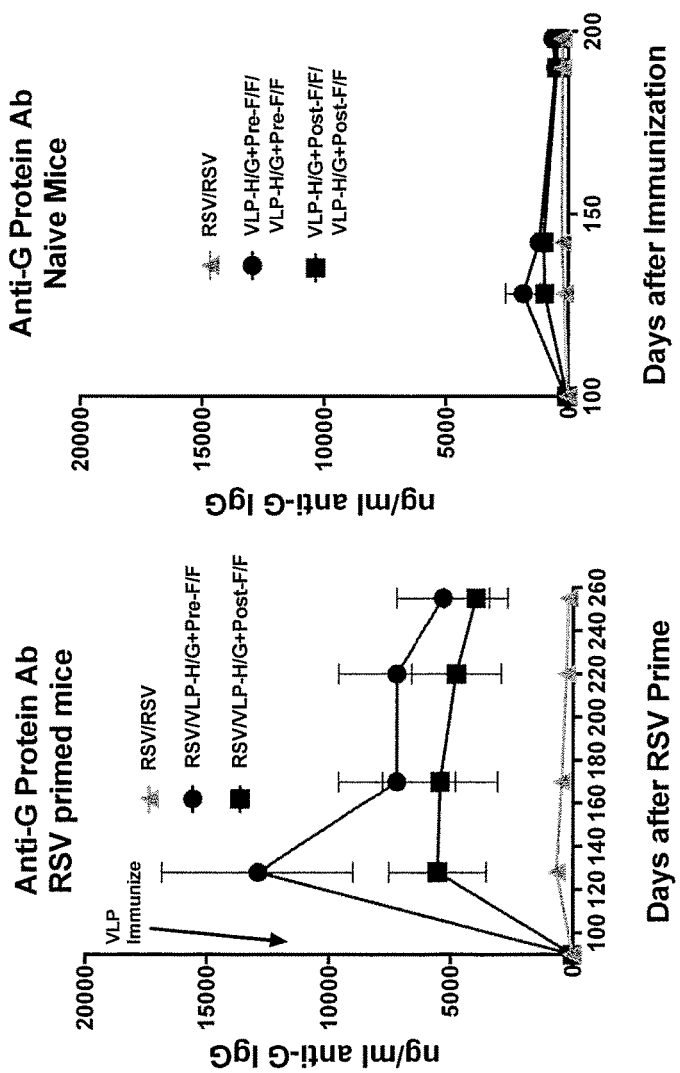

Thus, in one embodiment, the invention's methods are carried out under conditions wherein the level of antibody that is specific for the RSV G protein (e.g., RSV G ectodomain) in a pre-immune subject after a single administration of the invention's Pre-F/F VLPs is higher than the level of antibody that is specific for the RSV G protein (e.g., RSV G ectodomain) in the pre-immune subject prior to the administration step, and/or after a single administration of ND Post-F/F VLPs, and/or in a pre-immune subject infected with RSV, and/or in a naïve subject. For example, data in Example 7, FIG. 14A-B shows that in RSV-experienced animals, a single VLP immunization with either the VLP-H/G+Pre-F/F or the VLP-H/G+Post-F/F considerably increased the anti-G protein antibody titers and this increase was approximately four fold over that stimulated by a prime and boost with either VLP in naïve animals. Also, data in Example 10, FIG. 18A-C, shows that with respect to antibody levels in RSV primed animals: (1) VLPs stimulated 7 fold (the invention's pre-F/F VLPs) and 5 fold (post-F/F VLPs) higher anti-G protein titers than in VLPs in naïve animals, (2) VLPs stimulated 65 fold (pre-F VLPs) and 25 fold (post-F/F VLPs) higher anti-G protein antibody titers than two consecutive RSV infections, and (3) Pre-F VLPs stimulated 2.6 fold higher anti-G protein antibody titers than post-F VLPs. Importantly, these differences in anti-G antibody levels show that the presence of the pre-F protein in the invention's Pre-F/F VLP has a significant influence on levels of immune responses to the G protein, which is a protein that a role in protective responses to RSV.

In a particular embodiment the inventions methods are carried out under conditions wherein a single administration of the invention's ND VLP that comprises RSV G protein (e.g., RSV G ectodomain) to a first pre-immune mammalian subject increases the level of anti-G protein antibody compared to the level of anti-G protein antibody in a second pre-immune subject that is immunized with a second composition comprising chimeric ND Post-F/F VLPs. Data herein in Example 7, FIG. 14A-B, shows the surprising result that the levels of anti-G protein antibodies after a single VLP immunization of RSV-experienced animals or after a VLP prime and boost of naïve animals were significantly different depending upon the VLP used although both VLPs contained similar amounts of the same H/G protein (FIG. 10A-D, panels FIG. 10A and FIG. 10D). VLPs containing the pre-fusion F protein simulated significantly higher titers of anti-G protein antibody than the VLPs containing the post-F protein.

In one embodiment, the invention's methods comprise determining the RSV titer in lungs after RSV challenge in any one or more of the subjects described herein (e.g., naïve subject, and/or pre-immune subject, and/or subject treated with one or more of the invention's Pre-F/F VLPs and/or subject treated with Post-F/F VLPs, and/or subject infected with RSV). In particular embodiments, the inventions' methods comprise comparing the RSV titer in lungs in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

Figure 15:
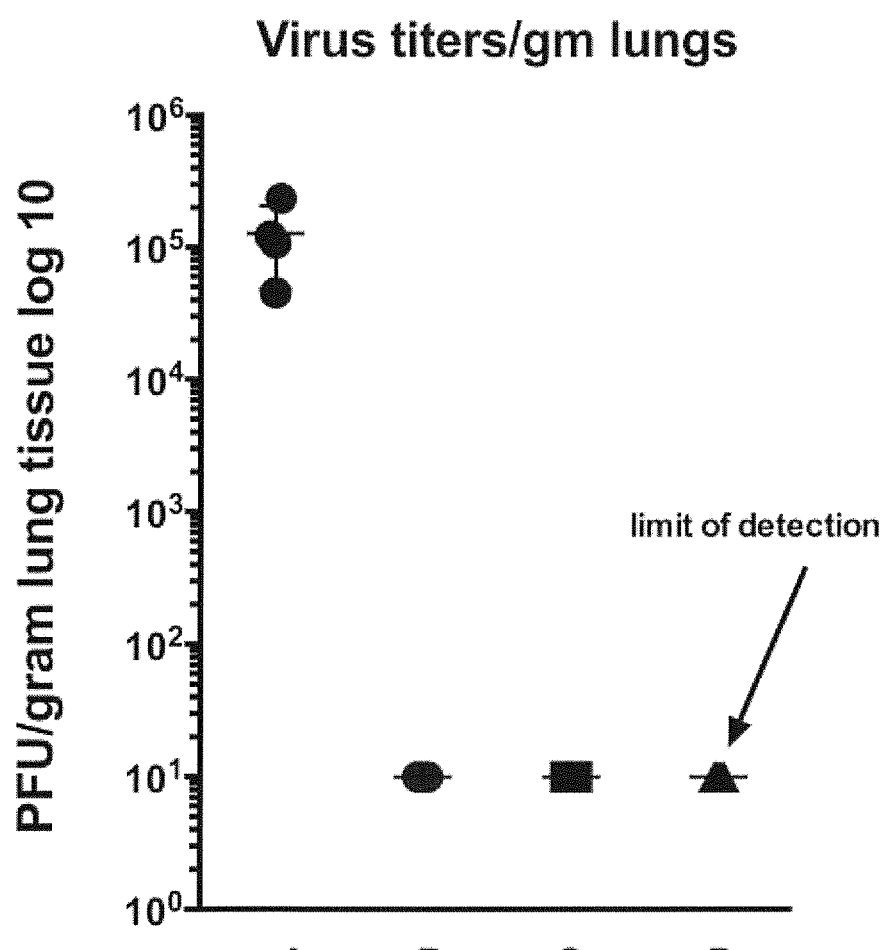
FIG. 15: Protection from Challenge. Shown are lung titers after challenge of RSV-experienced VLP immunized animals. RSV challenge was 125 days after VLP immunization. A: no RSV prime, no immunization; B: RSV primed, RSV immunized; C: RSV primed, VLP-H-G+Pre-F/F immunized; D: RSV primed, VLP-H/G+Post-F/F immunized. Each group contained five animals and titers of each animal are shown in the graph. The p value for the differences between group A and the other groups is 0.0182.

In a particular embodiment, the methods of the invention are carried out under conditions wherein the pre-immune subject that is immunized with the invention's Pre-F/F VLPs has a lower RSV titer in lungs than a naïve subject to which the invention's Pre-F/F VLP have not been administered. Data herein in Example 8, FIG. 15, show that while RSV titers were obtained in the lungs of unprimed, unimmunized controls (lane A), no virus was detected at the limits of detection in lungs of immunized animals. These results demonstrate that immunization of primed animals with the invention's Pre-F/F VLP protected them from RSV replication.

(D) Spleen Memory B Cells

In one embodiment, the invention's methods comprise determining the level of splenic memory B cells in any one or more of the subjects described herein (e.g., naïve subject, and/or pre-immune subject, and/or subject treated with one or more of the invention's Pre-F/F VLPs and/or subject treated with Post-F/F VLPs, and/or subject infected with RSV). In particular embodiments, the inventions' methods comprise comparing the levels of level of splenic memory B cells in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

Thus, in one embodiment, the invention's methods are carried out under conditions wherein the level of splenic memory B cells in a pre-immune subject that is immunized with the invention's Pre-F/F VLPs is higher than the level of splenic memory B cells in a pre-immune subject that is immunized with Post-F/F VLPs. Data herein in Example 11, FIG. 19A-B demonstrates that pre-F/F protein in VLPs stimulated higher levels of splenic memory B cells than post-F/F VLPs in RSV experienced animals.

In another embodiment, the invention's methods are carried out under conditions wherein the level of splenic memory B cells in a pre-immune subject that is immunized with the invention's Pre-F/F VLPs is higher than the level of splenic memory B cells after RSV infection of a pre-immune subject and/or after RSV infection of a naïve subject. Data herein in Example 11, FIG. 20 A-B, shows that the invention's Pre-F/F VLPs stimulated higher levels of splenic memory B cells than RSV in RSV experienced animals as well as naïve mice.

(E) Avidity

In one embodiment, the invention's methods comprise determining the level of avidity of the RSV anti-F or G IgG antibodies in any one or more of the subjects described herein (e.g., naïve subject, and/or pre-immune subject, and/or subject treated with one or more of the invention's Pre-F/F VLPs and/or subject treated with Post-F/F VLPs, and/or subject infected with RSV). In particular embodiments, the inventions' methods comprise comparing the levels of avidity of the RSV antibodies in any two or more of the subjects described herein (e.g., naïve subject, and/or pre-immune subject, and/or subject treated with one or more of the invention's Pre-F/F VLPs and/or subject treated with Post-F/F VLPs, and/or subject infected with RSV).

In one embodiment, the invention's methods are carried out under conditions wherein the avidity of the RSV antibodies in a pre-immune subject immunized with the invention's Pre-F/F VLPs is higher than avidity of RSV antibodies in a pre-immune subject infected with RSV. Data herein in Example 12, FIGS. 22A-B show that avidity of the pre-F specific antibodies stimulated by VLPs is higher than the avidity of antibodies stimulated by two RSV infections, i.e., VLP Stimulated antibodies are 2 fold more resistant to 3 M urea than RSV stimulated antibodies. Also, FIGS. 22A and B show that in RSV primed animals, the invention's Pre-F/F VLPs stimulated higher avidity antibodies than Post-F/F VLPs, i.e., the invention's Pre-F/F VLP stimulated antibodies are 1.7 fold more resistant to 7 M urea than Post-F/F VLP stimulated antibodies."

In a particular embodiment, the invention's methods are carried out under conditions wherein the avidity of the anti-G protein antibody in the pre-immunized subject that is treated with the invention's Pre-F/F VLPs is higher than the avidity of anti-G protein antibody in a pre-immune mammalian subject infected with RSV. Data herein in Example 12, FIG. 21C shows that the invention's pre-F/F VLPs stimulated higher avidity anti-G protein antibodies than RSV infections.

EXPERIMENTAL

The following examples serve to illustrate certain preferred embodiments and aspects of the present invention and are not to be construed as limiting the scope thereof.

EXAMPLE 1

Materials and Methods

A. Cells, virus, plasmids

ELL-0 (avian fibroblasts) (CLR-12203), Vero cells (CLR-1586), COS-7 cells (CLR-1651), and Hep2 cells (CCL-23) were obtained from the American Type Culture Collection. Expi293F cells were obtained from ThermoFisher/Invitrogen (A14527). ELL-0 cells, Vero cells, COS-7 cells, and Hep2 cells were grown in DMEM (Invitrogen 1195-073) supplemented with penicillin, streptomycin (Invitrogen 15140-122), and 5% (Vero cells) or 10% fetal calf serum (Invitrogen 10437-028). Expi293F cells were grown in Expi293 media (ThermoFisher/Gibco/Invitrogen A1435101). RSV, A2 strain, was obtained from Dr. Robert Finberg.

VLPs containing the RSV F and G proteins were formed with the Newcastle disease virus (NDV) core proteins NP and M[18,33] and contain the NDV HN/RSV G Amino Acid Sequence (SEQ ID NO:16) (FIG. 24B) encoded by the NDV HN/RSV G DNA Sequence (SEQ ID NO:15) (FIG. 24A). The cDNAs encoding the NDV NP and M protein have been previously described[34]. The RSV F and G proteins are incorporated into these VLPs by constructing chimera protein genes composed of ectodomains of the G or F glycoproteins fused to the transmembrane (TM) and cytoplasmic (CT) domains of the NDV HN protein or NDV F glycoprotein, respectively. These NDV domains specifically interact with the NDV NP and M protein resulting in efficient incorporation of the chimera proteins into VLPs.

The construction, expression, and incorporation of the chimera protein NDVHN/RSVG (H/G) into VLPs have been previously described[19]. The construction, expression, and incorporation into VLPs of the stabilized pre-fusion F protein (Pre-F/F DS-Cav1) to generate VLP-H/G+Pre-F/F, and the stabilized post-fusion F protein (Post-F/F) to create VLP-H/G+Post-F/F have been previously described[21].

The construction of genes encoding the soluble pre-F protein, the soluble post-F protein, and the soluble G protein used for target in ELISA was previously described[21].

B. Polyacrylamide Gel Electrophoresis, Silver Staining, and Western Analysis

Proteins were resolved on 8% Bis-Tris gels (NuPage, ThermoFisher/Invitrogen WB1001/WG1002)). Silver staining of proteins in the polyacrylamide gels was accomplished as recommended by the manufacturer (ThermoFisher/Pierce 24600). Quantification of NP, M, different forms of F/F, H/G protein, and soluble pre-F, post-F, and soluble G was accomplished after their separation in polyacrylamide gels followed by silver staining or by Western blots of the proteins as well as protein standards as previously described[35,36]. For Western analysis, proteins in the polyacrylamide gels were transferred to PVDF membranes using dry transfer (iblot, ThermoFisher/Invitrogen iB401001). Proteins were detected in the blots using anti-RSV HR2 peptide antibody or anti-RSV antibody.

C. Antibodies

RSV F monoclonal antibody clone 131-2A (Millipore MAB8599) was used in RSV plaque assays. Monoclonal antibody (mAb) 1112, mAb 1200, mAb 1243, were generous gifts of Dr. J. Beeler[37] and used to verify F protein conformations, and mAb D25 and mAb motavizumab, generous gifts of Dr. J. McLellan,[14] were used for ELISA analysis of VLPs and soluble F proteins. Anti-RSV F protein HR2 antibody used for Western Blots is a polyclonal antibody specific to the HR2 domain of the RSV F protein[18]. Anti-RSV G protein antibody is a polyclonal antibody raised against a peptide containing G protein amino acids 180-198 (ThermoFisher PAS-22827). Secondary antibodies against goat (A5420), mouse (A5906) and rabbit IgG (A0545) were purchased from Sigma.

D. VLP Preparation, Purification, and Characterization

For preparations of VLPs to be used as immunogens (VLP-H/G+Pre-F/F, VLP-H/G+Post-F/F), ELL-0 cells growing in T-150 flasks were transfected with cDNAs encoding the NDV M protein, NP, the chimeric proteins H/G, and either Pre-F/F or Post-F/F as previously described[18,19]. At 24 hours post-transfection, heparin (Sigma, H4784) was added to the cells at a final concentration of 10 μg/ml[19] to inhibit rebinding of released VLPs to cells. At 72, 96, and 120 hours post-transfection, cell supernatants were collected and VLPs purified by sequential pelleting and sucrose gradient fractionation as previously described[18,19,35]. Concentrations of proteins in the purified VLPs were determined by silver-stained polyacrylamide gels and by Western analysis using marker proteins for standard curves[18,35]. The conformation of F protein in the VLP preparations was verified by reactivity to mAbs.

E. Preparation of Soluble F Proteins

Expi293F cells were transfected with pCAGGS vector containing sequences encoding the soluble pre-F protein or the soluble post-F protein. At five to six days post transfection, total cell supernatants were collected and cell debris removed by centrifugation. Pre-fusion and post-fusion polypeptides were then purified on columns using the His tag and then the strep tag as previously described[15].

F. Quantification of Soluble F Protein and VLP Associated F Protein

Determinations of amounts of RSV F protein in VLPs or in soluble F protein preparations were accomplished by Western blots using anti-HR2 antibody for detection and comparing the signals obtained with a standard curve of purified F proteins as previously described[35]. Quantification of amounts of soluble G protein was determined on Western blots using anti-RSV G protein antibody for detection.

G. Preparation of RSV, RSV Plaque Assays, and Antibody Neutralization

RSV was grown in Hep2 cells[18,19], and RSV plaque assays were accomplished on Vero cells as previously described[21]. Antibody neutralization assays in a plaque reduction assay have been previously described[21,22]. Neutralization titer was defined as the reciprocal of the dilution of serum that reduced virus titer by 50%.

H. Animals, Animal Immunization, and RSV Challenge

Mice, 4-week-old female BALB/c, from Taconic laboratories (BALB-F), were housed (groups of 5) under pathogen-free conditions in microisolator cages at the University of Massachusetts Medical Center animal quarters. Female mice were used in order to assess the potential of VLPs for maternal immunization. Protocols requiring open cages were accomplished in biosafety cabinets. BALB/c mice were immunized by intramuscular (IM) inoculation of 30 μg total VLP protein (5 microgram (μg) F protein) in 0.05 ml of THE (50 mM Tris-HCl, pH 7.4, 150 mM NaCl, 5 mM EDTA) containing 10% sucrose. For infections with RSV, the animals were lightly anesthetized with isoflurane and then infected by intranasal (IN) inoculation of 50 microliter (μl) of RSV ($1 \times 10^7$ pfu/ml). All animal procedures and infections were performed in accordance with the University of Massachusetts Medical School IACUC and IBC approved protocols.

I. ELISA Protocols

For determination of anti-F protein or anti-G protein serum antibody titers, blood was obtained from immunized animals by tail vein nicks and centrifuged in BD microtainer serum separator tubes (ThermoFisher 365967) to remove blood cells. For ELISA, wells of microtiter plates (ThermoFisher/Costar 2797) were coated with either purified soluble pre-fusion F protein, soluble post-fusion F protein, or soluble G protein and incubated for 24 hours at 4° C. Wells were then incubated in PBS-2% BSA for 16 hours. Different dilutions of sera, in 0.05% Tween and 2% BSA, were added to each well and incubated for 2 hours at room temperature. After six washes in PBS, sheep anti-mouse antibody coupled to HRP (Sigma A5906) was added in 50 μl PBS-2% BSA and incubated for 1.5 hours at room temperature. Bound HRP was detected by adding 50 μl TMB (3,3'5,5'-tetramethylbenzidin, ThermoFisher 34028) and incubating for 5-20 minutes at room temperature until blue color developed. The reaction was stopped with 50 μl 2N sulfuric acid. Color was read in SpectraMax Plus Plate Reader (Molecular Devices) using SoftMax Pro software. Amounts of IgG bound to the wells was calculated using a standard curve generated using defined amounts of purified IgG[38].

J. Statistical Analysis

Statistical analyses (student T test) of data were accomplished using Graph Pad Prism 6 software.

EXAMPLE 2

Neutralizing RSV Antibody is Stimulated by ND VLPs Containing Stabilized RSV Pre-F/F Protein The materials and methods for cells, viruses, plasmids, preparation of soluble forms of the pre-fusion and post-fusion F proteins and G protein, antibodies, polyacrylamide e gel electrophoresis, silver staining, western analysis, VLP preparation, VLP purification, VLP characterization, ELISA protocols, preparation of RSV, RSV plaque assays, antibody neutralization, animals, animal immunization, RSV challenge, lung and nose viral titration, pulmonary histopathology, and statistical analysis, are previously described (36).

A schematic of testing VLP immunogenicity as a Vaccine in an animal (exemplified by mouse) is shown in FIG. 4. Briefly, mice were immunized with ND VLPs containing stabilized RSV pre-F/F protein operably fused to the foldon sequence (SEQ ID NO:14, FIG. 9C). The stabilized pre-fusion RSV F protein ectodomain was previously described by McLellan et al. (19) and shown in FIG. 3. The RSV pre-F/F chimera protein contains RSV pre-F protein ectodomain operably linked to both the NDV F protein transmembrane (TM) domain and the NDV F protein cytoplasmic (CT) domain FIG. 3).

Figure 3:
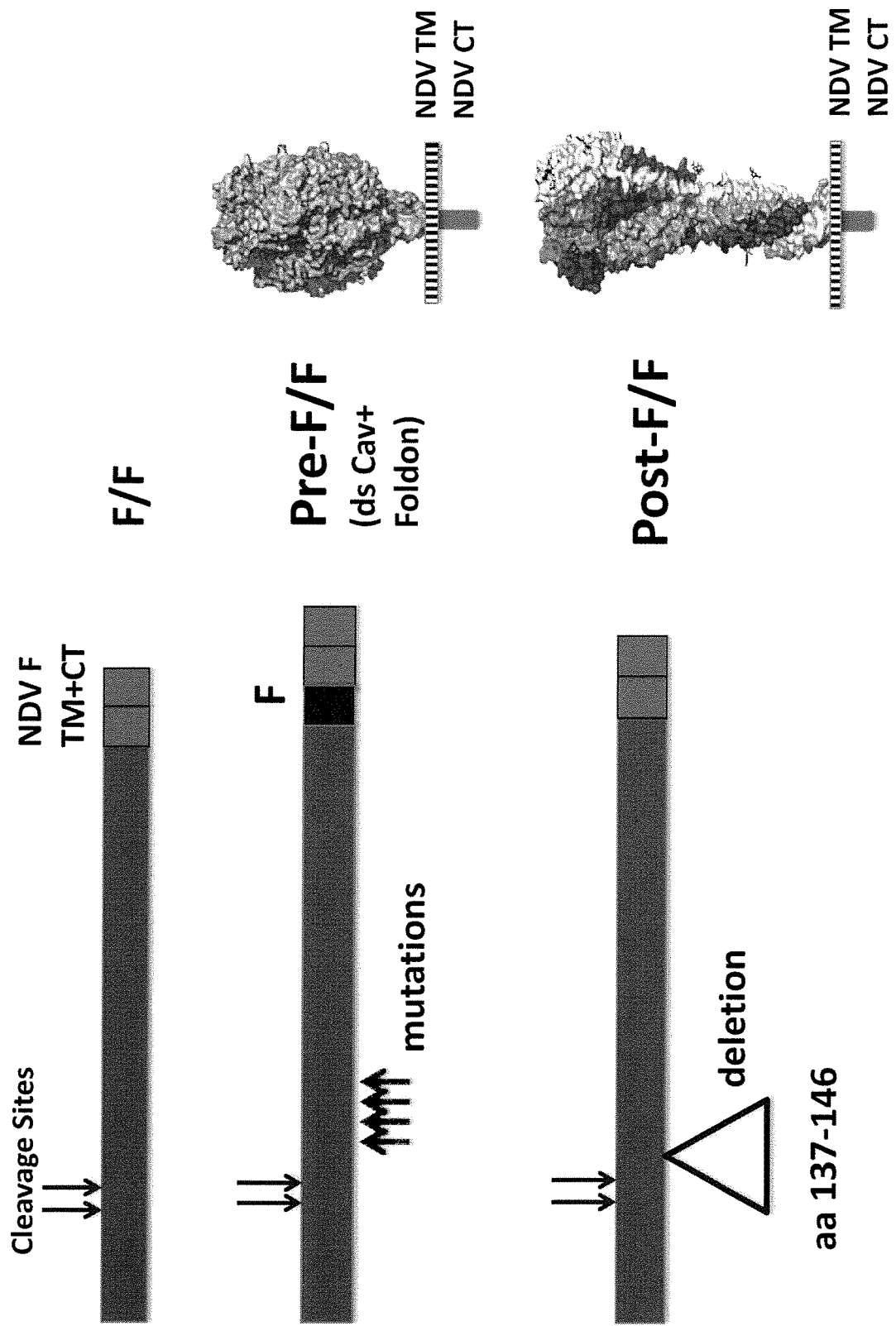
FIG. 3: Alterations of the RSV F Protein Ectodomain (McLellan, et al Science 340:1113 (2013), Swanson et al PNAS 108:9619 (2011)).

ND VLPs containing stabilized RSV pre-F/F protein operably fused to the foldon sequence (SEQ ID NO:02, FIG. 5B) were constructed as previously described (34, 36) (FIG. 3).

FIGS. 1 A-B and 12 A-B show that VLPs with the appropriate conformation of F protein can stimulate high titers of neutralizing antibodies in the presence of preexisting immunity: FIG. 1A and FIG. 12A, shows that, in RSV pre-immune animals, pre-F/F VLPs stimulated neutralizing antibodies titers significantly higher than VLPs containing the post-F/F protein or a second RSV infection. Previously reported results (34) of immunization of naïve animals, after a prime and a prime-boost with pre-F/F VLPs, post-F/F VLPs, or RSV is shown in FIG. 1B and FIG. 12B, for comparison.

In the experiment with pre-immune animals (FIG. 1A-B and FIG. 12A-B, left panel FIG. 12A), groups of 5 mice were infected with RSV by intranasal inoculation (FIG. 4). Ninety-five days later, one group was immunized with Pre-F/F VLPs, another group immunized with Post-F/F VLPs, and a third group given a second infection with RSV. The results show the following: First, in RSV pre-immune animals (left panel A), pre-F/F VLPs stimulated significantly higher neutralizing Ab titers than post-F/F VLPs or RSV. Importantly, that is, pre-F/F VLPs can stimulate high titers of neutralizing antibodies in the presence of pre-existing immunity to RSV.

Second, post-F/F VLPs stimulated slightly higher titers than a second RSV infection.

Third, the titers after a single pre-F/F VLP immunization of pre-immune mice were comparable to titers in sera of naïve mice after a prime and a boost with pre-F/F VLPs (titers of 4500-right panel B) (34), suggesting the pre-F/F VLPs stimulated memory responses in the RSV-pre-immune animal. However, the post-F/F VLP immunization of pre-immune mice stimulated titers more comparable to titers after single post-F/F immunization of naïve mice (titers of 600 vs 150) rather than titers obtained after a prime and boost immunization with post-F/F VLPs (titers of 2700, FIG. 1A-B, right panel FIG. 1B).

In conclusion, these results show that the pre-F/F VLPs should be a very effective vaccine for RSV pre-immune individuals, who make up most of the human population.

EXAMPLE 3

Characterization of Protein Content of VLP Stocks

VLPs, based on Newcastle disease virus (NDV) core proteins and containing the RSV G protein (e.g., RSV G ectodomain) and either the pre-fusion or post-fusion forms of the RSV F protein, were generated by transfection of ELL-0 cells with plasmids encoding NDV M protein, NDV NP, the H/G chimera protein[19], and either the Pre-F/F or the Post-F/F chimera proteins to generate stocks of VLP-H/G+Pre-F/F or VLP-H/G+Post-F/F[21]. The protein content of the two purified VLP preparations was quantified by Western blots and antibody binding to the purified VLPs. FIG. 10A-D, panel FIG. 10A, shows a Western blot of proteins in the two VLP preparations probed with anti-RSV F (lanes 1 and 2) or anti-RSV G antibodies (lane 3 and 4). The results show that stocks of the two VLPs had equivalent levels of Pre-F/F and Post-F/F chimera proteins and equivalent levels of the H/G chimera protein. The two F protein chimeras are different sizes since the Pre-F/F contains the inserted foldon sequence and the Post-F/F chimera has a deletion of nine amino acids. The H/G chimera protein resolves into heterogeneous species due to inefficient glycosylation of the RSV G protein sequences as previously described[19,21]. To further verify protein concentrations in VLPs, a monoclonal antibody that will bind either form of the RSV F protein, motavizumab[13,23], binds equally to the two VLPs (FIG. 10A-D, panel FIG. 10B) verifying that the two VLPs have assembled equivalent levels of F protein. However, a monoclonal antibody specific for site Φ present only in the pre-fusion form of F protein but not in the post fusion form[14] binds only VLP-H/G+Pre-F/F and not VLP-H/G+Post-F/F (FIG. 10A-D, panel FIG. 10C), a result verifying the conformation of the pre-F protein and the post-F protein in the two VLPs. A polyclonal antibody raised against a G protein derived peptide bound equivalently to two different concentrations of the two VLPs (FIG. 10A-D, panel FIG. 10D) verifying that the two VLPs have the same amount of H/G chimera protein.

EXAMPLE 4

Infection and Immunization

Figure 11A:
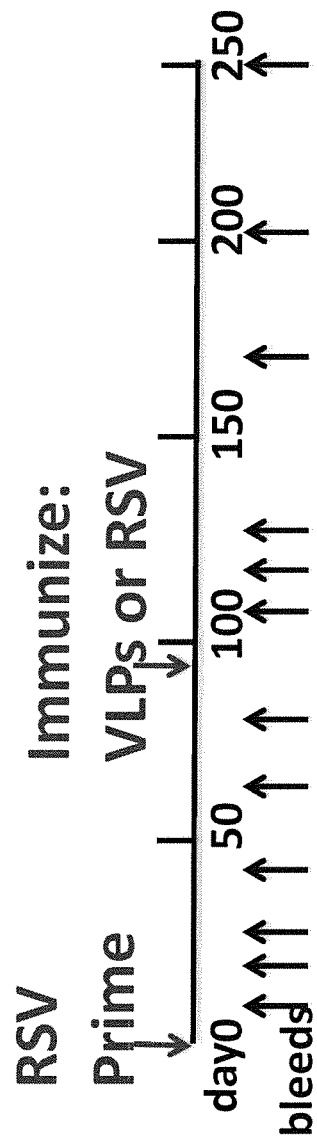
FIG. 11A-B: Immunization/Infection Timelines. Panel FIG. 11 A shows timing of infection of animals with RSV (day 0) and their subsequent immunization with VLPs (day 95) or a second RSV infection (day 95). Sera were harvested from each animal at times indicated by arrows pointing upwards. Panel
Figure 11B:
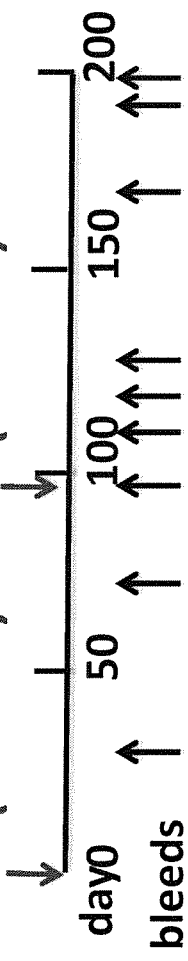

To assess the generation of neutralizing antibody responses in mice previously infected with RSV, three groups of five mice were prepared by infection with RSV by intranasal inoculation. After ninety-five days, one group was immunized with VLP-H/G+Pre-F/F, another group immunized with VLP-H/G+Post-F/F, and a third group was infected a second time with RSV (FIG. 11A). To directly compare responses in previously infected mice with those in naïve mice, in parallel, groups of five naïve mice were immunized in a prime (day 0) and a boost (day 100) with the VLP-H/G+Pre-F/F, with the VLP-H/G+Post-F/F, or RSV infection (FIG. 11B). Serum samples were obtained from each mouse at different times starting at day 0.

EXAMPLE 5

Neutralization Titers in Previously Infected and Naïve Animals

To determine the effect of previous RSV infection on generation of neutralizing antibodies (NA), the neutralization titers in pooled sera of mice at different times after an RSV prime and VLP immunization were determined using an in vitro plaque reduction assay (FIG. 12A-B, panel FIG. 12A). A single injection of these RSV-experienced animals with VLP-H/G+Pre-F/Fs stimulated significantly higher NA titers than VLP-H/G+Post-F/Fs or a second RSV infection. VLP-H/G+Pre-F/F immunization resulted in titers of approximately 4000 by day 128 while VLP-H/G+Post-F/Fs stimulated NA titers of approximately 600 at day 128, only slightly higher than a second RSV infection.

FIG. 12A-B, panel FIG. 12B, illustrates, in parallel groups of naïve mice, the neutralization titers in animals after a prime and after a boost with the either VLP-H/G+ Pre-F/Fs, VLP-H/G+Post-F/Fs, or after one or two RSV infections. These results are very similar to results previously reported for VLP immunization of naïve animals[21]. In a prime immunization, the VLP-H/G+Pre-F/Fs stimulated significantly higher titers than the VLP-H/G+Post-F/Fs or a single RSV infection. A boost with VLP-H/G+Pre-F/Fs increased titers to approximately 4000 while a VLP-H/G+ Post-F/Fs boost resulted in titers of approximately 2500. Two consecutive RSV infections produced NA titers of approximately 200.

EXAMPLE 6

Total Anti-F IgG Titers after Immunization of RSV-Experienced Animals

To determine if the differences in the NA titers after a single immunization of RSV-experienced mice with VLP-H/G+Pre-F/Fs or VLP-H/G+Post-F/Fs could be accounted for by differences in total anti-F protein antibody, the amounts of total anti-F protein IgG in the sera of the two groups were determined at each time point and compared to IgG levels in RSV infected mice. The titers of anti-F protein IgG that bind to the soluble pre-fusion F protein are shown in FIG. 13A-D, panels FIG. 13A, while the binding of serum IgG to the soluble post-fusion F protein is shown in panel FIG. 13B. The results show that a single immunization with VLP-H/G+Pre-F/Fs or VLP-H/G+Post-F/Fs stimulated virtually equivalent titers of IgG specific for soluble pre-fusion F protein or soluble post-fusion F protein. A second RSV infection did stimulate anti-F protein IgG but the levels were 10 fold lower than those stimulated by both VLPs. Thus different levels of total anti-F protein IgG cannot account for the differences in NA titers after immunization with the VLP-H/G+Pre-F/Fs or VLP-H/G+Post-F/Fs.

The IgG levels specific for pre-F and post-F targets generated in naïve mice after a prime VLP immunization and after a boost immunization are shown in FIG. 13A-D, panels FIGS. 13C and D, respectively. Levels of IgG specific to the pre-F target are lower than those specific to the post-F target after immunization with either VLP. Interestingly, the levels of IgG specific to both pre-F and post-F targets after a prime and boost are approximately ten fold lower than levels generated after RSV priming and a single VLP immunization.

EXAMPLE 7

Total Anti-G Protein IgG Titers after Immunization of RSV-Experienced or Naïve Animals Antibodies specific for the RSV G protein also have a role in protective responses to RSV infection[24-27]. Thus it was of interest to determine the influence of previous RSV infection on generation of anti-G protein antibodies. The titers of anti-G protein IgG antibodies in the parallel sets of naïve and RSV-experienced mice were determined using soluble G protein as target in ELISA. FIG. 14A-B, panel FIG. 14A, shows antibody titers in sera after VLP-H/G+Pre-F/F or VLP-H/G+Post-F/F immunization of RSV-experienced mice while panel B shows titers after a prime and a boost of naïve mice with VLP-H/G+Pre-F/Fs or VLP-H/G+Post-F/Fs or RSV. In both naïve and RSV-experienced mice, anti-G protein antibody levels were extremely low after a single RSV infection or after a single VLP immunization. A second RSV infection in both sets of mice only minimally stimulated anti-G protein antibody levels. In contrast, VLP prime and boost immunization of naïve mice substantially increased anti-G protein antibody titers. Importantly, in RSV-experienced animals, a single VLP immunization with either the VLP-H/G+Pre-F/F or the VLP-H/G+Post-F/F considerably increased the anti-G protein antibody titers and this increase was approximately four fold over that stimulated by a prime and boost with either VLP in naïve animals.

A surprising result was that the levels of anti-G protein antibodies after a single VLP immunization of RSV-experienced animals or after a VLP prime and boost of naïve animals were significantly different depending upon the VLP used although both VLPs contained similar amounts of the same H/G protein (FIG. 10A-D, panels FIGS. 10A and D)[21]. VLPs containing the pre-fusion F protein simulated significantly higher titers of anti-G protein antibody than the VLPs containing the post-F protein.

EXAMPLE 8

Protection from RSV Challenge

To determine if a single VLP immunization of RSV-experienced animals could protect them from RSV replication in lungs after RSV challenge, mice were challenged with RSV 125 days after VLP immunization. FIG. 15 shows titers of virus in lung homogenates. While good titers were obtained in the unprimed, unimmunized controls (lane A), no virus was detected at the limits of detection in lungs of immunized animals. The results demonstrated that immunization with either VLP of RSV primed animals protected them from RSV replication.

Results of the challenge of naïve, immunized mice have been previously published[21].

EXAMPLE 9

Discussion of Results in Examples 3-15

The goal of the experiments in Examples 1-15 was to mimic human populations by assessing immune responses to the instant invention's VLP vaccines in mice previously infected with RSV.

When comparing NA titers, the data showed that in animals previously infected with RSV, a single immunization with VLP-H/G+Pre-F/Fs stimulated significantly higher NA titers than a single immunization with VLP-H/G+Post-F/Fs or a second RSV infection. The NA titers after a single VLP-H/G+Pre-F/F immunization of previously infected mice were comparable to titers in sera of naïve mice only after both a prime and a boost with VLP-H/G+Pre-F/Fs. This result suggests that RSV infection does induce potent neutralizing antibody memory responses that can be activated by the VLP-H/G+Pre-F/F immunization but not by VLP-H/G+Post-F/Fs or a second RSV infection.

A recent paper from Gilman, et al[29] supports the idea that RSV infection induces pre-F memory cells, and shows that RSV infection does indeed induce significant levels of memory B cells that encode high titer neutralizing antibodies, at least in humans. Data herein show that RSV infection can induce protective memory in mice but a subsequent infection cannot activate these memory B cells.

In contrast to results with VLP-H/G+Pre-F/Fs, a single immunization with VLP-H/G+Post-F/F in RSV infected mice resulted in NA titers more similar to those observed after a single VLP-H/G+Post-F/F immunization of naïve mice. However, a prime/boost immunization of naïve mice with VLP-H/G+Post-F/Fs stimulated good NA titers, titers that were approximately 50% that simulated by VLP-H/G+Pre-F/Fs. That the VLP-H/G+Post-F/F immunization in RSV-experienced mice did not stimulate these higher NA titers suggests that the RSV infection may not induce memory responses to some determinants present in the VLP-H/G+Post-F/Fs preventing high NA titers with a single VLP-H/G+Post-F/F immunization.

Thought it was possible that differences in NA titers after VLP-H/G+Pre-F/F or VLP-H/G+Post-F/F immunization of RSV-experienced mice were due to differences in total levels of anti-F protein antibodies in sera of the animals, data herein, however, clearly demonstrated that the levels of total anti-F protein antibodies in animals immunized with VLP-H/G+Pre-F/Fs were virtually identical to levels of total antibodies in VLP-H/G+Post-F/F immunized animals. Thus the differences in NA titers in the VLP-H/G+Pre-F/F and VLP-H/G+Post-F/F immunized, RSV-experienced animals must be due to qualitative differences between the populations of anti-F protein antibodies in the two groups of animals. Immunization of RSV-experienced mice with either VLP did result in much higher anti-F protein antibody titers than a second RSV infection indicating that a second RSV infection very poorly activates secondary antibody responses in contrast to the VLP immunization. It is noteworthy that naïve mice have total IgG anti-F protein levels after a prime and boost with VLPs similar to that observed after RSV infection. However, total antibody levels by day 128 in these naïve mice were approximately ten fold lower than total levels in the VLP immunized RSV-experienced mice.

Studies of protective immune responses to RSV have largely focused on the role of the F protein. However, antibodies to G protein do have a role in protection from RSV induced disease. The G protein central region contains a conserved sequence that is a mimic of the chemokine CX3C (fractalkine).[27] The G protein competes for the binding of CX3C to its receptor, CX3CR1, inhibiting immune responses to RSV in a number of ways that enhance the pathology of the infection[27,31] [26]. Antibodies to the G protein CX3C sequence block G protein binding to the CX3CR1 moderating RSV disease. Importantly, antibody to this CX3C sequence decrease enhanced respiratory disease that results from RSV challenge of FI-RSV vaccinated animals[32]. Treatment with mAb to CX3C sequence decreased symptoms in RSV infected mice[25]. For these reasons, levels of total anti-G protein IgG in naïve mice immunized with VLPs or infected with RSV were compared to levels of these antibodies in RSV-experienced mice after VLPs immunization or a second RSV infection. Data herein show that in naïve mice a single RSV infection or one VLP immunization (prime) both generate anti-G protein antibodies very poorly. However, a single immunization with either VLP in RSV-experienced animals resulted in significant titers of anti-G protein antibodies suggesting that RSV infection does induce memory responses to the G protein. In contrast, a second infection with RSV results in barely detectable levels of anti-G protein antibody suggesting that RSV cannot effectively stimulate this anti-G protein memory. One surprising result of this analysis is that the VLP-H/G+Pre-F/F induced significantly higher titers of anti-G protein IgG than the VLP-H/G+Post-F/F in both naïve and RSV-experienced animals. It is important to point out that the two different VLPs, VLP-H/G+Pre-F/Fs and VLP-H/G+Post-F/Fs, contain the same H/G chimera protein and in the same amounts[21]. These results suggest that the conformation of the F protein in VLPs influences induction and stimulation of total anti-G IgG.

In summary, results of assessing levels of anti-F or anti-G protein antibodies in RSV-experienced animals vs naïve animals suggests that RSV infection can induce memory responses but infection is defective in stimulating or activating that memory. Further, these results indicate that the conformation of the F protein in a vaccine candidate has significant impact on the nature of anti-RSV immune responses in mice previously infected with RSV.

EXAMPLE 10

Levels and Durability of Neutralizing Antibody Titers

To address the question of how does prior infection with RSV affect immunization with the invention's VLPs, the protocol of FIG. 11A-B was used to examine neutralizing antibody (NA) levels, as well as the durability of NA titers in sera. The potential influence of the conformation of the RSV F protein on these responses was also examined. Data is shown in FIGS. 16A-B-18 A-C.

As previously demonstrated (FIGS. 1A-B and 12A-B) FIG. 16A-B demonstrates that pre-F/F VLPs stimulate higher titers of neutralizing antibodies and more durable levels of neutralizing antibodies in RSV experienced animals than Post-F/F VLPs. In particular, in RSV primed animals, (1) A single injection of Pre-F/F VLPs resulted in 7 and 3.7 fold higher neutralizing antibody titers than post-F/F VLPs (days 128 vs 220, respectively), (2) Pre-F/F VLPs immunization resulted in 12 and 8 fold higher titers (day 128 vs 220, respectively) than a second RSV Infection and (3) Post-F/F VLPs resulted in 1.8 fold to 2.3 fold higher titers (day 128 vs Day 220) than a second RSV infection. In naïve mice, two injections of Pre-F/F VLPs resulted in titers approximately 50% that of a single immunization in RSV primed animals. Thus, this data shows that immunization of animals previously infected with RSV (to mimic the vast majority of the human population) with Pre-F/F VLPs is far superior to immunization with post-F/F VLPs. The absolute levels of neutralizing antibodies stimulated by Pre-F/F VLPs at day 128 are 7 fold higher than levels stimulated by Post-F/F VLPs.

FIG. 16A-B also shows that neutralizing antibody titers stimulated by Pre-F/F VLPs, post-F/F VLPs, and RSV are similarly durable. Titers after Pre-F/F VLP Immunization dropped 1.8 fold while those after Post-F/F VLP immunization dropped 1.5 fold. Titers after RSV infection dropped 1.2 fold. Because titers after Pre-F/F VLP immunization were 7 fold and 12 fold higher than the titers after Post-F/F VLP or RSV immunization at day 128, the titers after the pre-F/F VLP immunization at day 220 are still much higher than titers after Post-F/F VLP or RSV immunization (3.7 fold and 8 fold). This data shows that immunization of animals previously infected with RSV with Pre-F/F VLPs is far superior to immunization with post-F/F VLPs in terms of absolute Levels of neutralizing antibodies at later times.

FIG. 17A-D shows that total anti-F IgG titers are unaffected by F conformation. In particular, FIG. 17A-D shows that a single immunization of RSV primed animals with VLPs resulted in 10 fold higher IgG titers compared to two immunizations with VLPs in naïve animals. A single immunization of RSV primed animals with VLPs resulted in 10 fold higher IgG titers than RSV infections. Thus, total anti-F IgG levels remained stable with time in all animals. This demonstrates that VLPs stimulate very durable total anti-F IgG antibodies in both RSV primed and naïve animals.

As previously shown in FIG. 14A-B, FIG. 18A-C shows that VLPs stimulate higher anti-G protein titers in RSV experienced animals than in naïve animals, and that the invention's pre-F VLPs stimulate higher anti-G protein titers than post-F VLPs. In particular, FIG. 18A-C shows that, with respect to antibody levels in RSV primed animals: (1) VLPs stimulated 7 fold (pre-F/F VLPs) and 5 fold (post-F/F VLPs) higher anti-G protein titers than in VLPs in naïve animals, (2) VLPs stimulated 65 fold (pre-F VLPs) and 25 fold (post-F/F VLPs) higher anti-G protein antibody titers than two consecutive RSV infections, and (3) Pre-F VLPs stimulated 2.6 fold higher anti-G protein antibody titers than post-F VLPs.

FIG. 18A-C also show that, with respect to antibody levels in naïve animals: (1) Two Pre-F/F VLP immunizations stimulated 10 fold higher anti-G protein antibody titers than two consecutive RSV infections, (2) Two immunizations with post-F/F VLPs stimulated 5 fold higher anti-G protein antibody titers than RSV infection, and (3) Two immunizations with Pre-F/F VLPs consistently stimulated nearly 2 fold higher titers than two immunizations with post-F/F VLPs.

Importantly, the differences in anti-G protein antibody levels shown in FIG. 18A-C were obtained using pre-F/F and Post-F/F VLPs that contained the same G protein in the same amounts. The results suggest that the presence of the F protein, and particularly the pre-F protein in VLPs, has a significant influence on levels of immune responses to the G protein. Since it has been shown by other investigators that G protein has a role in protective responses to RSV, this finding has a significant impact on vaccine formulation.

Regarding the durability of anti-G protein antibodies, FIG. 18A-C shows that, in RSV primed animals, anti-G protein antibodies stimulated by Pre-F/F VLPs were less durable than antibodies stimulated by post-F/F VLPs (decreases with time of 2.6 and 1.25 fold, respectively). FIG. 18A-C also shows that, in naïve animals, titers of anti-G protein antibodies stimulated by pre-F/F VLPs were less durable than titers of anti-G protein antibodies stimulated by Post-F/F VLPs. Pre-F/F VLP titers decreased with time four fold while titers stimulated with Post-F/F VLPs decreased by two fold.

In sum, the data demonstrates that: (1) with respect to the levels of NA, a single injection of VLPs into RSV primed mice stimulates much higher NA titers than in naïve mice, (2) with respect to the durability of NA titers in sera, NA titers are quite stable with time after a single injection of VLPs, particularly the invention's pre-F/F VLPs, (3) F protein conformation influences the levels of NA antibodies since pre-F/F protein in VLPs significantly increased NA titers in mice previously infected with RSV compared to post-F/F VLPs, and (4) F protein conformation influences anti-G protein IgG responses, since pre-F/F protein in VLPs increased anti-G protein IgG responses in RSV experienced animals compared to post-F/F VLPs or RSV infection.

EXAMPLE 11

Anti-Pre-F Protein Antibody Secreting Splenic B Cells

RSV infections, in contrast to the vast majority of virus infections, are defective in memory responses so one can get RSV many times during life. The effect of immunization with VLPs containing pre-F protein or post-F protein on memory B cells secreting antibody to pre-F protein and post-F protein, respectively, was determined. Memory B cells were activated by infecting animals 4 days prior to sacrifice for titration of memory B cells. Data is shown in FIGS. 19A-B and 20A-B.

Figures 19A, 19B:
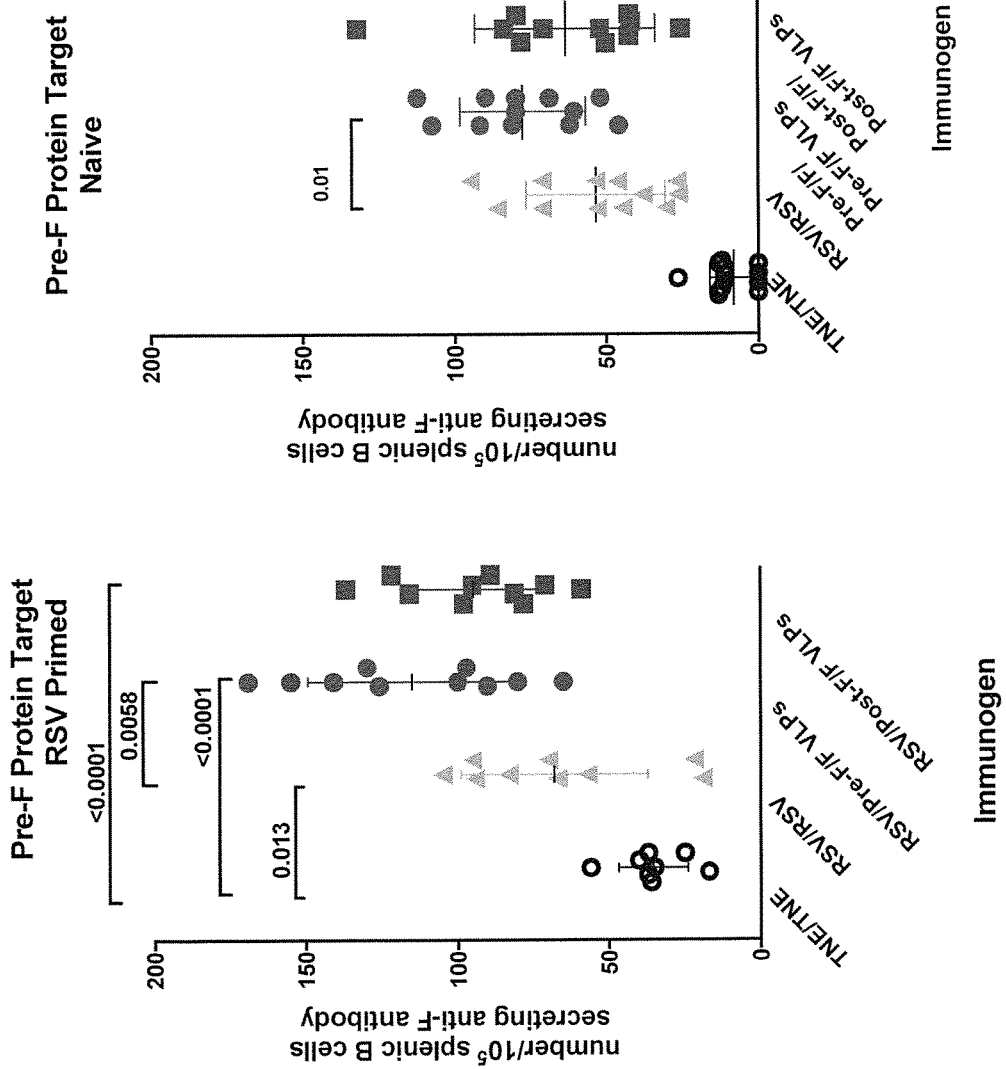
FIG. 19A-B: Anti-pre-F protein antibody secreting splenic B cells in (FIG. 19A) RSV primed animals, and (FIG. 19B) naïve animals. Circles denote RSV/Pre-F/F VLPs (Panel FIG. 19A) or Pre-F/F VLP/Pre-F/F VLPs (Panel FIG. 19B), squares denote RSV/Post-F/F VLPs (panel FIG. 19A) or Post-F/F VLPs/Post-F/F VLPs (panel FIG. 19B), and triangles denote RSV/RSV.

FIG. 19A-B shows that with respect to the pre-F protein target, the titer of memory B cells secreting pre-F antibodies is significantly higher after a single VLP Immunization of RSV primed mice compared to two injections of VLPs in naïve mice. Immunization with Pre-F/F VLPs resulted in higher memory B cell titers compared to post-F/F VLPs.

Figures 20A, 20B:
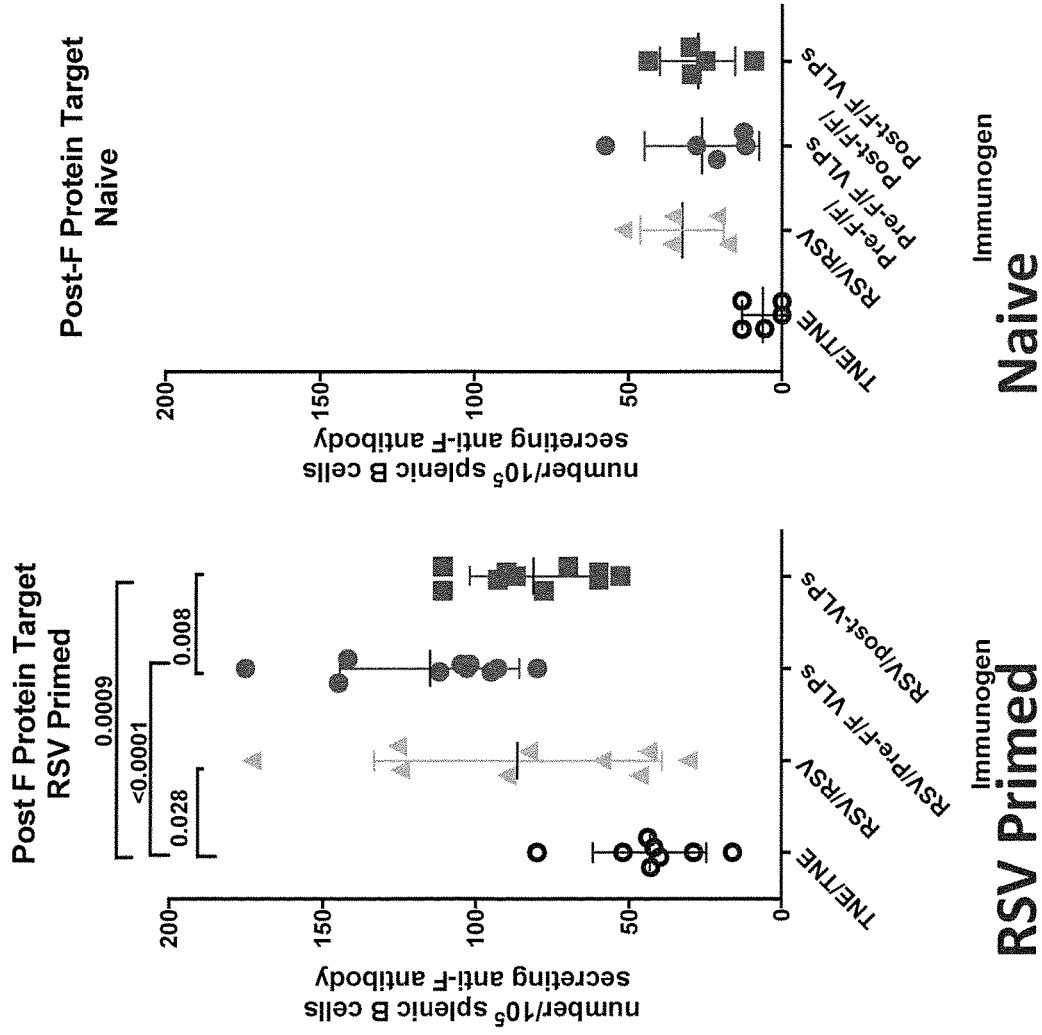
FIG. 20A-B: anti-post-F protein antibody secreting splenic B cells in (FIG. 20A) RSV primed animals, and (FIG. 20B) naïve animals. Circles denote RSV/Pre-F/F VLPs, squares denote RSV/Post-F/F VLPs, and triangles denote RSV/RSV.

FIG. 20A-B shows that similarly to the pre-F protein target, with respect to the post-F protein target, the titer of memory B cells secreting post-F antibodies is significantly higher after a single VLP immunization of RSV primed animals compared to two injections of VLPs in naïve mice. Immunization with Pre-F/F VLPs resulted in higher memory B cell titers compared to post-F/F VLPs in RSV primed animals. FIG. 20A-B also shows that A single injection of VLPs stimulate higher levels of splenic memory B cells in RSV primed mice than two injections in naïve animals, and that VLPs stimulated higher levels of splenic memory B cells than RSV in RSV experienced animals as well as naïve mice.

This data also demonstrates that F protein conformation influences splenic memory B cells, since pre-fusion F/F protein in VLPs stimulated higher levels of splenic memory B cells than post-F/F VLPs in RSV experienced animals.

Thus, the invention's VLPs stimulate memory responses which are superior to those stimulated by RSV infections and are, thus superior in providing long term protection from RSV infection.

EXAMPLE 12

Avidity/Stability of Antigen-Antibody Complexes

We determined the avidity/stability of antigen-antibody complexes in increasing urea for pre-F protein target, post-F protein target, and G protein target. Data is shown in FIG. 21A-C, FIG. 22A-D, and FIG. 23A-B.

Importantly, FIG. 21A-C shows VLPs, particularly pre-F VLPs, stimulated higher avidity anti-F antibodies than RSV infection in RSV primed mice. Indeed, in RSV primed animals, a single dose of VLPs stimulated much higher avidity anti-F antibodies than two consecutive RSV infections.

FIG. 21A-C also shows that the avidity of anti-F specific antibodies stimulated by Pre-F/F VLPs is significantly higher than the avidity of anti-F antibodies stimulated by post-F/F VLPs, and that the avidity of anti-G protein antibodies stimulated by either VLP or RSV infection to soluble G protein is quite weak.

FIGS. 22, A and B, show that in RSV primed animals, Pre-F/F VLPs stimulated higher avidity antibodies than Post-F/F VLPs, i.e., Pre-F/F VLP stimulated antibodies are 1.7 fold more resistant to 7 M urea than Post-F/F VLP stimulated antibodies.

Figure 23A:
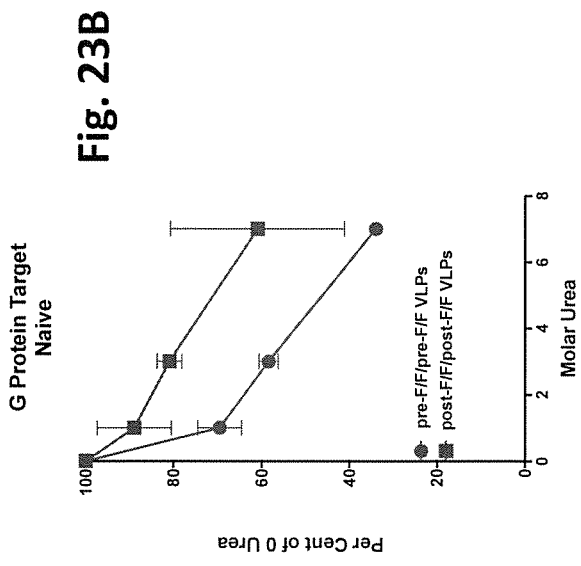
FIG. 23A-B shows avidity of G protein antibodies stimulated in (FIG. 23A) RSV primed animals, and (FIG. 23B) Naïve animals.
Figure 23B:
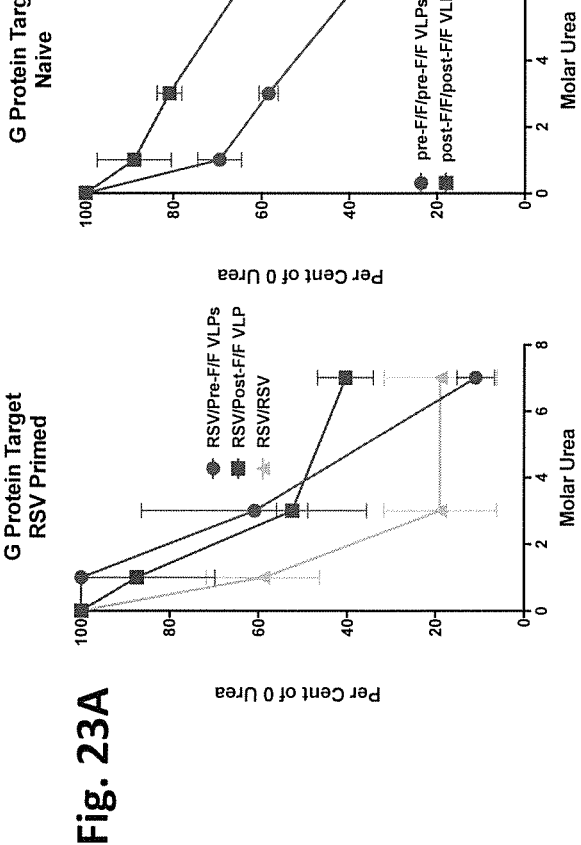

FIG. 23A shows that avidity of anti-G protein antibodies stimulated by VLPs or RSV infection was low, i.e., anti-G protein antibody-G protein complexes are very sensitive to urea.

FIGS. 21A-C-23 A-B also demonstrate that F protein conformation influences the avidity/stability of antigen-antibody complexes, since VLPs, particularly pre-F/F VLPs, stimulate higher avidity anti-F antibodies than RSV infection.

REFERENCES CITED IN "BACKGROUND OF THE INVENTION," "DESCRIPTION OF THE INVENTION," AND "EXAMPLE 2"

1. Karron R A. 2008. Respiratory syncytial virus and parainfluenza virus vaccines. In A PS, A OW, PA O (ed.), Vaccines, 5th ed. Saunders-Elsevier.
2. Falsey A R, Hennessey P A, Formica M A, Cox C Walsh E E. 2005. Respiratory syncytial virus infection in elderly and high-risk adults. N. Engl. J. Med 352:1749-1759.
3. Falsey A R, Walsh E E. 2000. Respiratory syncytial virus infection in adults. Clin Microbiol Rev 13:371-384.
4. Han L L, Alexander J P, Anderson L J. 1999. Respiratory syncytial virus pneumonia among the elderly: an assessment of disease burden. J Infect Dis 179:25-30.
5. Raboni S M, Nogueira M B, Tsuchiya L R, Takahashi G A, Pereira L A, Pasquini R. 2003. Respiratory tract viral infections in bone marrow transplant patients. Transplant. 76:142-146.
6. Hall C B, Long C E, Schnabel K D. 2001. Respiratory syncytial virus infections in previously healthy working adults. Clin Infect Dis 33:792-796.
7. Collins P L, Graham B S. 2007. Viral and host factors in human respiratory syncytial virus pathogenesis. J. Virol. 82:2040-2055.
8. Littel-van den Hurk S D, Mapletoft J W, Arsic N Kovacs-Nolan J. 2007. Immunopathology of RSV infection: prospects for developing vaccines without this complication. Rev Med. Virol. 17:5-34.
9. Openshaw P J, Culley F J, Olszewska W. 2002. Immunopathogenesis of vaccine-enhanced RSV disease. Vaccine. 20:27-31.
10. Openshaw P J, Tregoning J S. 2005. Immune responses and disease enhancement during respiratory syncytial virus infection. Clin Microbiol Rev 18:541-555.
11. Jardetsky T S, Lamb R A. 2004. A class act. Nature. 427.
12. Perrone L A, Ahmad A Veguilla V, Lu X, Smith G, Katz J M, Pushko P, Tumpey T M. 2009. Intranasal Vaccination with 1918 Influenza Virus-Like Particles Protects Mice and Ferrets from Lethal 1918 and H5N1 Influenza Virus Challenge. J. Virol. 83:5726-5734.
13. Lamb R A, Parks G D. 2007. Paramyxoviridae: The Viruses and Their Replication, p. 1450-1496. In Knipe D M, Howley P M, Griffin D E, Lamb R A, Martin M A, Roizman B, Strauss S E (ed.), Fields Virology, Fifth Edition ed, vol. 1. Lippincott Williams &Wilkins, Philadelphia.
14. Arav-Boger R, Willoughby R E, Pass R F, Zong J C, Jang W J, Alcendor D, Hayward G S. 2002. Polymorphisms of the cytomegalovirus (CMV)-encoded tumor necrosis factor-alpha and beta-chemokine receptors in congenital CMV disease. J Infect Dis 186:1057-1064.
15. Blair K S, Smith B W, Mitchell D G, Morton J, Vythilingam M, Pessoa L, Fridberg D, Zametkin A, Sturman D, Nelson E E, Drevets W C, Pine D S, Martin A, Blair R J. 2007. Modulation of emotion by cognition and cognition by emotion. Neuroimage 35:430-440.
16. Swanson K A, Settembre E C, Shaw C A, Dey A K, Rappuoli R, Mandl C W, Dormitzer P R, Carfi A. 2011. Structural basis for immunization with postfusion respiratory syncytial virus fusion F glycoprotein (RSV F) to elicit high neutralizing antibody titers. Proc. Natl. Acad. Sci USA. 108:9619-9624.
17. McLellan J S, Yang Y, Graham B S, Kwong P D. 2011. Structure of Respiratory Syncytial Virus Fusion Glycoprotein in the Postfusion Conformation Reveals Preservation of Neutralizing Epitopes. J. Virol. 85:7788-7796.
18. McLellan J S, Chen M, Leung S, Graepel K W, Du X, Yang Y, Zhou T, Baxa U, Yasuda E, Beaumont T, Kumar A, Modjarrad K, Zheng Z, Zhao M, Xia N, Kwong P D, Graham B S. 2013. Structure of RSV Fusion Glycoprotein Trimer Bound to a Prefusion-Specific Neutralizing Antibody. Science 340:1113-1117.
19. McLellan J S, Chen M, Joyce M G, Sastry M, Stewart-Jones G B E, Yang Y, Zhang B, Chen L, Srivatsan S, Zheng A, Zhou T, Graepel K W, Kumar A, Moin S, Boyington J C, Chuang G-Y, Soto C, Baxa U, Bakker A Q, Spits H, Beaumont T, Zheng Z, Xia N, Ko S-Y, Todd J-P, Rao S, Graham B S, Kwong P D. 2013. Structure-Based Design of a Fusion Glycoprotein Vaccine for Respiratory Syncytial Virus. Science 342:592-598.
20. Smith G, Raghunandan R, Wu Y, Liu Y, Massare M, Nathan M, Zhou B, Lu H, Boddapati S, Li J, Flyer D, Glenn G. 2012. Respiratory Syncytial Virus Fusion Glycoprotein Expressed in Insect Cells Form Protein Nanoparticles That Induce Protective Immunity in Cotton Rats. PLoS ONE 7:e50852.
21. Ngwuta J O, Chen M, Modjarrad K, Joyce M G, Kanekiyo M, Kumar A, Yassine H M, Moin S M, Killikely A M, Chuang G-Y, Druz A, Georgiev I S, Rundlet E J, Sastry M, Stewart-Jones G B E, Yang Y, Zhang B, Nason M C, Capella C, Peeples M E, Ledgerwood J E, McLellan J S, Kwong P D, Graham B S. 2015. Prefusion F—specific antibodies determine the magnitude of RSV neutralizing activity in human sera. Science Transl. Med. 7:309ra162.
22. Magro M, Mas V, Chappell K, Vazquez M, Cano O, Luque D, Terron M C, Melero J A, Palomo C. 2012. Neutralizing antibodies against the preactive form of respiratory syncytial virus fusion protein offer unique possibilities for clinical intervention. Proc. Natl. Acad. Sci. 109:3089-3094.
23. Glezen W, Taber L H, Frank A L, Kasel J A. 1986. Risk of primary infection and reinfection with respiratory syncytial virus. American J. of Dis. of Children 140:543-546.
24. Hall C B. 2001. Respiratory syncytial virus and parainfluenza virus. N Engl J Med 344:1917-1928.
25. Power U F. 2008. Respiratory syncytial virus (RSV) vaccines—Two steps back for one leap forward. J Clin Virol 41:38-44.
26. Pulendran B, Ahmed R. 2011. Immunological mechanisms of vaccination. Nat Immunol 12:509-517.
27. Murawski M R, McGinnes L W, Finberg R W, Kurt-Jones E A, Massare M, Smith G, Heaton P M, Fraire A, Morrison T G. 2010. Newcastle disease virus-like particles containing respiratory syncytial virus G protein induced protection in BALB/c mice with no evidence of immunopathology. J. Virol. 84:1110-1123.
28. McGinnes L W, Gravel K A, Finberg R W, Kurt-Jones E A, Massare M J, Smith G, Schmidt M R, Morrison T G. 2011. Assembly and immunological properties of Newcastle disease virus-like particles containing the respiratory syncytial virus F and G proteins. J. Virol. 85:366-377.
29. Bachmann M F, Jennings G T. 2010. Vaccine delivery: a matter of size, geometry, kinetics and molecular patterns. Nat Rev Immunol 10:787-796.
30. McGinnes Cullen L, Schmidt M R, Kenward S A, Woodland R T, Morrison T G. 2015. Murine Immune Responses to Virus-Like Particle-Associated Pre- and Postfusion Forms of the Respiratory Syncytial Virus F Protein. J. of Virol. 89:6835-6847.
31. Schmidt M R, McGinnes L W, Kenward S A, Willems K N, Woodland R T, Morrison T G. 2012. Long term and memory immune responses in mice against Newcastle disease virus-like particles containing respiratory syncytial virus glycoprotein ectodomains. J. Virol. 86:11654-11662.
32. Morrison T G. 2010. Newcastle disease virus-like particles as a platform for the development of vaccines for human and agricultural pathogens. Future Virol. 5:545-554.
33. Schmidt M R, McGinnes-Cullen L W, Kenward S A, Willems K N, Woodland R T, Morrison T G. 2014. Modification of the respiratory syncytial virus F protein in virus-like particles impacts generation of B cell memory. J Virol 88:10165-10176.
34. McGinnes-Cullen L, Schmidt M R, Kenward S A, Woodland R T, Morrison T G. 2015. Murine Immune Responses to Virus-Like Particle-Associated Pre- and Postfusion Foluis of the Respiratory Syncytial Virus F Protein. J of Virol. 89:6835-6847.
35. McLellan J S, Chen M, Kim A, Yang Y, Graham B S, Kwong P D. 2010. Structural basis of respiratory syncytial virus neutralization by motavizumab. Nat Struct Mol Biol 17.
36. Cullen L M, Blanco J C G, Morrison T G. 2015. Cotton rat immune responses to virus-like particles containing the pre-fusion form of respiratory syncytial virus fusion protein. J. Transl. Med. 13:1-13.
37. Hall C B, Simoes E A F, Anderson L J. 2013. Clinical and Epidemiologic Features of Respiratory Syncytial Virus, p. 39-58. In Anderson L J, Graham B S (ed.), Challenges and Opportunities for Respiratory Syncytial Virus Vaccines, vol. 372. Springer, Heidelberg, N.Y., Dordrecht, Londaon.
38. McLellan J S, Chen M, Kim A, Yang Y, Graham B S, Kwong P D. 2011. Structural basis of respiratory syncytial virus neutralization by motavizumab. Nat Struct Mol Biol 17:248-250.

REFERENCES CITED IN EXAMPLE 1, AND EXAMPLES 3-9

1. Karron R A. Respiratory syncytial virus and parainfluenza virus vaccines. In: Plotkin S A, Orenstein W A, Offit P, eds. Vaccines. 5th ed: Saunders-Elsevier; 2008:1146.
2. Falsey A R, Hennessey P A, Formica M A, Cox C, Walsh E E. Respiratory syncytial virus infection in elderly and high-risk adults. N Engl J Med 2005; 352:1749-59.
3. Falsey A R, Walsh E E. Respiratory syncytial virus infection in adults. Clin Microbiol Rev 2000; 13:371-84.
4. Han L L, Alexander J P, Anderson L J. Respiratory syncytial virus pneumonia among the elderly: an assessment of disease burden. J Infect Dis 1999; 179:25-30.
5. Raboni S M, Nogueira M B, Tsuchiya L R, Takahashi G A, Pereira L A, Pasquini R. Respiratory tract viral infections in bone marrow transplant patients. Transplant 2003; 76:142-6.
6. Hall C B, Long C E, Schnabel K D. Respiratory syncytial virus infections in previously healthy working adults. Clin Infect Dis 2001; 33:792-6.
7. Power U F. Respiratory syncytial virus (RSV) vaccines—Two steps back for one leap forward. J Clin Virol 2008; 41:38-44.
8. Graham B S. Biological challenges and technological opportunities for respiratory syncytial virus vaccine development. Immunol Rev 2012; 239:149-66.
9. Morrison T G, Walsh E E. Subunit and Virus-like Particle Vaccine Approached for Respiratory Syncytial Virus. In: Anderson L J, Graham B S, eds. Challenges and opportunities for respiratory syncytial virus vaccines. Heidelberg, Berlin: Springer; 2013.
10. Jardetsky T S, Lamb R A. A class act. Nature 2004; 427.
11. Lamb R A, Parks G D. Paramyxoviridae: The Viruses and Their Replication. In: Knipe D M, Howley P M, Griffin D E, et al., eds. Fields Virology. Fifth Edition ed. Philadelphia: Lippincott Williams & Wilkins; 2007:1450-96.
12. Swanson K A, Settembre E C, Shaw C A, et al. Structural basis for immunization with postfusion respiratory syncytial virus fusion F glycoprotein (RSV F) to elicit high neutralizing antibody titers. Proc Natl Acad Sci USA 2011; 108:9619-24.
13. McLellan J S, Yang Y, Graham B S, Kwong P D. Structure of Respiratory Syncytial Virus Fusion Glycoprotein in the Postfusion Conformation Reveals Preservation of Neutralizing Epitopes. J Virol 2011; 85:7788-96.
14. McLellan J S, Chen M, Leung S, et al. Structure of RSV Fusion Glycoprotein Trimer Bound to a Prefusion-Specific Neutralizing Antibody. Science 2013; 340:1113-7.
15. McLellan J S, Chen M, Joyce M G, Sastry M, Stewart-Jones G B E, Yang Y. Structure-based design of a fusion glycoprotein vaccine for respiratory syncytial virus. Science 2013; 342:592-8.
16. Hall C B, Simoes E A F, Anderson L J. Clinical and Epidemiologic Features of Respiratory Syncytial Virus. In: Anderson L J, Graham B S, eds. Challenges and Opportunities for Respiratory Syncytial Virus Vaccines. Heidelberg, N.Y., Dordrecht, Londaon: Springer; 2013: 39-58.
17. Glezen W, Taber L H, Frank A L, Kasel J A. RIsk of primary infection and reinfection with respiratory syncytial virus. American J of Dis of Children 1986; 140:543-6.
18. McGinnes L W, Gravel K A, Finberg R W, Kurt-Jones E A, Massare M J, Smith G. Assembly and immunological properties of Newcastle disease virus-like particles containing the respiratory syncytial virus F and G proteins. J Virol 2011; 85:366-77.
19. Murawski M R, McGinnes L W, Finberg R W, Kurt-Jones E A, Massare M, Smith G. Newcastle disease virus-like particles containing respiratory syncytial virus G protein induced protection in BALB/c mice with no evidence of immunopathology. J Virol 2010; 84:1110-23.
20. Bachmann M F, Jennings G T. Vaccine delivery: a matter of size, geometry, kinetics and molecular patterns. Nat Rev Immunol 2010; 10:787-96.
21. McGinnes-Cullen L, Schmidt M R, Kenward S A, Woodland R T, Morrison T G. Murine Immune Responses to Virus-Like Particle-Associated Pre- and Postfusion Forms of the Respiratory Syncytial Virus F Protein. J of Virol 2015; 89:6835-47.
22. Cullen L M, Blanco J C G, Morrison T G. Cotton rat immune responses to virus-like particles containing the pre-fusion form of respiratory syncytial virus fusion protein. J Transl Med 2015; 13:1-13.

23. McLellan J S, Chen M, Kim A, Yang Y, Graham B S, Kwong P D. Structural basis of respiratory syncytial virus neutralization by motavizumab. Nat Struct Mol Biol 2011; 17:248-50.
24. Boyoglu-Barnum S, Todd S O, Chirkova T, Barnum T R, Gaston K A, Haynes L M. An anti-G protein monoclonal antibody treats RSV disease more effectively than an anti-F monoclonal antibody in BALB/c mice. Virology 2015; 483.
25. Boyoglu-Barnum S, Todd S O, Chirkova T, et al. An anti-G protein monoclonal antibody treats RSV disease more effectively than an anti-F monoclonal antibody in BALB/c mice. Virology 2015; 483:117-25.
26. Tripp R A. Pathogenesis of respiratory syncytial virus infection. Viral Immunol 2004; 17:165-81.
27. Tripp R A, Jones L P, Haynes L M, Zheng H, Murphy P M, Anderson L J. CX3C chemokine mimicry by respiratory syncytial virus G glycoprotein. Nat Immunol 2001; 2:732-8.
28. Hall C B. Respiratory syncytial virus and parainfluenza virus. N Engl J Med 2001; 344:1917-28.
29. Gilman M S A, Castellanos C A, Chen M, et al. Rapid profiling of RSV antibody repertoires from the memory B cells of naturally infected adult donors. Sci Immunol 2016; 1:1879.
30. Collins P L, Crowe J E. Respiratory syncytial virus and metapneumovirus. 5 ed. Philadelphia: LippincottWilliams and Wilkins; 2007.
31. Chirkova T, Boyoglu-Barnum S, Gaston K A, et al. Respiratory Syncytial Virus G Protein CX3C Motif Impairs Human Airway Epithelial and Immune Cell Responses. J of Virol 2013; 87:13466-79.
32. Rey G U, Miao C, Caidi H, et al. Decrease in Formalin-Inactivated Respiratory Syncytial Virus (FI-RSV) Enhanced Disease with RSV G Glycoprotein Peptide Immunization in BALB/c Mice. PLoS ONE 2013; 8:e83075.
33. McGinnes L W, Pantua H, Laliberte J P, Gravel K A, Jain S, Morrison T G. Assembly and biological and immunological properties of Newcastle disease virus-like particles. J Virol 2010; 84:4513-23.
34. McGinnes L W, Reitter J, Pantua H D, Morrison T G. Newcastle disease virus: propagation, quantification, and storage: John Wiley and sons, Inc; 2006.
35. McGinnes L W, Morrison T G. Newcastle Disease Virus-Like Particles: Preparation, Purification, Quantification, and Incorporation of Foreign Glycoproteins. Current Protocols in Microbiology: John Wiley & Sons, Inc.; 2013.
36. Gravel K A, McGinnes L W, Reitter J, Morrison T G. The transmembrane domain sequence affects the structure and function of the Newcastle disease virus fusion protein. J Virol 2011; 85:3486-97.
37. Beeler J A, van Wyke Coelingh K. Neutralization epitopes of the F glycoprotein of respiratory syncytial virus: effect of mutation upon fusion function. J Virol 1989; 63:2941-50.
38. McGinnes L W, Morrison T G. Current Protocols in Microbiology. USA: Wiley; 2013.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

I claim:

1. A method for immunizing a mammalian subject, comprising,
    a) providing
        i) a first RSV experienced mammalian subject containing Respiratory Syncytial Virus (RSV) neutralizing antibodies, and
        ii) a first composition comprising recombinant chimeric Newcastle Disease virus-like particles (ND VLPs) that contain,
        in operable combination, CT domain of NDV HN protein, TM domain of NDV HN protein, and RSV G ectodomain protein, and
        a chimeric protein comprising, in operable combination,
            1) stabilized pre-fusion RSV F protein ectodomain comprising SEQ ID NO: 06,
            2) transmembrane (TM) domain of NDV F protein, and
            3) cytoplasmic (CT) domain of NDV F protein, and
    b) administering an immunologically effective amount of the first composition to the first RSV experienced mammalian subject to produce a first immunized mammalian subject, wherein said administering is under conditions that increase the level of the RSV neutralizing antibodies in said first immunized mammalian subject.

2. The method of claim 1, wherein the level of the rsv neutralizing antibodies in the first rsv experienced subject does not prevent rsv infection of the first rsv experienced subject.

3. The method claim 2, wherein the level of the RSV neutralizing antibodies in the first immunized subject reduces RSV infection of the first immunized subject compared to the first RSV experienced subject.

4. The method of claim 2, wherein the level of the RSV neutralizing antibodies in the first immunized subject reduces one or more symptoms of RSV infection.

5. The method of claim 2, wherein the level of the RSV neutralizing antibodies in the first immunized subject reduces susceptibility of the first immunized subject to RSV infection compared to the first RSV experienced subject.

6. The method of claim 2, wherein the level of the RSV neutralizing antibodies in the first immunized subject reduces transmission of RSV infection from the first immunized subject.

7. The method of claim 2, wherein the increase in the level of the RSV neutralizing antibodies in the first immunized subject is at least 100% compared to the level of RSV neutralizing antibodies in the first RSV experienced subject.

8. The method of claim 1, wherein the first immunized subject comprises an increase in the level of the RSV neutralizing antibodies compared to the level of RSV neutralizing antibodies in a second RSV experienced subject that is infected with RSV.

9. The method of claim 8, wherein the increase in the level of the RSV neutralizing antibodies in the first immunized subject is at least 100% compared to the level of RSV neutralizing antibodies in the second RSV experienced subject that is infected with RSV.

10. The method of claim 1, wherein the first immunized subject comprises an increase in the level of the RSV neutralizing antibodies compared to the level of RSV neutralizing antibodies in a second immunized subject, wherein said second immunized subject is a second RSV experienced subject that is immunized with a second composition comprising chimeric ND VLPs that contain, in operable combination
 1) stabilized post-fusion RSV F protein ectodomain comprising SEQ ID NO:08,
 2) TM domain of NDV F protein, and
 3) CT domain of NDV F protein.

11. The method of claim 1, wherein the chimeric ND VLPs further comprise, in operable combination, foldon sequence listed as SEQ ID NO:14.

12. The method of claim 1, wherein the level of the RSV neutralizing antibodies after a single administration of a dose of the first composition to the first RSV experienced subject is substantially the same as the level of RSV neutralizing antibodies after twice administering the dose of the first composition to a naive subject.

13. The method of claim 1, further comprising comparing the level of the RSV neutralizing antibodies in the first immunized subject to the level of the RSV neutralizing antibodies in one or more test subjects selected from the group consisting of
 a) the first RSV experienced subject,
 b) a second RSV experienced subject that is infected with RSV,
 c) a second RSV experienced subject that is treated with a second composition comprising chimeric ND VLPs that contain, in operable combination
  1) stabilized post-fusion RSV F protein ectodomain comprising SEQ ID NO:08,
  2) TM domain of NDV F protein, and
  3) CT domain of NDV F protein,
 wherein detecting an increase in the level of the RSV neutralizing antibodies in the first immunized subject compared to the level of the RSV neutralizing antibodies in the one or more test subjects indicates that the first immunized subject is immunized against the RSV infection.

14. The method of claim 1, further comprising detecting in the first immunized subject a reduction in one or more of (a) level of RSV infection, (b) one or more symptoms of RSV infection, (c) susceptibility to RSV infection, and (d) transmission of RSV infection, compared to the first RSV experienced subject.

15. The method of claim 1, wherein lung tissue of the first immunized subject contains a lower RSV titer than lung tissue of a naive subject to which the first composition has not been administered.

16. The method of claim 1, wherein the level of the RSV neutralizing antibodies after a single administration of the first composition to the first RSV experienced subject is higher than the level of RSV neutralizing antibodies after a single administration of the first composition to a naive subject.

17. A vaccine comprising recombinant chimeric Newcastle Disease virus-like particles (ND VLPs) that contain a chimeric protein comprising, in operable combination,
 1) stabilized pre-fusion RSV F protein ectodomain comprising SEQ ID NO:06,
 2) transmembrane (TM) domain of NDV F protein,
 3) cytoplasmic (CT) domain of NDV F protein, and
 4) RSV G ectodomain protein.

18. The vaccine of claim 17, further comprising, in operable combination, foldon sequence listed as SEQ ID NO:14.

19. The vaccine of claim 17, wherein the RSV G ectodomain protein sequence is operably linked to NDV HN TM domain and to NDV HN CT domain.

20. The method of claim 1, wherein the level of said RSV neutralizing antibodies does not reduce RSV infection.

21. The method of claim 1, wherein the level of said RSV neutralizing antibodies does not reduce symptoms of RSV infection.

22. The method of claim 1, wherein the level of said RSV neutralizing antibodies does not reduce susceptibility to RSV infection.

23. The method of claim 1, wherein the level of said RSV neutralizing antibodies does not reduce transmission of RSV infection from the first RSV experienced mammalian subject.

24. The method of claim 1, wherein said administering comprises a single administration of said immunologically effective amount of said first composition.

25. A vaccine comprising,
 1) stabilized pre-fusion RSV F protein ectodomain comprising SEQ ID NO:06, and
 2) RSV G ectodomain protein.

26. A method for immunizing a mammalian subject, comprising,
 a) providing
  i) a first RSV experienced mammalian subject containing Respiratory Syncytial Virus (RSV) neutralizing antibodies, and
  ii) a first composition comprising the vaccine of claim 25, and
 b) administering an immunologically effective amount of the first composition to the first RSV experienced mammalian subject to produce a first immunized mammalian subject, wherein said administering is under conditions that increase the level of the RSV neutralizing antibodies in said first immunized mammalian subject.

27. The method of claim 26, wherein the level of the RSV neutralizing antibodies in the first RSV experienced subject does not prevent RSV infection of the first RSV experienced subject.

28. The method of claim 26, wherein the increase in the level of the RSV neutralizing antibodies in the first immunized subject is at least 100% compared to the level of RSV neutralizing antibodies in the first RSV experienced subject.

* * * * *

SEQUENCE LISTING

```
<160> NUMBER OF SEQ ID NOS: 18

<210> SEQ ID NO 1
<211> LENGTH: 1815
<212> TYPE: DNA
<213> ORGANISM: Artificial Sequence
<220> FEATURE:
<223> OTHER INFORMATION: Synthetic

<400> SEQUENCE: 1
atggagctgc tgatcctgaa ggccaacgcc attaccacca ttctgacagc cgtgacattc      60
tgcttcgcct ccggacagaa catcacagag gagttctatc agagcacctg ttccgccgtc     120
tccaaaggat atctgagcgc cctgaggacc ggctggtata cctccgtgat caccatcgag     180
cttagcaaca tcaaggagaa caagtgcaat ggcaccgacg ccaaggtcaa gctcatcaag     240
caagagcttg acaagtacaa aaacgccgtc accgagcttc agctgctgat gcagtccaca     300
ccagctacca acaacagagc caggagagag cttcccagat tcatgaacta caccctgaac     360
aacgccaaga agaccaacgt gacccctgtcc aagaaaagga aaggaggtt cctgggcttc     420 ctcctgggag tgggatccgc catcgctagc ggcgtggccg tctgtaaagt cctccatctg     480
gaaggcgagg tcaacaagat caaaagcgcc ctgctgtcca caaacaaagc tgtggtctcc     540
ctgagcaacg gcgtcagcgt cctgaccttc aaggtgctcg acctcaagaa ctacatcgac     600
aagcaactgc tccccatcct caacaagcag agctgcagga tcagcaacat tgaaaccgtg     660
```

```
atcgagttcc agcagaagaa taacaggctc ctggagatca ccagggagtt cagcgtgaat    720
gctggcgtga caaccccgt ctccacctac atgctgacca acagcgaact cctgagcctg    780
atcaacgata tgcccatcac caacgaccag aagaagctca tgagcaacaa cgtccagatc    840
gtgaggcagc agagctacag catcatgtgc attatcaaag aggaggtcct ggcttacgtg    900
gtccagctgc ccctgtatgg agtcattgac accccctgct ggaaactcca taccagccca    960
ctgtgtacaa ccaacaccaa ggagggcagc aacatctgcc tcaccagaac cgataggggc   1020
tggtactgcg acaacgccgg atccgtgagc ttcttccccc aggccgagac ctgcaaggtc   1080
cagagcaaca gggtcttctg cgataccatg aacagcctca ccctgccctc cgaggtgaat   1140
ctctgtaatg tcgacatctt caatccaaag tacgactgta agatcatgac cagcaagacc   1200
gacgtcagca gcagcgtgat taccagcctc ggagccatcg tgagctgtta cggcaagacc   1260
aagtgcaccg ccagcaacaa gaacagagga attatcaaga ccttcagcaa cggatgcgac   1320
tacgtctcca acaaggcgt ggataccgtc tccgtgggca cacccctgta ctacgtcaac   1380
aagcaggaag gcaaaagcct gtacgtcaag ggcgagccaa tcatcaactt ttacgatccc   1440
ctcgtcttcc catccgatga gttcgacgcc agcatctccc aagtcaacga gaagatcaac   1500
cagtccctgg ccttcatcag aaagtccgac gagctcctcc ataacgtcaa cgccgggaaa   1560
ggatatatcc ccgaagctcc tcgggatggt caggcctacg ttcgcaagga tggagagtgg   1620
gtactgctgt ctactttcct gagtactact aatctcatta cctatatcgc tttaactgcc   1680
atatctcttg tttgcggtat acttagtctg gttctagcat gctacctaat gtacaagcaa   1740
aaggcgcaac aaaagacctt gttatggctt gggaataata ccctgggtca gatgagagcc   1800
actacaaaaa tgtga                                                    1815
```

<210> SEQ ID NO 2
<211> LENGTH: 604
<212> TYPE: PRT
<213> ORGANISM: Artificial Sequence
<220> FEATURE:
<223> OTHER INFORMATION: Synthetic

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160
```

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Gly Tyr Ile Pro Glu Ala Pro Arg
        515                 520                 525

Asp Gly Gln Ala Tyr Val Arg Lys Asp Gly Glu Trp Val Leu Leu Ser
    530                 535                 540

Thr Phe Leu Ser Thr Thr Asn Leu Ile Thr Tyr Ile Ala Leu Thr Ala
545                 550                 555                 560

Ile Ser Leu Val Cys Gly Ile Leu Ser Leu Val Leu Ala Cys Tyr Leu
                565                 570                 575
```

Met Tyr Lys Gln Lys Ala Gln Gln Lys Thr Leu Leu Trp Leu Gly Asn
            580                 585                 590

Asn Thr Leu Gly Gln Met Arg Ala Thr Thr Lys Met
            595                 600

<210> SEQ ID NO 3
<211> LENGTH: 1704
<212> TYPE: DNA
<213> ORGANISM: Artificial Sequence
<220> FEATURE:
<223> OTHER INFORMATION: Synthetic

<400> SEQUENCE: 3

```
atggagcttc ttattctcaa agccaatgct attactacca tcctgacagc cgtgacattt      60
tgcttcgcca gtggacagaa tatcactgag gaattctatc agagcaccty ttccgctgta     120
tcaaagggt atctctccgc attacgaacc ggatggtaca cttcagtcat cacaattgaa     180
ctttctaaca ttaaagagaa taagtgtaac gggactgacg ctaaagtgaa gttgataaag     240
caggagctag acaaatataa gaatgcagta actgaacttc agttgcttat gcagtccaca     300
cctgctacta acaatagagc acgccgtgaa ctgcctagat tcatgaacta tactcttaat     360
aacgcaaaaa agactaatgt taccctttcc aagaaacaga aacagcaagc tattgcttca     420
ggagtagcag taagtaaggt attacatttg gaaggcgaag tgaacaaaat taaatcagca     480
ctgctttcca ctaacaaggc agtagtgagt ctgtctaatg tgttagcgt tttaacttct     540
aaagtgctgg atttaaagaa ctacatcgat aaacagctgc tccccatcgt aaacaagcag     600
agttgccgta tcagcaacat agagacagtg atagagtttc agcagaagaa caataggctg     660
cttgaaataa ctcgcgaatt tagcgttaac gcaggcgtga ctaccccagt gtccacttat     720
atgctgacaa actcagagtt actttctctg atcaacgaca tgccaataac taatgatcag     780
aagaaattaa tgtctaataa cgtgcagata gttcggcagc agtcctacag tatcatgagc     840
attatcaagg aagaggtatt ggcctatgtc gttcagttac ctttatacgg tgttatcgat     900
accccatgtt ggaagctcca taccagcccc ttgtgtacta ccaatactaa agaggggagc     960
aatatttgtc taactaggac cgatagggc tggtactgcg acaacgcagg gagtgttct    1020
ttctttcctc aggcagaaac atgcaaggtg cagagcaaca gagtgttttg cgatactatg    1080
aatagcctga ctctgccatc cgaagttaat ctgtgtaacg tcgatatatt taatccaaaa    1140
tacgattgca aaatcatgac ttcaaaaaca gacgtgagca gttcagtcat aacttctcta    1200
ggtgccattg tttcatgcta cggaaaaact aagtgtaccg ctagcaacaa aaacagaggt    1260
attatcaaga ctttctccaa tggctgcgat tacgtttcca acaagggtgt cgatacagtc    1320
tcagtcggga taccttata ttacgttaat aaacaggagg ggaagtctct gtatgtgaaa    1380
ggtgagccaa taattaattt ttatgatcct ttagtatttc catctgacga gtttgacgca    1440
tccatttctc aggttaacga aaagatcaac cagagcttgg cttttataag gaagagtgac    1500
gagctcctcc ataacgtcaa cgccgggaaa agtactacta atctcattac ctatatcgct    1560
ttaactgcca tatctcttgt ttgcggtata cttagtctgg ttctagcatg ctacctaatg    1620
tacaagcaaa aggcgcaaca aaagaccttg ttatggcttg ggaataatac cctgggtcag    1680
atgagagcca ctacaaaaat gtga                                           1704
```

<210> SEQ ID NO 4
<211> LENGTH: 567
<212> TYPE: PRT
<213> ORGANISM: Artificial Sequence
<220> FEATURE:
<223> OTHER INFORMATION: Synthetic

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ala Ile Ala Ser Gly Val Ala Val
    130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Arg Ile Ser Asn Ile Glu
        195                 200                 205

Thr Val Ile Glu Phe Gln Gln Lys Asn Asn Arg Leu Leu Glu Ile Thr
    210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270

Gln Gln Ser Tyr Ser Ile Met Ser Ile Ile Lys Glu Glu Val Leu Ala
        275                 280                 285

Tyr Val Val Gln Leu Pro Leu Tyr Gly Val Ile Asp Thr Pro Cys Trp
    290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
        355                 360                 365

Val Asn Leu Cys Asn Val Asp Ile Phe Asn Pro Lys Tyr Asp Cys Lys
    370                 375                 380

Ile Met Thr Ser Lys Thr Asp Val Ser Ser Ser Val Ile Thr Ser Leu
385                 390                 395                 400

```
Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
        435                 440                 445

Val Asn Lys Gln Glu Gly Lys Ser Leu Tyr Val Lys Gly Glu Pro Ile
    450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn Leu Ile Thr Tyr Ile Ala Leu Thr Ala Ile Ser Leu Val Cys
        515                 520                 525

Gly Ile Leu Ser Leu Val Leu Ala Cys Tyr Leu Met Tyr Lys Gln Lys
    530                 535                 540

Ala Gln Gln Lys Thr Leu Leu Trp Leu Gly Asn Asn Thr Leu Gly Gln
545                 550                 555                 560

Met Arg Ala Thr Thr Lys Met
                565

<210> SEQ ID NO 5
<211> LENGTH: 1560
<212> TYPE: DNA
<213> ORGANISM: Artificial Sequence
<220> FEATURE:
<223> OTHER INFORMATION: Synthetic

<400> SEQUENCE: 5
atggagctgc tgatcctgaa ggccaacgcc attaccacca ttctgacagc cgtgacattc      60
tgcttcgcct ccggacagaa catcacagag gagttctatc agagcacctg ttccgccgtc     120
tccaaaggat atctgagcgc cctgaggacc ggctggtata cctccgtgat caccatcgag     180
cttagcaaca tcaaggagaa caagtgcaat ggcaccgacg ccaaggtcaa gctcatcaag     240
caagagcttg acaagtacaa aaacgccgtc accgagcttc agctgctgat gcagtccaca     300
ccagctacca caacagagc caggagagag cttcccagat tcatgaacta cacccctgaac    360 aacgccaaga gaccaacgt gaccctgtcc aagaaaagga aaggaggtt cctgggcttc      420 ctcctgggag tgggatccgc catcgctagc ggcgtggccg tctgtaaagt cctccatctg     480
gaaggcgagt caacaagat caaaagcgcc ctgctgtcca aaacaaagc tgtggtctcc      540 ctgagcaacg gcgtcagcgt cctgaccttc aaggtgctcg acctcaagaa ctacatcgac     600
aagcaactgc tccccatcct caacaagcag agctgcagga tcagcaacat gaaaccgtg     660 atcgagttcc agcagaagaa taacaggctc ctggagatca ccagggagtt cagcgtgaat    720
gctggcgtga caccccccgt ctccacctac atgctgacca cagcgaact cctgagcctg     780 atcaacgata tgcccatcac caacgaccag aagaagctca tgagcaacaa cgtccagatc     840
gtgaggcagc agagctacag catcatgtgc attatcaaag aggaggtcct ggcttacgtg     900
gtccagctgc ccctgtatgg agtcattgac accccctgct ggaaactcca taccagccca     960
ctgtgtacaa ccaacaccaa ggagggcagc aacatctgcc tcaccagaac cgatagggc    1020 tggtactgcg acaacgccgg atccgtgagc ttcttccccc aggccgagac ctgcaaggtc    1080
```

```
cagagcaaca gggtcttctg cgataccatg aacagcctca ccctgccctc cgaggtgaat    1140
ctctgtaatg tcgacatctt caatccaaag tacgactgta agatcatgac agcaagacc    1200 gacgtcagca gcagcgtgat taccagcctc ggagccatcg tgagctgtta cggcaagacc    1260
aagtgcaccg ccagcaacaa gaacagagga attatcaaga ccttcagcaa cggatgcgac    1320
tacgtctcca caaaggcgt ggataccgtc tccgtgggca caccctgta ctacgtcaac    1380 aagcaggaag gcaaaagcct gtacgtcaag ggcgagccaa tcatcaactt ttacgatccc    1440
ctcgtcttcc catccgatga gttcgacgcc agcatctccc aagtcaacga gaagatcaac    1500
cagtccctgg ccttcatcag aaagtccgac gagctcctcc ataacgtcaa cgccgggaaa    1560
```

<210> SEQ ID NO 6
<211> LENGTH: 524
<212> TYPE: PRT
<213> ORGANISM: Artificial Sequence
<220> FEATURE:
<223> OTHER INFORMATION: Synthetic

<400> SEQUENCE: 6

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

Met Cys Ile Ile Lys Glu Glu Val Leu Ala Tyr Val Val Gln Leu Pro
    290             295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn
        515                 520

<210> SEQ ID NO 7
<211> LENGTH: 1542
<212> TYPE: DNA
<213> ORGANISM: Artificial Sequence
<220> FEATURE:
<223> OTHER INFORMATION: Synthetic

<400> SEQUENCE: 7
atggagcttc ttattctcaa agccaatgct attactacca tcctgacagc cgtgacattt      60
tgcttcgcca gtggacagaa tatcactgag gaattctatc agagcacctg ttccgctgta     120 tcaaagggt atctctccgc attacgaacc ggatggtaca cttcagtcat acaattgaa       180 ctttctaaca ttaaagagaa taagtgtaac gggactgacg ctaaagtgaa gttgataaag     240
caggagctag acaaatataa gaatgcagta actgaacttc agttgcttat gcagtccaca     300
cctgctacta caatagagc acgccgtgaa ctgcctagat tcatgaacta tactcttaat     360
aacgcaaaaa agactaatgt tacccttttcc aagaaacaga acagcaagc tattgcttca    420 ggagtagcag taagtaaggt attacatttg gaaggcgaag tgaacaaaat taaatcagca    480
ctgctttcca ctaacaaggc agtagtgagt ctgtctaatg gtgttagcgt tttaacttct    540
aaagtgctgg atttaaagaa ctacatcgat aaacagctgc tccccatcgt aaacaagcag   600
agttgccgta tcagcaacat agagacagtg atagagtttc agcagaagaa caataggctg   660
cttgaaataa ctcgcgaatt tagcgttaac gcaggcgtga ctaccccagt gtccacttat   720

```
atgctgacaa actcagagtt actttctctg atcaacgaca tgccaataac taatgatcag    780
aagaaattaa tgtctaataa cgtgcagata gttcggcagc agtcctacag tatcatgagc    840
attatcaagg aagaggtatt ggcctatgtc gttcagttac ctttatacgg tgttatcgat    900
acccatgtt ggaagctcca taccagcccc ttgtgtacta ccaatactaa agaggggagc     960
aatatttgtc taactaggac cgatagggc tggtactgcg acaacgcagg gagtgtttct    1020
ttctttcctc aggcagaaac atgcaaggtc cagagcaaca gagtgttttg cgatactatg   1080
aatagcctga ctctgccatc cgaagttaat ctgtgtaacg tcgatatatt taatccaaaa   1140
tacgattgca aaatcatgac ttcaaaaaca gacgtgagca gttcagtcat aacttctcta   1200
ggtgccattg tttcatgcta cggaaaaact aagtgtaccg ctagcaacaa aaacagaggt   1260
attatcaaga ctttctccaa tggctgcgat tacgtttcca acaagggtgt cgatacagtc   1320
tcagtcggga ataccttata ttacgttaat aaacaggagg ggaagtctct gtatgtgaaa   1380
ggtgagccaa taattaattt ttatgatcct ttagtatttc catctgacga gtttgacgca   1440
tccatttctc aggttaacga aaagatcaac cagagcttgg cttttataag gaagagtgac   1500
gagctcctcc ataacgtcaa cgccgggaaa agtactacta at                     1542
```

<210> SEQ ID NO 8
<211> LENGTH: 514
<212> TYPE: PRT
<213> ORGANISM: Artificial Sequence
<220> FEATURE:
<223> OTHER INFORMATION: Synthetic

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ala Ile Ala Ser Gly Val Ala Val
    130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Arg Ile Ser Asn Ile Glu
        195                 200                 205

Thr Val Ile Glu Phe Gln Gln Lys Asn Asn Arg Leu Leu Glu Ile Thr
    210                 215                 220
```

-continued

```
Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
            245                 250                 255

Thr Asn Asp Gln Lys Lys Leu Met Ser Asn Asn Val Gln Ile Val Arg
        260                 265                 270

Gln Gln Ser Tyr Ser Ile Met Ser Ile Ile Lys Glu Glu Val Leu Ala
    275                 280                 285

Tyr Val Val Gln Leu Pro Leu Tyr Gly Val Ile Asp Thr Pro Cys Trp
290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
        355                 360                 365

Val Asn Leu Cys Asn Val Asp Ile Phe Asn Pro Lys Tyr Asp Cys Lys
370                 375                 380

Ile Met Thr Ser Lys Thr Asp Val Ser Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
        435                 440                 445

Val Asn Lys Gln Glu Gly Lys Ser Leu Tyr Val Lys Gly Glu Pro Ile
    450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn
```

```
<210> SEQ ID NO 9
<211> LENGTH: 95
<212> TYPE: DNA
<213> ORGANISM: Artificial Sequence
<220> FEATURE:
<223> OTHER INFORMATION: Synthetic

<400> SEQUENCE: 9
ctcattacct atatcgcttt aactgccata tctcttgttt gcggtatact tagtctggtt    60
ctagcatgct acctaatgta caagcaaaag gcgca                              95

<210> SEQ ID NO 10
<211> LENGTH: 27
<212> TYPE: PRT
<213> ORGANISM: Artificial Sequence
<220> FEATURE:
<223> OTHER INFORMATION: Synthetic
```

<400> SEQUENCE: 10

Leu Ile Thr Tyr Ile Ala Leu Thr Ala Ile Ser Leu Val Cys Gly Ile
1               5                   10                  15

Leu Ser Leu Val Leu Ala Cys Tyr Leu Met Tyr
            20                  25

<210> SEQ ID NO 11
<211> LENGTH: 67
<212> TYPE: DNA
<213> ORGANISM: Artificial Sequence
<220> FEATURE:
<223> OTHER INFORMATION: Synthetic

<400> SEQUENCE: 11
acaaaagacc ttgttatggc ttgggaataa taccctgggt cagatgagag ccactacaaa    60
aatgtga                                                             67

<210> SEQ ID NO 12
<211> LENGTH: 26
<212> TYPE: PRT
<213> ORGANISM: Artificial Sequence
<220> FEATURE:
<223> OTHER INFORMATION: Synthetic

<400> SEQUENCE: 12

Lys Gln Lys Ala Gln Gln Lys Thr Leu Leu Trp Leu Gly Asn Asn Thr
1               5                   10                  15

Leu Gly Gln Met Arg Ala Thr Thr Lys Met
            20                  25

<210> SEQ ID NO 13
<211> LENGTH: 92
<212> TYPE: DNA
<213> ORGANISM: Artificial Sequence
<220> FEATURE:
<223> OTHER INFORMATION: Synthetic

<400> SEQUENCE: 13
ggatatatcc ccgaagctcc tcgggatggt caggcctacg ttcgcaagga tggagagtgg    60
gtactgctgt ctactttcct gagtactact aa                                 92

<210> SEQ ID NO 14
<211> LENGTH: 27
<212> TYPE: PRT
<213> ORGANISM: Artificial Sequence
<220> FEATURE:
<223> OTHER INFORMATION: Synthetic

<400> SEQUENCE: 14

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 15
<211> LENGTH: 843
<212> TYPE: DNA
<213> ORGANISM: Artificial Sequence
<220> FEATURE:
<223> OTHER INFORMATION: Synthetic

<400> SEQUENCE: 15

```
atgaaccgcg cagtttgcca gttgcgcta gagaatgatg aaagggaagc gaagaataca     60
tggcgcttgg tattccggat cgcaatctta cttttaacag taatgacctt agccatctct    120
gcggccgccc tggcatatag tgcgaatcat aaggtcacac ccacgaccgc aatcattcag    180
gacgctacta gccaaatcaa aaacacaacc cctacgtatt tgactcagaa cccacaactg    240
ggtatttcac cgtcgaatcc cagtgaaatc acctcccaga tcacaactat tcttgcctct    300
accacgcctg gcgttaagag cacactccaa tcaactaccg taaagacgaa aaacacaact    360
accacccaga cgcagccatc caagccgaca actaaacaaa ggcagaacaa gccccttcg     420
aagccaaata cgatttcca cttcgaggtg tttaacttcg tcccgtgtag tatctgctct    480
aataacccca cctgttgggc tatttgcaaa agaatcccta caagaagcc aggaaaaaag     540
acgacaacta aacccaccaa gaagcctacg ttgaaaacaa ctaagaagga cccgaaacca    600
caaaccacga agagcaaaga agttcccaca actaagccta ccgaggaacc gacgatcaat    660
acaactaaga ccaacattat cacgacactg ctcacttcaa ataccactgg taacccagag    720
ctgacctccc agatggaaac cttccattcg acgagttctg agggcaaccc cagcccttcc    780
caagtatcaa caacttcgga atacccatct cagcccagta gccctccgaa taccccacga    840
caa                                                                  843
```

<210> SEQ ID NO 16
<211> LENGTH: 281
<212> TYPE: PRT
<213> ORGANISM: Artificial Sequence
<220> FEATURE:
<223> OTHER INFORMATION: Synthetic

<400> SEQUENCE: 16

```
Met Asn Arg Ala Val Cys Gln Val Ala Leu Glu Asn Asp Glu Arg Glu
1               5                   10                  15

Ala Lys Asn Thr Trp Arg Leu Val Phe Arg Ile Ala Ile Leu Leu Leu
            20                  25                  30

Thr Val Met Thr Leu Ala Ile Ser Ala Ala Leu Ala Tyr Ser Ala
        35                  40                  45

Asn His Lys Val Thr Pro Thr Thr Ala Ile Ile Gln Asp Ala Thr Ser
    50                  55                  60

Gln Ile Lys Asn Thr Thr Pro Thr Tyr Leu Thr Gln Asn Pro Gln Leu
65                  70                  75                  80

Gly Ile Ser Pro Ser Asn Pro Ser Glu Ile Thr Ser Gln Ile Thr Thr
                85                  90                  95

Ile Leu Ala Ser Thr Thr Pro Gly Val Lys Ser Thr Leu Gln Ser Thr
            100                 105                 110

Thr Val Lys Thr Lys Asn Thr Thr Thr Gln Thr Gln Pro Ser Lys
        115                 120                 125

Pro Thr Thr Lys Gln Arg Gln Asn Lys Pro Pro Ser Lys Pro Asn Asn
130                 135                 140

Asp Phe His Phe Glu Val Phe Asn Phe Val Pro Cys Ser Ile Cys Ser
145                 150                 155                 160

Asn Asn Pro Thr Cys Trp Ala Ile Cys Lys Arg Ile Pro Asn Lys Lys
                165                 170                 175

Pro Gly Lys Lys Thr Thr Thr Lys Pro Thr Lys Pro Thr Leu Lys
            180                 185                 190
```

-continued

```
Thr Thr Lys Lys Asp Pro Lys Pro Gln Thr Thr Lys Ser Lys Glu Val
        195                 200                 205

Pro Thr Thr Lys Pro Thr Glu Glu Pro Thr Ile Asn Thr Thr Lys Thr
    210                 215                 220

Asn Ile Ile Thr Thr Leu Leu Thr Ser Asn Thr Thr Gly Asn Pro Glu
225                 230                 235                 240

Leu Thr Ser Gln Met Glu Thr Phe His Ser Thr Ser Ser Glu Gly Asn
                245                 250                 255

Pro Ser Pro Ser Gln Val Ser Thr Thr Ser Glu Tyr Pro Ser Gln Pro
            260                 265                 270

Ser Ser Pro Pro Asn Thr Pro Arg Gln
        275                 280
```

<210> SEQ ID NO 17
<211> LENGTH: 897
<212> TYPE: DNA
<213> ORGANISM: respiratory syncytial virus

<400> SEQUENCE: 17

```
atgtccaaga acaaagacca gcgtaccgct aagactctgg agcgcacatg ggatacgctc     60
aatcacttgc ttttcatctc tagctgcctg tacaaactca acttgaagtc agtggcccaa    120
attacccttt cgatcctggc gatgattatc agtacttccc tcatcattgc agctatcatt    180
tttatcgcct ctgcgaatca taaggtcaca cccacgaccg caatcattca ggacgctact    240
agccaaatca aaaacacaac ccctacgtat ttgactcaga acccacaact gggtatttca    300
ccgtcgaatc ccagtgaaat cacctcccag atcacaacta ttcttgcctc taccacgcct    360
ggcgttaaga gcacactcca atcaactacc gtaaagacga aaaacacaac taccacccag    420
acgcagccat ccaagccgac aactaaacaa aggcagaaca agccccccttc gaagccaaat    480 aacgatttcc acttcgaggt gtttaacttc gtcccgtgta gtatctgctc taataacccc    540
acctgttggg ctatttgcaa aagaatccct aacaagaagc caggaaaaaa gacgacaact    600
aaacccacca agaagcctac gttgaaaaca actaagaagg acccgaaacc acaaaccacg    660
aagagcaaag aagttcccac aactaagcct accgaggaac cgacgatcaa tacaactaag    720
accaacatta tcacgacact gctcacttca aataccactg gtaacccaga gctgacctcc    780
cagatggaaa ccttccattc gacgagttct gagggcaacc ccagcccttc ccaagtatca    840
acaacttcgg aatacccatc tcagcccagt agccctccga ataccccacg acaataa       897
```

<210> SEQ ID NO 18
<211> LENGTH: 298
<212> TYPE: PRT
<213> ORGANISM: respiratory syncytial virus

<400> SEQUENCE: 18

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80
```

-continued

```
Ser Gln Ile Lys Asn Thr Thr Pro Thr Tyr Leu Thr Gln Asn Pro Gln
                 85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
290                 295
```